United States Patent
Hanson et al.

(10) Patent No.: US 7,282,506 B2
(45) Date of Patent: Oct. 16, 2007

(54) 2,8-DISUBSTITUTED NAPHTHYRIDINE DERIVATIVES

(75) Inventors: Gunnar J. Hanson, Chapel Hill, NC (US); Roy W. Ware, Jr., Raleigh, NC (US); Thomas E. Barta, Carrboro, NC (US); He Huang, Northbrook, IL (US)

(73) Assignee: Serenex, Inc., Durham, NC (US)

( * ) Notice: Subject to any disclaimer, the term of this patent is extended or adjusted under 35 U.S.C. 154(b) by 0 days.

(21) Appl. No.: 11/196,532

(22) Filed: Aug. 3, 2005

(65) Prior Publication Data

US 2006/0030584 A1 Feb. 9, 2006

Related U.S. Application Data

(60) Provisional application No. 60/598,518, filed on Aug. 3, 2004.

(51) Int. Cl.
C07D 471/02 (2006.01)
A01N 43/42 (2006.01)
A61K 31/44 (2006.01)

(52) U.S. Cl. ...................... 514/300; 546/122
(58) Field of Classification Search ................ 546/122; 544/238, 333, 405, 362, 127, 61; 514/228.2, 514/233.8, 252.04, 253.04, 255.05, 256, 514/300

See application file for complete search history.

(56) References Cited

U.S. PATENT DOCUMENTS 5,945,431 A * 8/1999 Jin et al. ................... 514/300
2002/0137733 A1 * 9/2002 Falardeau et al. .......... 514/183

FOREIGN PATENT DOCUMENTS

WO 99/29318 * 6/1999

OTHER PUBLICATIONS

Chan et al., Bioorganic & Medicinal Chemistry Letters, "Design and Synthesis of New Potent Human Cytomegalovirus (HCMV) Inhibitors Based on Internally Hydrogen-Bonded 1,6-Naphthyridines", vol. 11, 2001, pp. 103-105.*
Falardeau et al., Bioorganic & Medicinal Chemistry Letters, "Substituted 1,6-Naphthyridines as Human Cytomegalovirus Inhibitors: Conformational Requirements", vol. 10, 2000, pp. 2769-2770.*
Thompson et al., J. Chem. Soc., Perkin Trans. 1, "Synthesis of 7-substituted 3-aryl-1,6-naphthyridin-2-amines and 7-substituted 3-aryl-1,6-naphthyridin-2(1H)-ones via diazotization of 3-aryl-1,6-naphthyridine-2,7-diamines", 2000, pp. 1843-1852.*
Chan et al., J. Med. Chem., "Discovery of 1,6-Naphthyridines as a Novel Class of Potent and Selective Human Cytomegalovirus Inhibitors", vol. 42, 1999, pp. 3023-3025.*
Keating et al., Biodrugs, "Infiximab an updated revies of its use in Crohn's disease and Rheumatoid arthritis", 2002, vol. 16, pp. 111-148.*
DeMartin et al., Arteriosclerosis, Thrombosis, and Vascular Biology, "The Transcription Faction NF-kappa B and the Regulation of Vascular Cell Function", vol. 20, No. 11, 2000, pp. E83-E-88.
Orlowski et al., Trends in Molecular Medicine, "NF-kappa B as a Therapeutic Target in Cancer", vol. 8, No. 8, 2002, pp. 385-389.
Bharti et al., Biochemical Pharmacology, "Nuclear Factor-Kappa B and Cancer: its Role in Prevention and Therapy", vol. 64, No. 5-6, 2002, pp. 883-888.
Panwalkar et al., Cancer, "Nuclear Factor KappaB Modulations as a Therapeutic Approach in Hematologic Malignancies", vol. 100, No. 8, Apr. 15, 2004, pp. 1578-1589.
Thompson et al., Journal of Medicinal Chemistry, American Chemical Society, Washington, US, "3-(3,5-Dimethoxphenyl)-1,6-naphthyridine-2,7-diamines and Related 2-Urea Derivatives are Potent and Selective Inhibitors of the FGF Receptor-1 Tyrosine Kinase", vol. 43, No. 22, 2000, pp. 4200-4211.

* cited by examiner

Primary Examiner—Margaret D. Seaman
Assistant Examiner—Niloofar Rahmani
(74) Attorney, Agent, or Firm—McDonnell Boehnen Hulbert & Berghoff LLP

(57) ABSTRACT

Disclosed are compounds of formula A:

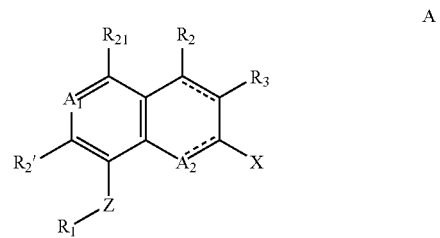

and pharmaceutically acceptable salts thereof, wherein $R_1$, $R_2$, $R_2'$, $R_3$, $R_{21}$, $A_1$, $A_2$, X, and Z are as defined herein. Compounds of formula A are useful in the treatment of diseases and/or conditions related to cell differentiation, such as cancer, inflammation, arthritis, angiogenesis, or the like. Also disclosed are pharmaceutical compositions comprising compounds of the invention and methods of treating the aforementioned conditions using such compounds.

19 Claims, No Drawings

2,8-DISUBSTITUTED NAPHTHYRIDINE DERIVATIVES

BACKGROUND OF THE INVENTION

This application claims priority from U.S. Provisional Application No. 60/598,518, filed Aug. 3, 2004, the disclosure of which is incorporated herein in its entirety.

FIELD OF THE INVENTION

The invention relates to 2,8-disubstituted naphthyridines and more specifically to such compounds that are useful in the treatment and/or prevention of diseases and/or conditions related to cell differentiation, such as cancer, inflammation and inflammation-associated disorders, and conditions associated with angiogenesis.

DESCRIPTION OF THE RELATED ART

Angiogenesis is a highly regulated process under normal conditions, however many diseases are driven by persistent unregulated angiogenesis. Unregulated angiogenesis may either cause a particular disease directly or exacerbate an existing pathological condition. For example, ocular neovascularization has not only been implicated as the most common cause of blindness, but also is believed the dominant cause of many eye diseases. Further, in certain existing conditions, for example arthritis, newly formed capillary blood vessels invade the joints and destroy cartilage, or in the case of diabetes, new capillaries formed in the retina invade the vitreous, bleed, and cause blindness. Growth and metastasis of solid tumors are also dependent on angiogenesis (Folkman, J., Cancer Research, 46, 467-473 (1986), Folkman, J., Journal of the National Cancer Institute, 82, 4-6 (1989). It has been shown, for example, that tumors which enlarge to greater than 2 mm must obtain their own blood supply and do so by inducing the growth of new capillary blood vessels. Once these new blood vessels become embedded in the tumor, they provide a means for tumor cells to enter the circulation and metastasize to distant sites such as liver, lung or bone (Weidner, N., et al., The New England Journal of Medicine, 324(1), 1-8 (1991). Under conditions of unregulated angiogenesis, therapeutic methods designed to control, repress, and/or inhibit angiogenesis could lead to the abrogation or mitigation of these conditions and diseases.

Cancer is characterized by abnormal cellular proliferation. Cancer cells exhibit a number of properties that make them dangerous to the host, typically including an ability to invade other tissues and to induce capillary ingrowth, which assures that the proliferating cancer cells have an adequate supply of blood. A hallmark of cancerous cells is their abnormal response to control mechanisms that regulate cell division in normal cells and continue to divide until they ultimately kill the host.

Inflammation is related to a variety of disorders such as pain, headaches, fever, arthritis, asthma, bronchitis, menstrual cramps, tendinitis, bursitis, psoriasis, eczema, burns, dermatitis, inflammatory bowel syndrome, Crohn's disease, gastritis, irritable bowel syndrome, ulcerative colitis, vascular diseases, Hodgkin's disease, sclerodoma, rheumatic fever, type I diabetes, myasthenia gravis, sarcoidosis, nephrotic syndrome, Behcet's syndrome, polymyositis, hypersensitivity, conjunctivitis, gingivitis, post-injury swelling, myocardial ischemia, and the like.

Therefore, there is a continuing need in the art for new methods of treating cancer, inflammation and inflammation-associated disorders, and conditions or diseases related to uncontrolled angiogenesis.

U.S. Pat. No. 5,945,431 discloses heterocyclic compounds of the formula (I):

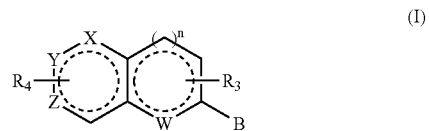

wherein

W is selected from CH, $CR_3$, $CH_2$, C=O, $CHR_3$, N and $NR_5$; one of X, Y, and Z is N or $NR_5$ while the other two are independently selected from CH, $CR_4$, $CH_2$, C=O and $CHR_4$;

B is selected from the group consisting of

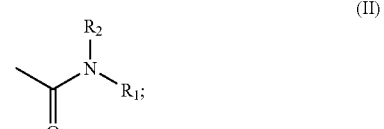

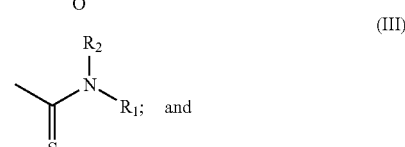

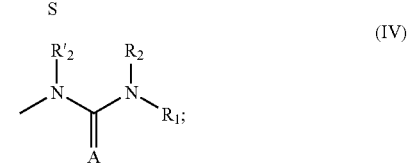

wherein

A is O or S;

$R_1$ is selected from:
  $C_{1-6}$ alkyl, $C_{2-6}$ alkenyl or $C_{3-7}$ cycloalkyl, each of which is optionally substituted with OH, halogen, amino, carboxyl or saturated or unsaturated $C_{3-10}$ (carbocycle or heterocycle) optionally substituted with OH, halogen, amino, mercapto, carboxy, $C_{1-4}$ (alkyl, alkoxy, alkylthio, acyl, acyloxy or alkoxycarbonyl) optionally substituted with OH, halogen, amino or $C_{1-4}$ alkoxy,; and $C_{3-7}$ cycloalkyl fused to $C_{6-10}$ aryl optionally substituted with OH, halogen, amino, mercapto, carboxy, $C_{1-4}$ (alkyl, alkoxy, alkylthio, acyl, acyloxy or alkoxycarbonyl) optionally substituted with OH, halogen, amino or $C_{1-4}$ alkoxy;

$R_2$ and $R'_2$ are independently H, $C_{1-4}$ alkyl or $R_1$ and $R_2$ together form a saturated or unsaturated 5 or 6 member heterocycle optionally fused to $C_{6-10}$ aryl or heteroaryl;

$R_3$ and $R_4$ are independently selected from H, OH, halogen, amino, cyano, $C_{1-6}$ (alkyl, alkoxy, acyl, acyloxy or alkoxycarbonyl), where each alkyl and acyl portion is optionally substituted with OH, halogen, amino or $C_{1-4}$ alkoxy, and saturated or unsaturated $C_{3-10}$ (carbocycle or heterocycle) optionally substituted with OH, halogen, amino, mercapto, $C_{1-4}$ alkylthio, $C_{1-4}$ alkoxycarbonyl, halo substituted $C_{1-4}$ alkyl or halo-substituted $C_{1-4}$ alkoxy, $C_{1-4}$ alkyl, $C_{1-4}$ alkoxy or carboxy;

$R_5$ is H, $C_{1-6}$ alkyl or $C_{1-6}$ acyl, where each of the alkyl and acyl is optionally substituted with OH, halogen, amino or $C_{1-4}$ alkoxy; and n is 0, 1 or 2.

U.S. Pat. No. 5,945,431 discloses how to make the above compounds and how to use them allegedly as cytomegalovirus (CMV) inhibitors for the treatment of conditions related to CMV infection in mammals. The disclosure of U.S. Pat. No. 5,945,431 is incorporated herein by reference in its entirety.

SUMMARY OF THE INVENTION

In a broad aspect, the invention encompasses the compounds of formula A shown below, pharmaceutical compositions containing those compounds and methods employing such compounds or compositions in the treatment of diseases and/or conditions related to cell differentiation, such as cancer, inflammation, arthritis, angiogenesis, or the like.

The invention provides compounds of formula A, hereinafter "Embodiment 1":

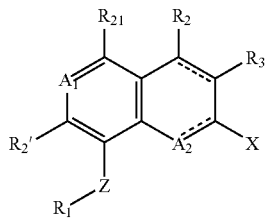

A or pharmaceutically acceptable salts thereof, wherein each ----- independently represents a single bond or a double bond;

$A_1$ is N, or an N-oxide;

$A_2$ is N, an N-oxide, NH, or $N(C_1-C_6)$ alkyl; provided that when ----- is a single bond, then $A_2$ is NH, or $N(C_1-C_6)$ alkyl;

X is $-NR_xR_y$, or $-C(O)R_{20}$; wherein $R_x$ and $R_y$ are independently H, $C_1-C_6$ alkyl, alkoxycarbonyl, arylalkoxycarbonyl, aryl, arylalkyl, —C(O)-aryl, heteroaryl, heteroarylalkyl, or —C(O)heteroaryl, wherein the aryl and heteroaryl rings are optionally substituted with 1, 2, 3, 4, or 5 groups that are independently $C_1-C_6$ alkyl, $C_1-C_6$ alkoxy, halogen, $CO_2H$, $NR_6R_7$, —C(O)$NR_6R_7$, —($C_1-C_4$ alkyl)-$NR_6R_7$, —($C_1-C_4$ alkyl)-C(O)$NR_6R_7$, $C_1-C_4$ haloalkyl, or $C_1-C_4$ haloalkoxy;

Z is a bond, $-CH_2-$, $-NH-$, $-O-$, $-N(C_1-C_6$ alkyl)-, $-S-$, $-S(O)-$, $-SO_2-$, $-SO_2NH-$, or $-SO_2N(C_1-C_6$ alkyl)-;

$R_1$ is halogen, $C_1-C_6$ alkanoyl, $C_1-C_6$ alkyl, $C_2-C_6$ alkynyl, $C_2-C_6$ alkenyl, aryl, heteroaryl, heterocycloalkyl, or $C_3-C_8$ cycloalkyl, each of which is unsubstituted or substituted with 1, 2, 3, 4, or 5 groups that are independently $C_1-C_6$ alkyl, halogen, $C_1-C_6$ alkoxy, OH, CN, $CO_2H$, $C_1-C_4$ haloalkyl, $C_1-C_6$ haloalkoxy, —OC(O)—$C_1-C_6$ alkyl, $C_1-C_6$ alkoxycarbonyl, $C_1-C_6$ alkanoyl, —C(O)$R_{10}$, $NR_6R_7$, —($C_1-C_4$ alkyl)-$NR_6R_7$, —C(O)$NR_6R_7$, heteroaryl, heterocycloalkyl, phenyl, or naphthyl, wherein the heteroaryl, heterocycloalkyl, phenyl and naphthyl groups are optionally substituted with 1 or more groups that are independently selected from $C_1-C_4$ alkyl, $C_1-C_4$ alkoxy, halogen, OH, OH, $CF_3$, and $OCF_3$, wherein each $R_6$ and $R_7$ is independently H, $C_1-C_6$ alkyl, $C_1-C_4$ alkoxyalkyl, $C_1-C_6$ alkoxycarbonyl, wherein the alkyl portion of each is unsubstituted or substituted with 1, 2, or 3, groups that are independently halogen, OH, $C_1-C_4$ haloalkyl, $C_1-C_4$ haloalkoxy, $NH_2$, $NH(C_1-C_6$ alkyl) or $N(C_1-C_6$ alkyl)$(C_1-C_6$ alkyl); or $R_6$ and $R_7$ and the nitrogen to which they are attached form a ring having from 5 to 8 members, wherein the ring optionally contains 1-3 additional heteroatoms selected from N, O, and S, where the ring is optionally substituted with 1, 2, or 3 groups that are independently $C_1-C_6$ alkyl, $C_1-C_6$ alkoxy, halogen, OH, amino, $NH(C_1-C_6$ alkyl), or $N(C_1-C_6$ alkyl)$(C_1-C_6$ alkyl);

$R_{10}$ is $C_2-C_6$ alkenyl, $C_2-C_6$ alkynyl, aryl, heteroaryl, or cycloalkyl, wherein the cyclic portions are optionally substituted with 1, 2, or 3 groups that are independently halogen, $C_1-C_6$ alkyl, $C_1-C_6$ alkoxy, OH, $CO_2H$, CN, $NO_2$, $C_1-C_4$ haloalkyl, or $C_1-C_4$ haloalkoxy;

wherein the heterocycloalkyl and the cycloalkyl portions of $R_1$ and $R_{10}$ are further optionally substituted with =O, =N—OH, or =N—OCH$_3$;

$R_2$, $R_2'$, and $R_3$ at each occurrence are independently H, halogen, $C_1-C_6$ alkyl, $C_2-C_6$ alkynyl, $C_2-C_6$ alkenyl, —C(O)$NH_2$, —C(O)NH($C_1-C_6$ alkyl), —C(O)N($C_1-C_6$ alkyl)$(C_1-C_6$ alkyl), or aryl;

$R_{20}$ is H, OH, $C_1-C_6$ alkoxy, or $NR_4R_5$; wherein $R_4$ and $R_5$ are independently H, $C_1-C_6$ alkyl, $C_1-C_4$ alkoxy $C_1-C_6$ alkyl, $C_2-C_6$ alkynyl, $C_2-C_6$ alkenyl, $C_3-C_8$ cycloalkyl, cycloalkylalkyl, cycloalkylalkenyl, cycloalkylalkynyl, heterocycloalkyl, heterocycloalkylalkyl, heterocycloalkylalkenyl, heterocycloalkylalkynyl, aryl, heteroaryl, heteroarylalkyl, heteroarylalkenyl, heteroarylalkynyl, arylalkyl, arylalkenyl, or arylalkynyl, wherein the cyclic portion of each of the above is unsubstituted or substituted with one or more groups that are independently $C_1-C_6$ alkyl, $C_1-C_6$ alkoxy, halogen, $-SO_2-(C_1-C_6)$ alkyl, $C_1-C_4$ haloalkyl, $C_1-C_4$ haloalkoxy, $NO_2$, CN, OH, aryl $C_1-C_6$ alkyl, $C_1-C_6$ alkoxy $C_1-C_6$ alkyl, $C_1-C_6$ alkoxycarbonyl, $C_1-C_6$ alkanoyl, $NR_7R_8$, or —C(O)$NR_7R_8$, wherein $R_7$ and $R_8$ are independently H or $C_1-C_6$ alkyl, wherein the alkyl is optionally substituted with 1, 2, or 3 groups that are independently $C_1-C_6$ alkoxycarbonyl, halogen, $C_1-C_6$ alkoxy, $C_1-C_6$ alkanoyl, $NH_2$, $NH(C_1-C_6$ alkyl), $N(C_1-C_6$ alkyl)$(C_1-C_6$ alkyl) or $CO_2H$; or $R_7$ and $R_8$ and the nitrogen to which they are attached form a ring having from 5 to 8 members, wherein the ring optionally contains 1-3 additional heteroatoms selected from N, O, and S, where the ring is optionally substituted with 1, 2, or 3 groups that are independently $C_1-C_6$ alkyl, $C_1-C_6$ alkoxy, OH, halogen, amino, $NH(C_1-C_6$ alkyl), or $N(C_1-C_6$ alkyl)$(C_1-C_6$ alkyl);

wherein the heterocycloalkyl and the cycloalkyl portions of $R_4$ and $R_5$ are further optionally substituted with =O, =N—OH, or =N—OCH$_3$; or $R_4$ and $R_5$ and the nitrogen to which they are attached form a heterocycloalkyl ring, which is unsubstituted or substituted with 1 or more groups that are independently $C_1-C_6$ alkyl, $C_1-C_6$ alkoxy, halogen, aryl $C_1-C_6$ alkyl, $C_1$-$C_6$ alkanoyl, OH, =O, heteroaryl, heteroarylalkyl, phenyl, naphthyl, —OCH$_2$CH$_2$O—, —OCH$_2$O—,
  wherein the heteroaryl, phenyl and naphthyl groups are unsubstituted or substituted with 1 or more groups that are independently $C_1$-$C_4$ alkyl, $C_1$-$C_4$ alkoxy, halogen, CF$_3$ or OCF$_3$;
$R_{21}$ is H, CN, amino, monoalkylamino, dialkylamino, OH, halogen, aryl (phenyl or naphthyl each of which is optionally substituted with 1-5 groups that are independently $C_1$-$C_6$ alkyl, $C_1$-$C_6$ alkoxy, halogen, OH, hydroxyl $C_1$-$C_4$ alkyl, haloalkyl (in one aspect, CF$_3$), or haloalkoxy (in one aspect, OCF$_3$)), or heteroaryl (pyridyl, pyrimidyl, indolyl, or (iso)quinolinyl, each of which is optionally substituted with 1-5 groups that are independently $C_1$-$C_6$ alkyl, $C_1$-$C_6$ alkoxy, halogen, OH, hydroxyl $C_1$-$C_4$ alkyl, haloalkyl (in one aspect, CF$_3$), or haloalkoxy (in one aspect, OCF$_3$) ), $C_1$-$C_6$ alkyl, $C_2$-$C_6$ alkynyl, $C_2$-$C_6$ alkenyl, —C(O)NH$_2$, —C(O)NH($C_1$-$C_6$ alkyl), or —C(O)N($C_1$-$C_6$ alkyl) ($C_1$-$C_6$ alkyl);

provided that $R_1$ is halogen only when Z is a bond;

provided that when
$R_{20}$ is NR$_4$R$_5$ and R$_4$ is $C_{1-6}$ alkyl, $C_{2-6}$ alkenyl or $C_{3-7}$ cycloalkyl optionally substituted with OH, halogen, amino, carboxyl or saturated or unsaturated $C_{3-10}$ (carbocycle or heterocycle) optionally substituted with OH, halogen, amino, mercapto, carboxy, $C_{1-4}$ (alkyl, alkoxy, alkylthio, acyl, acyloxy or alkoxycarbonyl) optionally substituted with OH, halogen, amino or $C_{1-4}$ alkoxy; and $C_{3-7}$ cycloalkyl fused to $C_{6-10}$ aryl optionally substituted with OH, halogen, amino, mercapto, carboxy, $C_{1-4}$ (alkyl, alkoxy, alkylthio, acyl, acyloxy or alkoxycarbonyl) optionally substituted with OH, halogen, amino or $C_{1-4}$ alkoxy;
$R_5$ is H, or $C_{1-4}$ alkyl; and
(1) Z is a bond; and
$R_2$ or $R_3$ is H, OH, halogen, amino, cyano, $C_{1-6}$ (alkyl, alkoxy, acyl, acyloxy or alkoxycarbonyl) optionally substituted with OH, halogen, amino or $C_{1-4}$ alkoxy, and saturated or unsaturated $C_{3-10}$ (carbocycle or heterocycle) optionally substituted with OH, halogen, amino, mercapto, $C_{1-4}$ alkylthio, $C_{1-4}$ alkoxycarbonyl, halo substituted $C_{1-4}$ alkyl or halo-substituted $C_{1-4}$ alkoxy, $C_{1-4}$ alkyl, $C_{1-4}$ alkoxy or carboxy; or
(2) Z is a bond;
$R_2$ or $R_3$ is H, OH, halogen, amino, cyano, $C_{1-6}$ (alkyl, alkoxy, acyl, acyloxy or alkoxycarbonyl) optionally substituted with OH, halogen, amino or $C_{1-4}$ alkoxy, and saturated or unsaturated $C_{3-10}$ (carbocycle or heterocycle) optionally substituted with OH, halogen, amino, mercapto, $C_{1-4}$ alkylthio, $C_{1-4}$ alkoxycarbonyl, halo substituted $C_{1-4}$ alkyl or halo-substituted $C_{1-4}$ alkoxy, $C_{1-4}$ alkyl, $C_{1-4}$ alkoxy or carboxy; and
$R_4$ and $R_5$ together form a saturated or unsaturated 5 or 6 member heterocycle optionally fused to $C_{6-10}$ aryl or heteroaryl; then
$R_1$ is not OH, halogen, amino, cyano, $C_{1-6}$ (alkyl, alkoxy, acyl, acyloxy or alkoxycarbonyl) optionally substituted with OH, halogen, amino or $C_{1-4}$ alkoxy, and saturated or unsaturated $C_{3-10}$ (carbocycle or heterocycle) optionally substituted with OH, halogen, amino, mercapto, $C_{1-4}$ alkylthio, $C_{1-4}$ alkoxycarbonyl, halo substituted $C_{1-4}$ alkyl or halo-substituted $C_{1-4}$ alkoxy, $C_{1-4}$ alkyl, $C_{1-4}$ alkoxy or carboxy.

The invention also includes intermediates that are useful in making the compounds of the invention.

The invention also provides pharmaceutical compositions comprising a compound or pharmaceutically acceptable salt of formula A and at least one pharmaceutically acceptable carrier, solvent, adjuvant or diluent.

The invention further provides methods of treating disease such as cancer, inflammation, arthritis, and angiogenesis in a patient in need of such treatment, comprising administering to the patient a compound or pharmaceutically acceptable salt of formula A, or a pharmaceutical composition comprising a compound or salt of formula A.

The invention also provides the use of a compound or salt according to formula A for the manufacture of a medicament for use in treating cancer, inflammation, arthritis, or angiogenesis.

The invention also provides methods of preparing the compounds of the invention and the intermediates used in those methods.

The invention further provides a compound or pharmaceutical composition thereof in a kit with instructions for using he compound or composition.

DETAILED DESCRIPTION OF THE INVENTION

Preferred compounds of formula I include compounds of embodiment 2, i.e., compounds of Formula A wherein,
$R_1$ is halogen, $C_1$-$C_6$ alkanoyl, $C_1$-$C_6$ alkyl, $C_2$-$C_6$ alkynyl, $C_2$-$C_6$ alkenyl, phenyl, naphthyl, thienyl, furanyl, indolyl, pyridyl, pyridazinyl, pyrimidyl, pyrazinyl, triazolyl, imidazolyl, oxazolyl, isoxazolyl, benzofuranyl, 3,4-dihydropyrimidin-2(1H)-onyl, piperidinyl, pyrrolidinyl, piperazinyl, morpholinyl, thiomorpholinyl, S,S-dioxothiomorpholinyl, or $C_3$-$C_8$ cycloalkyl, each of which is unsubstituted or substituted with 1, 2, 3, 4, or 5 groups that are independently $C_1$-$C_6$ alkyl, halogen, $C_1$-$C_6$ alkoxy, OH, CN, CO$_2$H, heteroaryl selected from pyridyl, pyrimidyl, pyrazinyl, (iso)quinolinyl, indolyl, thienyl, furanyl, pyrrolyl, triazinyl, 1H-indazolyl, and benzimidazolyl, heterocycloalkyl selected from piperidinyl, pyrrolidinyl, tetrahydrofuranyl, tetrahydroisoquinolinyl, imidazolidinyl, piperazinyl, morpholinyl, and S,S-dioxomorpholinyl, phenyl, naphthyl, wherein the heteroaryl, heterocycloalkyl, phenyl and naphthyl groups are optionally substituted with 1 or more groups that are independently selected from $C_1$-$C_4$ alkyl, $C_1$-$C_4$ alkoxy, halogen, OH, OH, CF$_3$, and OCF$_3$, $C_1$-$C_4$ haloalkyl, $C_1$-$C_4$ haloalkoxy, —OC(O)—$C_1$-$C_6$ alkyl, $C_1$-$C_6$ alkoxycarbonyl, $C_1$-$C_6$ alkanoyl, —C(O)R$_{10}$, NR$_6$R$_7$, —($C_1$-$C_4$ alkyl)-NR$_6$R$_7$, or —C(O)NR$_6$R$_7$, wherein
  each $R_6$ and $R_7$ is independently H, $C_1$-$C_6$ alkyl, $C_1$-$C_4$ alkoxyalkyl, $C_1$-$C_6$ alkoxycarbonyl, wherein the alkyl portion of each is unsubstituted or substituted with 1, 2, or 3, groups that are independently halogen, OH, $C_1$-$C_4$ haloalkyl, $C_1$-$C_4$ haloalkoxy, NH$_2$, NH($C_1$-$C_6$ alkyl) or N($C_1$-$C_6$ alkyl) ($C_1$-$C_6$ alkyl);
  $R_{10}$ is $C_2$-$C_6$ alkenyl, $C_2$-$C_6$ alkynyl, phenyl, naphthyl, pyridyl, quinolinyl, pyrimidyl, furanyl, indolyl, benzofuranyl, thienyl, cycloalkyl, wherein the cyclic portions are optionally substituted with halogen, $C_1$-$C_6$ alkyl, $C_1$-$C_6$ alkoxy, OH, CO$_2$H, CN, NO$_2$, $C_1$-$C_4$ haloalkyl, or $C_1$-$C_4$ haloalkoxy;

wherein the heterocycloalkyl and the cycloalkyl portions of $R_1$ and $R_{10}$ are further optionally substituted with =O, =N—OH, or =N—OCH$_3$.

Other preferred compounds of Embodiment 1 include those where

X is —C(O)$R_{20}$;

$R_{20}$ is $NR_4R_5$; wherein $R_4$ and $R_5$ are independently H, $C_1$-$C_6$ alkyl, $C_1$-$C_4$ alkoxy $C_1$-$C_6$ alkyl, $C_2$-$C_6$ alkynyl, $C_2$-$C_6$ alkenyl, $C_3$-$C_8$ cycloalkyl, $C_3$-$C_8$ cycloalkyl $C_1$-$C_6$ alkyl, $C_3$-$C_8$ cycloalkyl $C_2$-$C_6$ alkenyl, cycloalkyl $C_2$-$C_6$ alkynyl, piperidinyl, pyrrolidinyl, imidazolidinyl, morpholinyl, thiomorpholinyl, S,S-dioxothiomorpholinyl, tetrahydrofuranyl, tetrahydrothienyl, morpholinyl $C_1$-$C_6$ alkyl, thiomorpholinyl $C_1$-$C_6$ alkyl, S,S-dioxothiomorpholinyl $C_1$-$C_6$ alkyl, piperidinyl $C_1$-$C_6$ alkyl, pyrrolidinyl $C_1$-$C_6$ alkyl, imidazolidinyl $C_1$-$C_6$ alkyl, piperidinyl $C_2$-$C_6$ alkenyl, pyrrolidinyl $C_2$-$C_6$ alkenyl, imidazolidinyl $C_2$-$C_6$ alkenyl, morpholinyl $C_2$-$C_6$ alkenyl, thiomorpholinyl $C_2$-$C_6$ alkenyl, S,S-dioxothiomorpholinyl $C_2$-$C_6$ alkenyl, tetrahydrofuranyl $C_2$-$C_6$ alkenyl, tetrahydrothienyl $C_2$-$C_6$ alkenyl, piperidinyl $C_2$-$C_6$ alkynyl, pyrrolidinyl $C_2$-$C_6$ alkynyl, imidazolidinyl $C_2$-$C_6$ alkynyl, morpholinyl $C_2$-$C_6$ alkynyl, thiomorpholinyl $C_2$-$C_6$ alkynyl, S,S-dioxothiomorpholinyl $C_2$-$C_6$ alkynyl, tetrahydrofuranyl $C_2$-$C_6$ alkynyl, tetrahydrothienyl $C_2$-$C_6$ alkynyl, phenyl, naphthyl, furanyl, pyridyl, pyrimidyl, pyrazinyl, thienyl, imidazolyl, pyrazinyl $C_1$-$C_6$ alkyl, pyridyl $C_1$-$C_6$ alkyl, pyrimidyl $C_1$-$C_6$ alkyl, pyrazinyl $C_1$-$C_6$ alkyl, imidazolyl $C_1$-$C_6$ alkyl, furanyl $C_1$-$C_6$ alkyl, thienyl $C_1$-$C_6$ alkyl, heteroarylalkenyl, heteroarylalkynyl, phenyl $C_1$-$C_6$ alkyl, naphthyl $C_1$-$C_6$ alkyl, phenyl $C_2$-$C_6$ alkenyl, naphthyl $C_2$-$C_6$ alkenyl, phenyl $C_2$-$C_6$ alkynyl, naphthyl $C_2$-$C_6$ alkynyl, wherein the cyclic portion of each of the above is unsubstituted or substituted with one or more groups that are independently $C_1$-$C_6$ alkyl, $C_1$-$C_6$ alkoxy, halogen, —$SO_2$—($C_1$-$C_6$) alkyl, $C_1$-$C_4$ haloalkyl, $C_1$-$C_4$ haloalkoxy, $NO_2$, CN, OH, phenyl $C_1$-$C_6$ alkyl wherein the phenyl is optionally substituted with 1, 2, 3, 4, or 5 groups that are independently selected from $C_1$-$C_4$ alkyl, $C_1$-$C_4$ alkoxy, CN, halogen, OH, and alkanoyl, $C_1$-$C_6$ alkoxy $C_1$-$C_6$ alkyl, $C_1$-$C_6$ alkoxycarbonyl, $C_1$-$C_6$ alkanoyl, $NR_7R_8$, or —C(O)$NR_7R_8$, wherein $R_7$ and $R_8$ are independently H or $C_1$-$C_6$ alkyl, wherein the $C_1$-$C_6$ alkyl is optionally substituted with 1, 2, or 3 groups that are independently $C_1$-$C_6$ alkoxycarbonyl, halogen, $C_1$-$C_6$ alkoxy, $C_1$-$C_6$ alkanoyl, $NH_2$, NH($C_1$-$C_6$ alkyl), N($C_1$-$C_6$ alkyl)($C_1$-$C_6$ alkyl) or $CO_2H$;

wherein the heterocycloalkyl and the cycloalkyl portions of $R_4$ and $R_5$ are further optionally substituted with =O, =N—OH, or =N—$OCH_3$; or $R_4$ and $R_5$ and the nitrogen to which they are attached form a piperazinyl, morpholinyl, piperidinyl, pyrrolidinyl, thiomorpholinyl, imidazolidinyl, S,S,-dioxothiomorpholinyl, piperidinyl, pyrrolidinyl, ring, which is unsubstituted or substituted with 1 or more groups that are independently $C_1$-$C_6$ alkyl, $C_1$-$C_6$ alkoxy, halogen, phenyl $C_1$-$C_6$ alkyl, naphthyl $C_1$-$C_6$ alkyl, $C_1$-$C_6$ alkanoyl, OH, =O, pyridyl, pyrimidyl, pyrazinyl, pyrimidyl $C_1$-$C_6$ alkyl, pyrazinyl $C_1$-$C_6$ alkyl, phenyl, naphthyl, —$OCH_2CH_2O$—, —$OCH_2O$—, wherein the pyridyl, pyrimidyl, pyrazinyl, pyrimidyl $C_1$-$C_6$ alkyl, phenyl and naphthyl groups are unsubstituted or substituted with 1 or more groups that are independently $C_1$-$C_4$ alkyl, $C_1$-$C_4$ alkoxy, halogen, $CF_3$ or $OCF_3$.

Other preferred compounds of Embodiment 1 include those of embodiment 4, i.e., compounds of Embodiment 1 where $R_1$ is halogen, $C_1$-$C_6$ alkanoyl, $C_1$-$C_6$ alkyl, $C_2$-$C_6$ alkynyl, $C_2$-$C_6$ alkenyl, phenyl, naphthyl, thienyl, furanyl, indolyl, pyridyl, pyridazinyl, pyrimidyl, pyrazinyl, triazolyl, imidazolyl, oxazolyl, isoxazolyl, benzofuranyl, 3,4-dihydropyrimidin-2(1H)-onyl, piperidinyl, pyrrolidinyl, piperazinyl, morpholinyl, thiomorpholinyl, S,S-dioxothiomorpholinyl, or $C_3$-$C_8$ cycloalkyl, each of which is unsubstituted or substituted with 1, 2, 3, 4, or 5 groups that are independently $C_1$-$C_6$ alkyl, halogen, $C_1$-$C_6$ alkoxy, OH, CN, $CO_2H$, heteroaryl selected from pyridyl, pyrimidyl, pyrazinyl, (iso)quinolinyl, indolyl, thienyl, furanyl, pyrrolyl, triazinyl, 1H-indazolyl, and benzimidazolyl, heterocycloalkyl selected from piperidinyl, pyrrolidinyl, tetrahydrofuranyl, tetrahydroisoquinolinyl, imidazolidinyl, piperazinyl, morpholinyl, and S,S-dioxomorpholinyl, phenyl, naphthyl, wherein the heteroaryl, heterocycloalkyl, phenyl and naphthyl groups are optionally substituted with 1 or more groups that are independently selected from $C_1$-$C_4$ alkyl, $C_1$-$C_4$ alkoxy, halogen, OH, OH, $CF_3$, and $OCF_3$, $C_1$-$C_4$ haloalkyl, $C_1$-$C_4$ haloalkoxy, —OC(O)—$C_1$-$C_6$ alkyl, $C_1$-$C_6$ alkoxycarbonyl, $C_1$-$C_6$ alkanoyl, —C(O)$R_{10}$, $NR_6R_7$, —($C_1$-$C_4$ alkyl) —$NR_6R_7$, or —C(O)$NR_6R_7$, wherein each $R_6$ and $R_7$ is independently H, $C_1$-$C_6$ alkyl, $C_1$-$C_4$ alkoxyalkyl, $C_1$-$C_6$ alkoxycarbonyl, wherein the alkyl portion of each is unsubstituted or substituted with 1, 2, or 3, groups that are independently halogen, OH, $C_1$-$C_4$ haloalkyl, $C_1$-$C_4$ haloalkoxy, $NH_2$, NH($C_1$-$C_6$ alkyl) or N($C_1$-$C_6$ alkyl) ($C_1$-$C_6$ alkyl);

$R_{10}$ is $C_2$-$C_6$ alkenyl, $C_2$-$C_6$ alkynyl, phenyl, naphthyl, pyridyl, quinolinyl, pyrimidyl, furanyl, indolyl, $C_3$-$C_8$ cycloalkyl, wherein the cyclic portions are optionally substituted with halogen, $C_1$-$C_6$ alkyl, $C_1$-$C_6$ alkoxy, OH, $CO_2H$, CN, $NO_2$, $C_1$-$C_4$ haloalkyl, or $C_1$-$C_4$ haloalkoxy;

wherein the heterocycloalkyl and the cycloalkyl portions of $R_1$ and $R_{10}$ are further optionally substituted with =O, =N—OH, or =N—$OCH_3$; and $R_4$ and $R_5$ are independently H, $C_1$-$C_6$ alkyl, $C_1$-$C_4$ alkoxy $C_1$-$C_6$ alkyl, $C_2$-$C_6$ alkynyl, $C_2$-$C_6$ alkenyl, $C_3$-$C_8$ cycloalkyl, $C_3$-$C_8$ cycloalkyl $C_1$-$C_6$ alkyl, $C_3$-$C_8$ cycloalkyl $C_2$-$C_6$ alkenyl, cycloalkyl $C_2$-$C_6$ alkynyl, piperidinyl, pyrrolidinyl, imidazolidinyl, morpholinyl, thiomorpholinyl, S,S-dioxothiomorpholinyl, tetrahydrofuranyl, tetrahydrothienyl, morpholinyl $C_1$-$C_6$ alkyl, thiomorpholinyl $C_1$-$C_6$ alkyl, S,S-dioxothiomorpholinyl $C_1$-$C_6$ alkyl, piperidinyl $C_1$-$C_6$ alkyl, pyrrolidinyl $C_1$-$C_6$ alkyl, imidazolidinyl $C_1$-$C_6$ alkyl, piperidinyl $C_2$-$C_6$ alkenyl, pyrrolidinyl $C_2$-$C_6$ alkenyl, imidazolidinyl $C_2$-$C_6$ alkenyl, morpholinyl $C_2$-$C_6$ alkenyl, thiomorpholinyl $C_2$-$C_6$ alkenyl, S,S-dioxothiomorpholinyl $C_2$-$C_6$ alkenyl, tetrahydrofuranyl $C_2$-$C_6$ alkenyl, tetrahydrothienyl $C_2$-$C_6$ alkenyl, piperidinyl $C_2$-$C_6$ alkynyl, pyrrolidinyl $C_2$-$C_6$ alkynyl, imidazolidinyl $C_2$-$C_6$ alkynyl, morpholinyl $C_2$-$C_6$ alkynyl, thiomorpholinyl $C_2$-$C_6$ alkynyl, S,S-dioxothiomorpholinyl $C_2$-$C_6$ alkynyl, tetrahydrofuranyl $C_2$-$C_6$ alkynyl, tetrahydrothienyl $C_2$-$C_6$ alkynyl, phenyl, naphthyl, furanyl, pyridyl, pyrimidyl, pyrazinyl, thienyl, imidazolyl, pyrazinyl $C_1$-$C_6$ alkyl, pyridyl $C_1$-$C_6$ alkyl, pyrimidyl $C_1$-$C_6$ alkyl, pyrazinyl $C_1$-$C_6$ alkyl, imidazolyl $C_1$-$C_6$ alkyl, furanyl $C_1$-$C_6$ alkyl, thienyl $C_1$-$C_6$ alkyl, heteroarylalkenyl, heteroarylalkynyl, phenyl $C_1$-$C_6$ alkyl, naphthyl $C_1$-$C_6$ alkyl, phenyl $C_2$-$C_6$ alkenyl, naphthyl $C_2$-$C_6$ alkenyl, phenyl $C_2$-$C_6$ alkynyl, naphthyl $C_2$-$C_6$ alkynyl, wherein the cyclic portion of each of the above is unsubstituted or substituted with one or more groups that are independently $C_1$-$C_6$ alkyl, $C_1$-$C_6$ alkoxy, halogen, —SO$_2$—(C$_1$-C$_6$) alkyl, C$_1$-C$_4$ haloalkyl, C$_1$-C$_4$ haloalkoxy, NO$_2$, CN, OH, phenyl C$_1$-C$_6$ alkyl wherein the phenyl is optionally substituted with 1, 2, 3, 4, or 5 groups that are independently selected from C$_1$-C$_4$ alkyl, C$_1$-C$_4$ alkoxy, CN, halogen, OH, and alkanoyl, C$_1$-C$_6$ alkoxy C$_1$-C$_6$ alkyl, C$_1$-C$_6$ alkoxycarbonyl, C$_1$-C$_6$ alkanoyl, NR$_7$R$_8$, or —C(O)NR$_7$R$_8$, wherein R$_7$ and R$_8$ are independently H or C$_1$-C$_6$ alkyl, wherein the C$_1$-C$_6$ alkyl is optionally substituted with 1, 2, or 3 groups that are independently C$_1$-C$_6$ alkoxycarbonyl, halogen, C$_1$-C$_6$ alkoxy, C$_1$-C$_6$ alkanoyl, NH$_2$, NH(C$_1$-C$_6$ alkyl), N(C$_1$-C$_6$ alkyl) (C$_1$-C$_6$ alkyl) or CO$_2$H;

wherein the heterocycloalkyl and the cycloalkyl portions of the above are further optionally substituted with =O, =N—OH, or =N—OCH$_3$; or R$_4$ and R$_5$ and the nitrogen to which they are attached form a piperazinyl, morpholinyl, piperidinyl, thiomorpholinyl, imidazolidinyl, S,S,-dioxothiomorpholinyl, piperidinyl, pyrrolidinyl, ring, which is unsubstituted or substituted with 1 or more groups that are independently C$_1$-C$_6$ alkyl, C$_1$-C$_6$ alkoxy, halogen, phenyl C$_1$-C$_6$ alkyl, naphthyl C$_1$-C$_6$ alkyl, C$_1$-C$_6$ alkanoyl, OH, =O, pyridyl, pyrimidyl, pyrazinyl, pyrimidyl C$_1$-C$_6$ alkyl, pyrazinyl C$_1$-C$_6$ alkyl, phenyl, naphthyl, —OCH$_2$CH$_2$O—, —OCH$_2$O—, wherein the pyridyl, pyrimidyl, pyrazinyl, pyrimidyl C$_1$-C$_6$ alkyl, phenyl and naphthyl groups are unsubstituted or substituted with 1 or more groups that are independently C$_1$-C$_4$ alkyl, C$_1$-C$_4$ alkoxy, halogen, CF$_3$ or OCF$_3$.

Preferred compounds of Embodiment 4 include those of embodiment 5, i.e., compounds of Embodiment 4 where R$_2$ and R$_3$ are independently H, halogen, or C$_1$-C$_6$ alkyl. In another aspect, R$_2$ and R$_3$ are independently H or C$_1$-C$_4$ alkyl.

Other preferred compounds of Embodiment 5 include those of embodiment 6, i.e., compounds of Embodiment 5 where Z is a bond, —CH$_2$—, or —NH—.

Other preferred compounds of Embodiment 6 include those of embodiment 7, i.e., compounds of Embodiment 6 where R$_1$ is halogen, C$_1$-C$_6$ alkyl, C$_2$-C$_6$ alkynyl, phenyl, thienyl, pyridyl, triazolyl, imidazolyl, pyrazinyl, benzofuranyl, 3,4-dihydropyrimidin-2(1H)-onyl, each of which is unsubstituted or substituted with 1, 2, 3, 4, or 5 groups that are independently C$_1$-C$_6$ alkyl, halogen, C$_1$-C$_6$ alkoxy, OH, CN, CO$_2$H, heteroaryl selected from pyridyl, pyrimidyl, pyrazinyl, indolyl, thienyl, furanyl, pyrrolyl, and benzimidazolyl, heterocycloalkyl selected from piperidinyl, pyrrolidinyl, piperazinyl, morpholinyl, and S,S-dioxomorpholinyl, phenyl, or naphthyl, wherein the heteroaryl, heterocycloalkyl, phenyl and naphthyl groups are optionally substituted with 1 or more groups that are independently selected from C$_1$-C$_4$ alkyl, C$_1$-C$_4$ alkoxy, halogen, OH, OH, CF$_3$, and OCF$_3$, C$_1$-C$_4$ haloalkyl, C$_1$-C$_4$ haloalkoxy, —OC(O)—C$_1$-C$_6$ alkyl, C$_1$-C$_6$ alkoxycarbonyl, C$_1$-C$_6$ alkanoyl, —C(O) R$_{10}$, or, NR$_6$R$_7$, —(C$_1$-C$_4$ alkyl) —NR$_6$R$_7$, —C(O)NR$_6$R$_7$, wherein each R$_6$ and R$_7$ is independently H, C$_1$-C$_6$ alkyl, C$_1$-C$_4$ alkoxyalkyl, C$_1$-C$_6$ alkoxycarbonyl, wherein the alkyl portion of each is unsubstituted or substituted with 1, 2, or 3, groups that are independently halogen, OH, C$_1$-C$_4$ haloalkyl, C$_1$-C$_4$ haloalkoxy, NH$_2$, NH(C$_1$-C$_6$ alkyl) or N (C$_1$-C$_6$ alkyl) (C$_1$-C$_6$ alkyl); and R$_{10}$ is phenyl, pyridyl, or C$_3$-C$_8$ cycloalkyl, wherein the cyclic portions are optionally substituted with halogen, C$_1$-C$_6$ alkyl, C$_1$-C$_6$ alkoxy, OH, CO$_2$H, CN, NO$_2$, C$_1$-C$_4$ haloalkyl, or C$_1$-C$_4$ haloalkoxy.

Other preferred compounds of Embodiment 7 include those of Embodiment 8, i.e., compounds of Embodiment 7 where R$_4$ and R$_5$ are independently H, C$_1$-C$_6$ alkyl, C$_1$-C$_4$ alkoxy C$_1$-C$_6$ alkyl, C$_3$-C$_8$ cycloalkyl, piperidinyl, pyrrolidinyl, morpholinyl, morpholinyl C$_1$-C$_6$ alkyl, piperidinyl C$_1$-C$_6$ alkyl, pyrrolidinyl C$_1$-C$_6$ alkyl, piperidinyl C$_2$-C$_6$ alkenyl, pyrrolidinyl C$_2$-C$_6$ alkenyl, morpholinyl C$_2$-C$_6$ alkenyl, piperidinyl C$_2$-C$_6$ alkynyl, pyrrolidinyl C$_2$-C$_6$ alkynyl, morpholinyl C$_2$-C$_6$ alkynyl, phenyl, furanyl, pyridyl, pyrazinyl C$_1$-C$_6$ alkyl, pyridyl C$_1$-C$_6$ alkyl, imidazolyl C$_1$-C$_6$ alkyl, furanyl C$_1$-C$_6$ alkyl, thienyl C$_1$-C$_6$ alkyl, phenyl C$_1$-C$_6$ alkyl, phenyl C$_2$-C$_6$ alkenyl, phenyl C$_2$-C$_6$ alkynyl, wherein the cyclic portion of each of the above is unsubstituted or substituted with one or more groups that are independently C$_1$-C$_6$ alkyl, C$_1$-C$_6$ alkoxy, halogen, —SO$_2$—(C$_1$-C$_6$) alkyl, C$_1$-C$_4$ haloalkyl, C$_1$-C$_4$ haloalkoxy, NO$_2$, CN, OH, phenyl C$_1$-C$_6$ alkyl wherein the phenyl is optionally substituted with 1, 2, 3, 4, or 5 groups that are independently selected from C$_1$-C$_4$ alkyl, C$_1$-C$_4$ alkoxy, CN, halogen, OH, and alkanoyl, C$_1$-C$_6$ alkoxy C$_1$-C$_6$ alkyl, C$_1$-C$_6$ alkoxycarbonyl, C$_1$-C$_6$ alkanoyl, NR$_7$R$_8$, or —C(O)NR$_7$R$_8$, wherein R$_7$ and R$_8$ are independently H or C$_1$-C$_6$ alkyl, wherein the C$_1$-C$_6$ alkyl is optionally substituted with 1, 2, or 3 groups that are independently C$_1$-C$_6$ alkoxycarbonyl, halogen, C$_1$-C$_6$ alkoxy, C$_1$-C$_6$ alkanoyl, NH$_2$, NH(C$_1$-C$_6$ alkyl), N(C$_1$-C$_6$ alkyl) (C$_1$-C$_6$ alkyl) or CO$_2$H;

wherein the heterocycloalkyl and the cycloalkyl portions of R$_4$ and R$_5$ are further optionally substituted with =O, =N—OH, or =N—OCH$_3$.

Other preferred compounds of Embodiment 8 include those of Embodiment 9, i.e., compounds of Embodiment 8 where Z is —NH— or —CH$_2$—;

R$_1$ is C$_1$-C$_6$ alkyl, C$_2$-C$_6$ alkynyl, phenyl, thienyl, pyridyl, triazolyl, imidazolyl, pyrazinyl, benzofuranyl, 3,4-dihydropyrimidin-2(1H)-onyl, each of which is unsubstituted or substituted with 1, 2, 3, 4, or 5 groups that are independently C$_1$-C$_6$ alkyl, halogen, C$_1$-C$_6$ alkoxy, OH, CN, CO$_2$H, heteroaryl selected from pyridyl, pyrimidyl, indolyl, thienyl, furanyl, and benzimidazolyl, heterocycloalkyl selected from piperidinyl, pyrrolidinyl, piperazinyl, morpholinyl, and S,S-dioxomorpholinyl, phenyl, naphthyl, wherein the heteroaryl, heterocycloalkyl, phenyl and naphthyl groups are optionally substituted with phenyl, wherein the phenyl is optionally substituted with 1 or more groups that are independently selected from C$_1$-C$_4$ alkyl, C$_1$-C$_4$ alkoxy, halogen, OH, OH, CF$_3$, and OCF$_3$, CF$_3$, OCF$_3$, —OC(O)—C$_1$-C$_6$ alkyl, C$_1$-C$_6$ alkoxycarbonyl, C$_1$-C$_6$ alkanoyl, NR$_6$R$_7$, —(C$_1$-C$_4$ alkyl)-NR$_6$R$_7$, or —C(O)NR$_6$R$_7$, wherein each R$_6$ and R$_7$ is independently H, C$_1$-C$_6$ alkyl, C$_1$-C$_4$ alkoxyalkyl, C$_1$-C$_6$ alkoxycarbonyl, wherein the alkyl portion of each is unsubstituted or substituted with 1, 2, or 3, groups that are independently halogen, OH, C$_1$-C$_4$ haloalkyl, C$_1$-C$_4$ haloalkoxy, NH$_2$, NH(C$_1$-C$_6$ alkyl) or N(C$_1$-C$_6$ alkyl) (C$_1$-C$_6$ alkyl); and and R$_4$ and R$_5$ are independently H, C$_1$-C$_6$ alkyl, C$_1$-C$_4$ alkoxy C$_1$-C$_6$ alkyl, C$_3$-C$_8$ cycloalkyl, piperidinyl, pyrrolidinyl, morpholinyl, morpholinyl C$_1$-C$_6$ alkyl, piperidinyl C$_1$-C$_6$ alkyl, pyrrolidinyl C$_1$-C$_6$ alkyl, phenyl, furanyl, pyridyl, pyrazinyl C$_1$-C$_6$ alkyl, pyridyl C$_1$-C$_6$ alkyl, imidazolyl $C_1$-$C_6$ alkyl, furanyl $C_1$-$C_4$ alkyl, thienyl $C_1$-$C_6$ alkyl, phenyl $C_1$-$C_6$ alkyl, wherein the cyclic portion of each of the above is unsubstituted or substituted with one or more groups that are independently $C_1$-$C_6$ alkyl, $C_1$-$C_6$ alkoxy, halogen, —$SO_2$—($C_1$-$C_6$) alkyl, $CF_3$, $OCF_3$, $NO_2$, CN, OH, phenyl $C_1$-$C_6$ alkyl wherein the phenyl is optionally substituted with 1, 2, 3, 4, or 5 groups that are independently selected from $C_1$-$C_4$ alkyl, $C_1$-$C_4$ alkoxy, CN, halogen, OH, and alkanoyl, $C_1$-$C_6$ alkoxy $C_1$-$C_6$ alkyl, $C_1$-$C_6$ alkoxycarbonyl, $C_1$-$C_6$ alkanoyl, $NR_7R_8$, or —$C(O)NR_7R_8$, wherein $R_7$ and $R_8$ are independently H or $C_1$-$C_6$ alkyl, wherein the $C_1$-$C_6$ alkyl is optionally substituted with 1, 2, or 3 groups that are independently $C_1$-$C_6$ alkoxycarbonyl, halogen, $C_1$-$C_6$ alkoxy, $C_1$-$C_6$ alkanoyl, $NH_2$, $NH(C_1$-$C_6$ alkyl), $N(C_1$-$C_6$ alkyl) ($C_1$-$C_6$ alkyl) or $CO_2H$;

wherein the heterocycloalkyl and the cycloalkyl portions of $R_4$ and $R_5$ are further optionally substituted with =O, =N—OH, or =N—$OCH_3$.

Other preferred compounds of Embodiment 9 include those of Embodiment 10, i.e., compounds of Embodiment 9 where $R_1$ is phenyl, thienyl, pyridyl, imidazolyl, pyrazinyl, benzofuranyl, each of which is unsubstituted or substituted with 1, 2, or 3 groups that are independently $C_1$-$C_6$ alkyl, halogen, $C_1$-$C_6$ alkoxy, OH, CN, $CO_2H$, pyridyl, piperidinyl, pyrrolidinyl, piperazinyl, morpholinyl or phenyl, wherein the pyridyl, pyrrolidinyl, morpholinyl, and phenyl groups are optionally substituted with 1 or more groups that are independently selected from $C_1$-$C_4$ alkyl, $C_1$-$C_4$ alkoxy, halogen, OH, OH, $CF_3$, and $OCF_3$, $CF_3$, $OCF_3$, —OC(O)—$C_1$-$C_6$ alkyl, $C_1$-$C_6$ alkoxycarbonyl, $C_1$-$C_6$ alkanoyl, $NR_6R_7$, —($C_1$-$C_4$ alkyl)—$NR_6R_7$, or —$C(O)NR_6R_7$, wherein each $R_6$ and $R_7$ is independently H, $C_1$-$C_6$ alkyl, or $C_1$-$C_6$ alkoxycarbonyl (in one aspect, tert-butylalkoxycarbonyl), wherein the alkyl portion of each is unsubstituted or substituted with 1, 2, or 3, groups that are independently halogen, OH, $CF_3$, $OCF_3$, $NH_2$, $NH(C_1$-$C_6$ alkyl) or $N(C_1$-$C_6$ alkyl) ($C_1$-$C_6$ alkyl); and and $R_4$ and $R_5$ are independently H, $C_1$-$C_4$ alkyl, $C_3$-$C_6$ cycloalkyl, piperidinyl, pyrrolidinyl, morpholinyl $C_1$-$C_4$ alkyl, piperidinyl $C_1$-$C_4$ alkyl, phenyl, furanyl, pyridyl, pyrazinyl $C_1$-$C_4$ alkyl, pyridyl $C_1$-$C_4$ alkyl, imidazolyl $C_1$-$C_4$ alkyl, furanyl $C_1$-$C_4$ alkyl, thienyl $C_1$-$C_4$ alkyl, phenyl $C_1$-$C_4$ alkyl, wherein the cyclic portion of each of the above is unsubstituted or substituted with one or more groups that are independently $C_1$-$C_6$ alkyl, $C_1$-$C_6$ alkoxy, halogen, —$SO_2$—($C_1$-$C_4$) alkyl, $CF_3$, $OCF_3$, $NO_2$, CN, OH, $NR_7R_8$, or —$C(O)NR_7R_8$, wherein $R_7$ and $R_8$ are independently H or $C_1$-$C_6$ alkyl, wherein the $C_1$-$C_6$ alkyl is optionally substituted with 1, or 2 groups that are independently $C_1$-$C_6$ alkoxycarbonyl, halogen, $C_1$-$C_6$ alkoxy, $C_1$-$C_6$ alkanoyl, $NH_2$, $NH(C_1$-$C_6$ alkyl), $N(C_1$-$C_6$ alkyl) ($C_1$-$C_6$ alkyl) or $CO_2H$;

wherein the heterocycloalkyl and the cycloalkyl portions of $R_4$ and $R_5$ are further optionally substituted with =O, =N—OH, or =N—$OCH_3$.

Other preferred compounds of Embodiment 10 include those of Embodiment 11, i.e., compounds of Embodiment 10 where $R_4$ is H or methyl; and $R_5$ is —$CH_2$-furanyl.

Other preferred compounds of Embodiment 11 include those of Embodiment 12, i.e., compounds of Embodiment 11 where $R_1$ is phenyl, thienyl, pyridyl, or pyrazinyl, each of which is unsubstituted or substituted with 1, 2, or 3 groups that are independently $C_1$-$C_6$ alkyl, halogen, $C_1$-$C_6$ alkoxy, OH, $CF_3$, $OCF_3$, $NR_6R_7$, —($C_1$-$C_2$ alkyl)-$NR_6R_7$, or —$C(O)NR_6R_7$, wherein each $R_6$ and $R_7$ at each occurrence are independently H, $C_1$-$C_6$ alkyl, or $C_1$-$C_4$ alkoxycarbonyl.

Other preferred compounds of Embodiment 12 include those of Embodiment 12A, i.e., compounds of Embodiment 12 where $R_1$ is phenyl, which is unsubstituted or substituted with 1, 2, or 3 groups that are independently $C_1$-$C_6$ alkyl, halogen, $C_1$-$C_6$ alkoxy, OH, $CF_3$, $OCF_3$, $NR_6R_7$, —($C_1$-$C_2$ alkyl)—$NR_6R_7$, or —$C(O)NR_6R_7$, wherein $R_6$ and $R_7$ at each occurrence are independently H, $C_1$-$C_6$ alkyl, or $C_1$-$C_4$ alkoxycarbonyl. In another aspect, $R_6$ and $R_7$ are independently H or $C_1$-$C_4$ alkyl.

Other preferred compounds of Embodiment 12 include those of Embodiment 12B, i.e., compounds of Embodiment 12 where $R_1$ is thienyl, which is unsubstituted or substituted with 1, 2, or 3 groups that are independently $C_1$-$C_6$ alkyl, halogen, $C_1$-$C_6$ alkoxy, OH, $CF_3$, $OCF_3$, $NR_6R_7$, —($C_1$-$C_2$ alkyl)—$NR_6R_7$, or —$C(O)NR_6R_7$, wherein $R_6$ and $R_7$ at each occurrence are independently H, $C_1$-$C_6$ alkyl, or $C_1$-$C_4$ alkoxycarbonyl. In another aspect, $R_6$ and $R_7$ are independently H or $C_1$-$C_4$ alkyl.

Other preferred compounds of Embodiment 12 include those of Embodiment 12C, i.e., compounds of Embodiment 12 where $R_1$ is pyridyl, which is unsubstituted or substituted with 1, 2, or 3 groups that are independently $C_1$-$C_6$ alkyl, halogen, $C_1$-$C_6$ alkoxy, OH, $CF_3$, $OCF_3$, $NR_6R_7$, —($C_1$-$C_2$ alkyl)—$NR_6R_7$, or —$C(O)NR_6R_7$, wherein $R_6$ and $R_7$ at each occurrence are independently H, $C_1$-$C_6$ alkyl, or $C_1$-$C_4$ alkoxycarbonyl. In another aspect, $R_6$ and $R_7$ are independently H or $C_1$-$C_4$ alkyl.

Other preferred compounds of Embodiment 12 include those of Embodiment 12D, i.e., compounds of Embodiment 12 where $R_1$ is pyrazinyl, which is unsubstituted or substituted with 1, 2, or 3 groups that are independently $C_1$-$C_6$ alkyl, halogen, $C_1$-$C_6$ alkoxy, OH, $CF_3$, $OCF_3$, $NR_6R_7$, —($C_1$-$C_2$ alkyl)—$NR_6R_7$, or —$C(O)NR_6R_7$, wherein $R_6$ and $R_7$ at each occurrence are independently H, $C_1$-$C_6$ alkyl, or $C_1$-$C_4$ alkoxycarbonyl. In another aspect, $R_6$ and $R_7$ are independently H or $C_1$-$C_4$ alkyl.

Other preferred compounds of the invention are within Embodiment 12E, i.e., compounds of embodiments 12, 12A, 12B, 12C, and 12D, wherein at least one of $R_2$ and $R_3$ is H. In another aspect, both $R_2$ and $R_3$ are H.

More preferred compounds of the invention include those of Embodiment 12F, i.e., compounds according to embodiment 12E wherein $R_4$ is H.

Still other preferred compounds of Embodiment 6 include those of embodiment 13, i.e., compounds of Embodiment 6 where $R_4$ and $R_5$ and the nitrogen to which they are attached form a piperazinyl, morpholinyl, piperidinyl, imidazolidinyl, or pyrrolidinyl ring, each of which is unsubstituted or substituted with 1 or more groups that are independently $C_1$-$C_4$ alkyl, $C_1$-$C_4$ alkoxy, halogen, phenyl $C_1$-$C_4$ alkyl, $C_1$-$C_6$ alkanoyl, OH, pyridyl, pyrimidyl, pyrazinyl, pyrimidyl $C_1$-$C_4$ alkyl, pyrazinyl $C_1$-$C_4$ alkyl, phenyl, —$OCH_2CH_2O$—, —$OCH_2O$—, wherein the pyridyl, pyrimidyl, pyrazinyl, pyrimidyl $C_1$-$C_6$ alkyl, and phenyl groups are unsubstituted or substituted with 1 or more groups that are independently $C_1$-$C_4$ alkyl, $C_1$-$C_4$ alkoxy, halogen, $CF_3$ or $OCF_3$.

Still other preferred compounds of Embodiment 13 include those of embodiment 14, i.e., compounds of Embodiment 13 where $R_1$ is phenyl, thienyl, furanyl, pyridyl, pyrimidyl, pyrazinyl, triazolyl, imidazolyl, oxazolyl, benzofuranyl, each of which is unsubstituted or substituted with 1, 2, 3, 4, or 5 groups that are independently $C_1$-$C_6$ alkyl, halogen, $C_1$-$C_6$ alkoxy, OH, CN, $CO_2H$, heteroaryl selected from pyridyl, pyrimidyl, pyrazinyl, indolyl, thienyl, furanyl, pyrrolyl, and benzimidazolyl, heterocycloalkyl selected from piperidinyl, pyrrolidinyl, piperazinyl, morpholinyl, and S,S-dioxomorpholinyl, phenyl, or naphthyl, wherein the heteroaryl, heterocycloalkyl, phenyl and naphthyl groups are optionally substituted with 1 or more groups that are independently selected from $C_1$-$C_4$ alkyl, $C_1$-$C_4$ alkoxy, halogen, OH, OH, $CF_3$, and $OCF_3$, $CF_3$, $OCF_3$, —OC(O)—$C_1$-$C_4$ alkyl, $C_1$-$C_4$ alkoxycarbonyl, or $C_1$-$C_4$ alkanoyl.

Still other preferred compounds of Embodiment 13 include those of embodiment 15, i.e., compounds of Embodiment 13 where $R_1$ is phenyl, thienyl, pyridyl, pyrimidyl, pyrazinyl, triazolyl, imidazolyl, or benzofuranyl, each of which is unsubstituted or substituted with 1, 2, or 3 groups that are independently $C_1$-$C_6$ alkyl, halogen, $C_1$-$C_6$ alkoxy, OH, —C(O)$R_{10}$, $NR_6R_7$, —($C_1$-$C_4$ alkyl)-$NR_6R_7$, or —C(O)$NR_6R_7$, wherein each $R_6$ and $R_7$ is independently H, $C_1$-$C_6$ alkyl, $C_1$-$C_4$ alkoxyalkyl, $C_1$-$C_6$ alkoxycarbonyl, wherein the alkyl portion of each is unsubstituted or substituted with 1, or 2 groups that are independently halogen, OH, $CF_3$, $OCF_3$, $NH_2$, NH($C_1$-$C_6$ alkyl) or N($C_1$-$C_6$ alkyl)($C_1$-$C_6$ alkyl);

$R_{10}$ is phenyl, naphthyl, pyridyl, quinolinyl, pyrimidyl, furanyl, indolyl, or $C_3$-$C_8$ cycloalkyl, each of which is optionally substituted with halogen, $C_1$-$C_6$ alkyl, $C_1$-$C_6$ alkoxy, OH, $CO_2H$, CN, $NO_2$, $C_1$-$C_4$ haloalkyl, or $C_1$-$C_4$ haloalkoxy;

wherein the heterocycloalkyl and the cycloalkyl portions of $R_1$ and $R_{10}$ are further optionally substituted with =O, =N—OH, or =N—$OCH_3$.

Embodiment 16 includes compounds of Embodiments 14 and 15 wherein $R_4$ and $R_5$ and the nitrogen to which they are attached form a piperazinyl, morpholinyl, piperidinyl, imidazolidinyl, or pyrrolidinyl ring, each of which is unsubstituted or substituted with 1 or more groups that are independently $C_1$-$C_4$ alkyl, $C_1$-$C_4$ alkoxy, halogen, phenyl $C_1$-$C_2$ alkyl, $C_1$-$C_6$ alkanoyl, OH, pyridyl, pyrimidyl $C_1$-$C_2$ alkyl, phenyl, —$OCH_2CH_2O$—, or —$OCH_2O$—; and $R_2$ and $R_3$ are both H.

Other preferred compounds of Embodiment 16 include those of embodiment 16A, i.e., compounds of Embodiment 16 where $R_4$ and $R_5$ and the nitrogen to which they are attached form a piperazinyl, morpholinyl, piperidinyl, or pyrrolidinyl ring, each of which is substituted with 1 or more groups that are independently $C_1$-$C_4$ alkyl, $C_1$-$C_4$ alkoxy, halogen, phenyl $C_1$-$C_2$ alkyl, $C_1$-$C_6$ alkanoyl, OH, pyridyl, pyrimidyl $C_1$-$C_2$ alkyl, phenyl, —$OCH_2CH_2O$—, or —$OCH_2O$—.

Embodiment 16B includes compounds of embodiments 16 and 16A wherein $R_1$ is phenyl, which is unsubstituted or substituted with 1, 2, or 3 groups that are independently $C_1$-$C_6$ alkyl, halogen, $C_1$-$C_6$ alkoxy, OH, —C(O)$R_{10}$, $NR_6R_7$, —($C_1$-$C_4$ alkyl)-$NR_6R_7$, or —C(O)$NR_6R_7$, wherein each $R_6$ and $R_7$ is independently H, $C_1$-$C_6$ alkyl, $C_1$-$C_4$ alkoxycarbonyl, wherein the alkyl portion of each is unsubstituted or substituted with 1, or 2 groups that are independently halogen, OH, $NH_2$, NH($C_1$-$C_6$ alkyl) or N($C_1$-$C_6$ alkyl)($C_1$-$C_6$ alkyl); and $R_{10}$ is phenyl, pyridyl, or furanyl, each of which is optionally substituted with halogen, $C_1$-$C_6$ alkyl, $C_1$-$C_6$ alkoxy, OH, $CO_2H$, CN, $NO_2$, $CF_3$, or $OCF_3$.

Embodiment 16C includes compounds of embodiments 16 and 16A wherein $R_1$ is thienyl, triazolyl, imidazolyl, or benzofuranyl, each of which is unsubstituted or substituted with 1, 2, or 3 groups that are independently $C_1$-$C_6$ alkyl, halogen, $C_1$-$C_6$ alkoxy, OH, —C(O)$R_{10}$, $NR_6R_7$, —($C_1$-$C_4$ alkyl)-$NR_6R_7$, or —C(O)$NR_6R_7$, wherein each $R_6$ and $R_7$ is independently H, $C_1$-$C_6$ alkyl, $C_1$-$C_4$ alkoxycarbonyl, wherein the alkyl portion of each is unsubstituted or substituted with 1, or 2 groups that are independently halogen, OH, $NH_2$, NH($C_1$-$C_6$ alkyl) or N($C_1$-$C_6$ alkyl)($C_1$-$C_6$ alkyl); and $R_{10}$ is phenyl, pyridyl, or furanyl, each of which is optionally substituted with halogen, $C_1$-$C_6$ alkyl, $C_1$-$C_6$ alkoxy, OH, $CO_2H$, CN, $NO_2$, $CF_3$, or $OCF_3$.

Embodiment 16D includes compounds of embodiments 16 and 16A wherein $R_1$ is pyridyl, pyrimidyl, or pyrazinyl, each of which is unsubstituted or substituted with 1, 2, or 3 groups that are independently $C_1$-$C_6$ alkyl, halogen, $C_1$-$C_6$ alkoxy, OH, —C(O)$R_{10}$, $NR_6R_7$, —($C_1$-$C_4$ alkyl)-$NR_6R_7$, or —C(O)$NR_6R_7$, wherein each $R_6$ and $R_7$ is independently H, $C_1$-$C_6$ alkyl, $C_1$-$C_4$ alkoxycarbonyl, wherein the alkyl portion of each is unsubstituted or substituted with 1, or 2 groups that are independently halogen, OH, $NH_2$, NH($C_1$-$C_6$ alkyl) or N($C_1$-$C_6$ alkyl)($C_1$-$C_6$ alkyl); and $R_{10}$ is phenyl, pyridyl, or furanyl, each of which is optionally substituted with halogen, $C_1$-$C_6$ alkyl, $C_1$-$C_6$ alkoxy, OH, $CO_2H$, CN, $NO_2$, $CF_3$, or $OCF_3$.

Embodiment 16E includes compounds of embodiments 16, 16A, 16B, 16C, and 16D wherein Z is a bond.

Embodiment 16E includes compounds of embodiments 16, 16A, 16B, 16C, and 16D wherein Z is —$CH_2$—.

Embodiment 16G includes compounds of embodiments 16, 16A, 16B, 16C, and 16D wherein Z is —NH—.

Embodiment 16H includes compounds of embodiments 16, 16A, 16B, 16C, and 16D wherein Z is —S— or —$SO_2$—.

Embodiment 16I includes compounds of embodiments 16, 16A, 16B, 16C, and 16D wherein Z is —$SO_2$NH—, or —$SO_2$N($C_1$-$C_4$ alkyl)-.

In still another aspect, the invention provides compounds according to embodiments 5, 16, and 16A-16I, wherein $R_{21}$ is H.

In yet still another aspect, the invention provides compounds according to embodiments 5, 16, and 16A-16I, wherein $R_{21}$ is CN.

In still yet another aspect, the invention provides compounds according to embodiments 5, 16, and 16A-16I, wherein $R_{21}$ is amino, monoalkylamino, or dialkylamino.

In yet another aspect, the invention provides compounds of embodiments 5, 16, and 16A-16I, wherein $R_{21}$ is OH.

In still another aspect, the invention provides compounds of embodiments 5, 16, and 16A-16I, wherein $R_{21}$ is phenyl.

In still another aspect, the invention provides compounds of embodiments 5, 16, and 16A-16I, wherein $R_{21}$ is pyridyl.

In still another aspect, the invention provides compounds of embodiments 5, 16, and 16A-16I, wherein $R_{21}$ is halogen.

In yet another aspect, the invention provides compounds of embodiments 5, 16, and 16A-16I, wherein $R_{21}$ is phenyl, which is substituted with 1-5 groups that are independently $C_1$-$C_6$ alkyl, $C_1$-$C_6$ alkoxy, halogen, OH, hydroxyl $C_1$-$C_4$ alkyl, haloalkyl (in one aspect, $CF_3$), or haloalkoxy (in one aspect, $OCF_3$)).

In yet still another aspect, the invention provides compounds of embodiments 5, 16, and 16A-16I, wherein $R_{21}$ is pyridyl, or pyrimidyl, each of which is optionally substituted with 1-5 groups that are independently $C_1$-$C_6$ alkyl, $C_1$-$C_6$ alkoxy, halogen, OH, hydroxyl $C_1$-$C_4$ alkyl, haloalkyl (in one aspect, $CF_3$), or haloalkoxy (in one aspect, $OCF_3$)).

In yet still another aspect, the invention provides compounds of embodiments 5, 16, and 16A-16I, wherein $R_{21}$ is indolyl or (iso)quinolinyl, each of which is optionally substituted with 1-5 groups that are independently $C_1$-$C_6$ alkyl, $C_1$-$C_6$ alkoxy, halogen, OH, hydroxyl $C_1$-$C_4$ alkyl, haloalkyl (in one aspect, $CF_3$), or haloalkoxy (in one aspect, $OCF_3$)).

In still another aspect, the invention provides compounds of embodiments 5, 16, and 16A-16I, wherein $R_{21}$ is $C_1$-$C_6$ alkyl, $C_2$-$C_6$ alkynyl, or $C_2$-$C_6$ alkenyl.

In still yet another aspect, the invention provides compounds of embodiments 5, 16, and 16A-16I, wherein $R_{21}$ is —C(O)$NH_2$, —C(O)NH($C_1$-$C_6$ alkyl), or —C(O)N($C_1$-$C_6$ alkyl) ($C_1$-$C_6$ alkyl).

Still other preferred compounds of Embodiment 5 include those of embodiment 17, i.e., compounds of Embodiment 5 where $R_1$ is halogen, $C_1$-$C_6$ alkyl, $C_2$-$C_6$ alkynyl, $C_2$-$C_6$ alkenyl, each of which is unsubstituted or substituted with 1, 2, or 3 groups that are independently $C_1$-$C_6$ alkyl, halogen, $C_1$-$C_6$ alkoxy, OH, CN, $CO_2H$, heteroaryl selected from pyridyl, pyrimidyl, pyrazinyl, indolyl, thienyl, furanyl, pyrrolyl, and benzimidazolyl, heterocycloalkyl selected from piperidinyl, pyrrolidinyl, piperazinyl, morpholinyl, and S,S-dioxomorpholinyl, phenyl, or naphthyl, wherein the heteroaryl, heterocycloalkyl, phenyl and naphthyl groups are optionally substituted with 1 or more groups that are independently selected from $C_1$-$C_4$ alkyl, $C_1$-$C_4$ alkoxy, halogen, OH, OH, $CF_3$, and $OCF_3$, $CF_3$, $OCF_3$, —OC(O)—$C_1$-$C_6$ alkyl, $C_1$-$C_6$ alkoxycarbonyl, $C_1$-$C_6$ alkanoyl, —C(O)$R_{10}$, $NR_6R_7$, —($C_1$-$C_4$ alkyl)-$NR_6R_7$, or —C(O)$NR_6R_7$, wherein each $R_6$ and $R_7$ is independently H, $C_1$-$C_6$ alkyl, $C_1$-$C_4$ alkoxyalkyl, $C_1$-$C_6$ alkoxycarbonyl, wherein the alkyl portion of each is unsubstituted or substituted with 1, 2, or 3, groups that are independently halogen, OH, $C_1$-$C_4$ haloalkyl, $C_1$-$C_4$ haloalkoxy, $NH_2$, NH($C_1$-$C_6$ alkyl) or N($C_1$-$C_6$ alkyl) ($C_1$-$C_6$ alkyl);

$R_{10}$ is $C_2$-$C_6$ alkenyl, $C_2$-$C_6$ alkynyl, phenyl, naphthyl, pyridyl, quinolinyl, pyrimidyl, furanyl, indolyl, $C_3$-$C_8$ cycloalkyl, wherein the cyclic portions are optionally substituted with halogen, $C_1$-$C_6$ alkyl, $C_1$-$C_6$ alkoxy, OH, $CO_2H$, CN, $NO_2$, $C_1$-$C_4$ haloalkyl, or $C_1$-$C_4$ haloalkoxy;

wherein the cycloalkyl portion of $R_{10}$ is further optionally substituted with =O, =N-OH, or =N—$OCH_3$.

Other preferred compounds of Embodiment 17 include those of embodiment 18, i.e., compounds of Embodiment 17 where $R_4$ and $R_5$ and the nitrogen to which they are attached form a piperazinyl, morpholinyl, piperidinyl, thiomorpholinyl, imidazolidinyl, S,S,-dioxothiomorpholinyl, piperidinyl, pyrrolidinyl, ring, which is unsubstituted or substituted with 1 or more groups that are independently $C_1$-$C_6$ alkyl, $C_1$-$C_6$ alkoxy, halogen, phenyl $C_1$-$C_6$ alkyl, naphthyl $C_1$-$C_6$ alkyl, $C_1$-$C_6$ alkanoyl, OH, =O, pyridyl, pyrimidyl, pyrazinyl, pyrimidyl $C_1$-$C_6$ alkyl, pyrazinyl $C_1$-$C_6$ alkyl, phenyl, naphthyl, —$OCH_2CH_2O$—, or —$OCH_2O$—, wherein the pyridyl, pyrimidyl, pyrazinyl, pyrimidyl $C_1$-$C_6$ alkyl, phenyl and naphthyl groups are unsubstituted or substituted with 1 or more groups that are independently $C_1$-$C_4$ alkyl, $C_1$-$C_4$ alkoxy, halogen, $CF_3$ or $OCF_3$.

Other preferred compounds of Embodiment 18 include those of embodiment 19, i.e., compounds of Embodiment 18 where $R_1$ is halogen.

Other preferred compounds of Embodiment 18 include those of embodiment 20, i.e., compounds of Embodiment 18 where $R_1$ is $C_1$-$C_6$ alkyl, $C_2$-$C_6$ alkynyl, $C_2$-$C_6$ alkenyl, each of which is unsubstituted or substituted with 1, 2, or 3 groups that are independently $C_1$-$C_6$ alkyl, halogen, $C_1$-$C_6$ alkoxy, OH, CN, $CO_2H$, $CF_3$, $OCF_3$, —OC(O)—$C_1$-$C_6$ alkyl, $C_1$-$C_6$ alkoxycarbonyl, $C_1$-$C_6$ alkanoyl, —C(O)$R_{10}$, $NR_6R_7$, —($C_1$-$C_4$ alkyl)-$NR_6R_7$, —C(O)$NR_6R_7$, pyridyl, pyrrolyl, piperidinyl, pyrrolidinyl, piperazinyl morpholinyl, or phenyl, wherein the cyclic groups are optionally substituted with 1 or more groups that are independently selected from $C_1$-$C_4$ alkyl, $C_1$-$C_4$ alkoxy, halogen, OH, OH, $CF_3$, and $OCF_3$, wherein each $R_6$ and $R_7$ is independently H, $C_1$-$C_6$ alkyl, $C_1$-$C_4$ alkoxyalkyl, $C_1$-$C_6$ alkoxycarbonyl, wherein the alkyl portion of each is unsubstituted or substituted with 1, 2, or 3, groups that are independently halogen, OH, $C_1$-$C_4$ haloalkyl, $C_1$-$C_4$ haloalkoxy, $NH_2$, NH($C_1$-$C_6$ alkyl) or N($C_1$-$C_6$ alkyl) ($C_1$-$C_6$ alkyl);

$R_{10}$ is phenyl or pyridyl, each of which is optionally substituted with halogen, $C_1$-$C_6$ alkyl, $C_1$-$C_6$ alkoxy, OH, $CO_2H$, CN, $NO_2$, $CF_3$ or $OCF_3$.

Other preferred compounds of Embodiment 20 include those of embodiment 21, i.e., compounds of Embodiment 20 where $R_4$ and $R_5$ and the nitrogen to which they are attached form a piperazinyl, morpholinyl, piperidinyl, piperidinyl, or pyrrolidinyl ring, each of which is unsubstituted or substituted with 1 or more groups that are independently $C_1$-$C_6$ alkyl, $C_1$-$C_6$ alkoxy, halogen, phenyl $C_1$-$C_6$ alkyl, naphthyl $C_1$-$C_6$ alkyl, $C_1$-$C_6$ alkanoyl, OH, =O, pyridyl, pyrimidyl, pyrazinyl, pyrimidyl $C_1$-$C_6$ alkyl, pyrazinyl $C_1$-$C_6$ alkyl, phenyl, naphthyl, —$OCH_2CH_2O$—, or —$OCH_2O$—.

Other preferred compounds of Embodiment 21 include those of embodiment 22, i.e., compounds of Embodiment 21 where $R_1$ is $C_2$-$C_6$ alkynyl substituted with 1, 2, or 3 groups that are independently $C_1$-$C_6$ alkyl, halogen, $C_1$-$C_6$ alkoxy, OH, CN, $CO_2H$, $CF_3$, $OCF_3$, —OC(O)—$C_1$-$C_6$ alkyl, $C_1$-$C_6$ alkoxycarbonyl, $C_1$-$C_6$ alkanoyl, —C(O)$R_{10}$, $NR_6R_7$, —($C_1$-$C_4$ alkyl)-$NR_6R_7$, —C(O)$NR_6R_7$, pyridyl, piperidinyl, or phenyl, wherein the phenyl is optionally substituted with 1 or more groups that are independently selected from $C_1$-$C_4$ alkyl, $C_1$-$C_4$ alkoxy, halogen, OH, OH, $CF_3$, and $OCF_3$, wherein each $R_6$ and $R_7$ is independently H, $C_1$-$C_6$ alkyl, $C_1$-$C_6$ alkoxycarbonyl, wherein the alkyl portion of each is unsubstituted or substituted with 1, or 2 groups that are independently halogen, OH, $CF_3$, $OCF_3$, $NH_2$, $NH(C_1$-$C_6$ alkyl) or $N(C_1$-$C_6$ alkyl) $(C_1$-$C_6$ alkyl)

Other preferred compounds of Embodiment 21 include those of embodiment 23, i.e., compounds of Embodiment 21 where $R_1$ is $C_1$-$C_6$ alkyl substituted with 1, 2, or 3 groups that are independently $C_1$-$C_6$ alkyl, halogen, $C_1$-$C_6$ alkoxy, OH, CN, $CO_2H$, $CF_3$, $OCF_3$, —OC(O)—$C_1$-$C_6$ alkyl, $C_1$-$C_6$ alkoxycarbonyl, $C_1$-$C_6$ alkanoyl, —C(O)$R_{10}$, $NR_6R_7$, —($C_1$-$C_4$ alkyl)-$NR_6R_7$, —C(O)$NR_6R_7$, pyridyl, piperidinyl, or phenyl, wherein the phenyl is optionally substituted with 1 or more groups that are independently selected from $C_1$-$C_4$ alkyl, $C_1$-$C_4$ alkoxy, halogen, OH, OH, $CF_3$, and $OCF_3$, wherein each $R_6$ and $R_7$ is independently H, $C_1$-$C_6$ alkyl, $C_1$-$C_6$ alkoxycarbonyl, wherein the alkyl portion of each is unsubstituted or substituted with 1, or 2 groups that are independently halogen, OH, $CF_3$, $OCF_3$, $NH_2$, $NH(C_1$-$C_6$ alkyl) or $N(C_1$-$C_6$ alkyl) $(C_1$-$C_6$ alkyl)

Other preferred compounds of Embodiment 21 include those of embodiment 24, i.e., compounds of Embodiment 21 where $R_1$ is $C_1$-$C_6$ alkenyl substituted with 1, 2, or 3 groups that are independently $C_1$-$C_6$ alkyl, halogen, $C_1$-$C_6$ alkoxy, OH, CN, $CO_2H$, $CF_3$, $OCF_3$, —OC(O)—$C_1$-$C_6$ alkyl, $C_1$-$C_6$ alkoxycarbonyl, $C_1$-$C_6$ alkanoyl, —C(O)$R_{10}$, $NR_6R_7$, —($C_1$-$C_4$ alkyl) —$NR_6R_7$, —C(O)$NR_6R_7$, pyridyl, piperidinyl, or phenyl, wherein the phenyl is optionally substituted with 1 or more groups that are independently selected from $C_1$-$C_4$ alkyl, $C_1$-$C_4$ alkoxy, halogen, OH, OH, $CF_3$, and $OCF_3$, wherein each $R_6$ and $R_7$ is independently H, $C_1$-$C_6$ alkyl, $C_1$-$C_6$ alkoxycarbonyl, wherein the alkyl portion of each is unsubstituted or substituted with 1, or 2 groups that are independently halogen, OH, $CF_3$, $OCF_3$, $NH_2$, $NH(C_1$-$C_6$ alkyl) or $N(C_1$-$C_6$ alkyl) $(C_1$-$C_6$ alkyl)

Embodiment 24A includes compounds of embodiments 19, 20, 21, 22, 23, and 24, wherein Z is a bond.

Embodiment 24B includes compounds of embodiments 20, 21, 22, 23, and 24, wherein Z is —$CH_2$—.

Embodiment 24C includes compounds of embodiments 20, 21, 22, 23, and 24, wherein Z is —NH—.

Embodiment 24D includes compounds of embodiments 20, 21, 22, 23, and 24, wherein Z is —S— or —$SO_2$—.

Embodiment 24E includes compounds of embodiments 20, 21, 22, 23, and 24, wherein Z is —$N(C_1$-$C_4$ alkyl)-. In another aspect, Z is —$N(C_1$-$C_2$ alkyl)-. In still another aspect, Z is —$N(C_2$-$C_3$ alkyl)-.

Embodiment 24F includes compounds of embodiments 20, 21, 22, 23, and 24, wherein Z is —$SO_2NH$—, or —$SO_2N(C_1$-$C_4$ alkyl)-.

In still another aspect, the invention provides compounds according to embodiments 20, 21, 22, 23, 24, and 24A-24F, wherein $R_{21}$ is H.

In yet still another aspect, the invention provides compounds according to embodiments 20, 21, 22, 23, 24, and 24A-24F, wherein $R_{21}$ is CN.

In still yet another aspect, the invention provides compounds according to embodiments 20, 21, 22, 23, 24, and 24A-24F, wherein $R_{21}$ is amino, monoalkylamino, or dialkylamino.

In yet another aspect, the invention provides compounds of embodiments 20, 21, 22, 23, 24, and 24A-24F, wherein $R_{21}$ is OH.

In still another aspect, the invention provides compounds of embodiments 20, 21, 22, 23, 24, and 24A-24F, wherein $R_{21}$ is phenyl.

In still another aspect, the invention provides compounds of embodiments 20, 21, 22, 23, 24, and 24A-24F, wherein $R_{21}$ is pyridyl.

In still another aspect, the invention provides compounds of embodiments 20, 21, 22, 23, 24, and 24A-24F, wherein $R_{21}$ is halogen.

In yet another aspect, the invention provides compounds of embodiments 20, 21, 22, 23, 24, and 24A-24F, wherein $R_{21}$ is phenyl, which is substituted with 1-5 groups that are independently $C_1$-$C_6$ alkyl, $C_1$-$C_6$ alkoxy, halogen, OH, hydroxyl $C_1$-$C_4$ alkyl, haloalkyl (in one aspect, $CF_3$), or haloalkoxy (in one aspect, $OCF_3$)).

In yet still another aspect, the invention provides compounds of embodiments 20, 21, 22, 23, 24, and 24A-24F, wherein $R_{21}$ is pyridyl, or pyrimidyl, each of which is optionally substituted with 1-5 groups that are independently $C_1$-$C_6$ alkyl, $C_1$-$C_6$ alkoxy, halogen, OH, hydroxyl $C_1$-$C_4$ alkyl, haloalkyl (in one aspect, $CF_3$), or haloalkoxy (in one aspect, $OCF_3$)).

In yet still another aspect, the invention provides compounds of embodiments 20, 21, 22, 23, 24, and 24A-24F, wherein $R_{21}$ is indolyl or (iso)quinolinyl, each of which is optionally substituted with 1-5 groups that are independently $C_1$-$C_6$ alkyl, $C_1$-$C_6$ alkoxy, halogen, OH, hydroxyl $C_1$-$C_4$ alkyl, haloalkyl (in one aspect, $CF_3$), or haloalkoxy (in one aspect, $OCF_3$)).

In still another aspect, the invention provides compounds of embodiments 20, 21, 22, 23, 24, and 24A-24F, wherein $R_{21}$ is $C_1$-$C_6$ alkyl, $C_2$-$C_6$ alkynyl, or $C_2$-$C_6$ alkenyl.

In still yet another aspect, the invention provides compounds of embodiments 20, 21, 22, 23, 24, and 24A-24F, wherein $R_{21}$ is —C(O)$NH_2$, —C(O)$NH(C_1$-$C_6$ alkyl), or —C(O)$N(C_1$-$C_6$ alkyl) $(C_1$-$C_6$ alkyl).

Still other preferred compounds of Embodiment 17 include those of Embodiment 25, i.e., compounds of Embodiment 17 where $R_4$ and $R_5$ are independently H, $C_1$-$C_6$ alkyl, $C_1$-$C_4$ alkoxy $C_1$-$C_6$ alkyl, $C_3$-$C_8$ cycloalkyl, piperidinyl, pyrrolidinyl, morpholinyl, morpholinyl $C_1$-$C_6$ alkyl, piperidinyl $C_1$-$C_6$ alkyl, pyrrolidinyl $C_1$-$C_6$ alkyl, piperidinyl $C_2$-$C_6$ alkenyl, pyrrolidinyl $C_2$-$C_6$ alkenyl, morpholinyl $C_2$-$C_6$ alkenyl, piperidinyl $C_2$-$C_6$ alkynyl, pyrrolidinyl $C_2$-$C_6$ alkynyl, morpholinyl $C_2$-$C_6$ alkynyl, phenyl, furanyl, pyridyl, pyrazinyl $C_1$-$C_6$ alkyl, pyridyl $C_1$-$C_6$ alkyl, imidazolyl $C_1$-$C_6$ alkyl, furanyl $C_1$-$C_6$ alkyl, thienyl $C_1$-$C_6$ alkyl, phenyl $C_1$-$C_6$ alkyl, phenyl $C_2$-$C_6$ alkenyl, phenyl $C_2$-$C_6$ alkynyl, wherein the cyclic portion of each of the above is unsubstituted or substituted with one or more groups that are independently $C_1$-$C_6$ alkyl, $C_1$-$C_6$ alkoxy, halogen, —$SO_2$—($C_1$-$C_6$) alkyl, $C_1$-$C_4$ haloalkyl, $C_1$-$C_4$ haloalkoxy, $NO_2$, CN, OH, phenyl $C_1$-$C_6$ alkyl wherein the phenyl is optionally substituted with 1, 2, 3, 4, or 5 groups that are independently selected from $C_1$-$C_4$ alkyl, $C_1$-$C_4$ alkoxy, CN, halogen, OH, and alkanoyl, $C_1$-$C_6$ alkoxy $C_1$-$C_6$ alkyl, $C_1$-$C_6$ alkoxycarbonyl, $C_1$-$C_6$ alkanoyl, $NR_7R_8$, or —C(O)$NR_7R_8$, wherein $R_7$ and $R_8$ are independently H or $C_1$-$C_6$ alkyl, wherein the $C_1$-$C_6$ alkyl is optionally substituted with 1, 2, or 3 groups that are independently $C_1$-$C_6$ alkoxycarbonyl, halogen, $C_1$-$C_6$ alkoxy, $C_1$-$C_6$ alkanoyl, $NH_2$, $NH(C_1$-$C_6$ alkyl), $N(C_1$-$C_6$ alkyl) ($C_1$-$C_6$ alkyl) or $CO_2H$;

wherein the heterocycloalkyl and the cycloalkyl portions of $R_4$ and $R_5$ are further optionally substituted with =O, =N—OH, or =N—$OCH_3$.

Still other preferred compounds of Embodiment 25 include those of Embodiment 26, i.e., compounds of Embodiment 25 where $R_1$ is $C_1$-$C_6$ alkyl, $C_2$-$C_6$ alkynyl, $C_2$-$C_6$ alkenyl, each of which is unsubstituted or substituted with 1, 2, or 3 groups that are independently $C_1$-$C_6$ alkyl, halogen, $C_1$-$C_6$ alkoxy, OH, CN, $CO_2H$, $CF_3$, $OCF_3$, —OC(O)—$C_1$-$C_6$ alkyl, $C_1$-$C_6$ alkoxycarbonyl, $C_1$-$C_6$ alkanoyl, —C(O)$R_{10}$, $NR_6R_7$, —($C_1$-$C_4$ alkyl)-$NR_6R_7$, —C(O)$NR_6R_7$, pyridyl, piperidinyl, or phenyl, wherein the pyridyl, piperidinyl and phenyl groups are optionally substituted with 1 or more groups that are independently selected from $C_1$-$C_4$ alkyl, $C_1$-$C_4$ alkoxy, halogen, OH, OH, $CF_3$, and $OCF_3$, wherein each $R_6$ and $R_7$ is independently H, $C_1$-$C_6$ alkyl, $C_1$-$C_4$ alkoxyalkyl, $C_1$-$C_6$ alkoxycarbonyl, wherein the alkyl portion of each is unsubstituted or substituted with 1, 2, or 3, groups that are independently halogen, OH, $C_1$-$C_4$ haloalkyl, $C_1$-$C_4$ haloalkoxy, $NH_2$, $NH(C_1$-$C_6$ alkyl) or $N(C_1$-$C_6$ alkyl) ($C_1$-$C_6$ alkyl);

$R_{10}$ is phenyl or pyridyl, each of which is optionally substituted with halogen, $C_1$-$C_6$ alkyl, $C_1$-$C_6$ alkoxy, OH, $CO_2H$, CN, $NO_2$, $CF_3$ or $OCF_3$.

Still other preferred compounds of Embodiment 26 include those of Embodiment 27, i.e., compounds of Embodiment 26 where $R_4$ and $R_5$ are independently H, $C_1$-$C_6$ alkyl, $C_1$-$C_4$ alkoxy $C_1$-$C_6$ alkyl, piperidinyl, pyrrolidinyl, morpholinyl, morpholinyl $C_1$-$C_6$ alkyl, piperidinyl $C_1$-$C_6$ alkyl, pyrrolidinyl $C_1$-$C_6$ alkyl, phenyl, furanyl, pyridyl, pyrazinyl $C_1$-$C_6$ alkyl, pyridyl $C_1$-$C_6$ alkyl, imidazolyl $C_1$-$C_6$ alkyl, furanyl $C_1$-$C_6$ alkyl, thienyl $C_1$-$C_6$ alkyl, phenyl $C_1$-$C_6$ alkyl, wherein the cyclic portion of each of the above is unsubstituted or substituted with one or more groups that are independently $C_1$-$C_6$ alkyl, $C_1$-$C_6$ alkoxy, halogen, —$SO_2$—($C_1$-$C_6$) alkyl, $C_1$-$C_4$ haloalkyl, $C_1$-$C_4$ haloalkoxy, $NO_2$, CN, OH, phenyl $C_1$-$C_6$ alkyl wherein the phenyl is optionally substituted with 1, 2, 3, 4, or 5 groups that are independently selected from $C_1$-$C_4$ alkyl, $C_1$-$C_4$ alkoxy, CN, halogen, OH, and alkanoyl, $C_1$-$C_6$ alkoxy $C_1$-$C_6$ alkyl, $C_1$-$C_6$ alkoxycarbonyl, $C_1$-$C_6$ alkanoyl, $NR_7R_8$, or —C(O)$NR_7R_8$, wherein $R_7$ and $R_8$ are independently H or $C_1$-$C_6$ alkyl, wherein the $C_1$-$C_6$ alkyl is optionally substituted with 1, 2, or 3 groups that are independently $C_1$-$C_6$ alkoxycarbonyl, halogen, $C_1$-$C_6$ alkoxy, $C_1$-$C_6$ alkanoyl, $NH_2$, $NH(C_1$-$C_6$ alkyl), $N(C_1$-$C_6$ alkyl) ($C_1$-$C_6$ alkyl) or $CO_2H$;

wherein the heterocycloalkyl and the cycloalkyl portions of $R_4$ and $R_5$ are further optionally substituted with =O, =N—OH, or =N—$OCH_3$.

Still other preferred compounds of Embodiment 27 include those of Embodiment 28, i.e., compounds of Embodiment 27 where $R_1$ is $C_2$-$C_6$ alkynyl substituted with 1, 2, or 3 groups that are independently $C_1$-$C_6$ alkyl, halogen, $C_1$-$C_6$ alkoxy, OH, CN, $CO_2H$, $CF_3$, $OCF_3$, —OC(O)—$C_1$-$C_6$ alkyl, $C_1$-$C_6$ alkoxycarbonyl, $C_1$-$C_6$ alkanoyl, —C(O)$R_{10}$, $NR_6R_7$, —($C_1$-$C_4$ alkyl) —$NR_6R_7$, —C(O)$NR_6R_7$, pyridyl, piperidinyl, or phenyl, wherein the phenyl is optionally substituted with 1 or more groups that are independently selected from $C_1$-$C_4$ alkyl, $C_1$-$C_4$ alkoxy, halogen, OH, $CF_3$, and $OCF_3$, wherein each $R_6$ and $R_7$ is independently H, $C_1$-$C_6$ alkyl, $C_1$-$C_6$ alkoxycarbonyl, wherein the alkyl portion of each is unsubstituted or substituted with 1, or 2 groups that are independently halogen, OH, $CF_3$, $OCF_3$, $NH_2$, $NH(C_1$-$C_6$ alkyl) or $N(C_1$-$C_6$ alkyl) ($C_1$-$C_6$ alkyl).

Still other preferred compounds of Embodiment 27 include those of Embodiment 29, i.e., compounds of Embodiment 27 where $R_1$ is $C_1$-$C_6$ alkyl substituted with 1, 2, or 3 groups that are independently $C_1$-$C_6$ alkyl, halogen, $C_1$-$C_6$ alkoxy, OH, CN, $CO_2H$, $CF_3$, $OCF_3$, —OC(O)—$C_1$-$C_6$ alkyl, $C_1$-$C_6$ alkoxycarbonyl, $C_1$-$C_6$ alkanoyl, —C(O)$R_{10}$, $NR_6R_7$, —($C_1$-$C_4$ alkyl) —$NR_6R_7$, —C(O)$NR_6R_7$, pyridyl, piperidinyl, or phenyl, wherein the phenyl is optionally substituted with 1 or more groups that are independently selected from $C_1$-$C_4$ alkyl, $C_1$-$C_4$ alkoxy, halogen, OH, $CF_3$, and $OCF_3$, wherein each $R_6$ and $R_7$ is independently H, $C_1$-$C_6$ alkyl, $C_1$-$C_6$ alkoxycarbonyl, wherein the alkyl portion of each is unsubstituted or substituted with 1, or 2 groups that are independently halogen, OH, $CF_3$, $OCF_3$, $NH_2$, $NH(C_1$-$C_6$ alkyl) or $N(C_1$-$C_6$ alkyl) ($C_1$-$C_6$ alkyl).

Still other preferred compounds of Embodiment 27 include those of Embodiment 30, i.e., compounds of Embodiment 27 where $R_1$ is $C_1$-$C_6$ alkenyl substituted with 1, 2, or 3 groups that are independently $C_1$-$C_6$ alkyl, halogen, $C_1$-$C_6$ alkoxy, OH, CN, $CO_2H$, $CF_3$, $OCF_3$, —OC(O)—$C_1$-$C_6$ alkyl, $C_1$-$C_6$ alkoxycarbonyl, $C_1$-$C_6$ alkanoyl, —C(O)$R_{10}$, $NR_6R_7$, —($C_1$-$C_4$ alkyl)—$NR_6R_7$, —C(O)$NR_6R_7$, piperidinyl, piperidinyl, or phenyl, wherein the phenyl is optionally substituted with 1 or more groups that are independently selected from $C_1$-$C_4$ alkyl, $C_1$-$C_4$ alkoxy, halogen, OH, $CF_3$, and $OCF_3$, wherein each $R_6$ and $R_7$ is independently H, $C_1$-$C_6$ alkyl, $C_1$-$C_6$ alkoxycarbonyl, wherein the alkyl portion of each is unsubstituted or substituted with 1, or 2 groups that are independently halogen, OH, $CF_3$, $OCF_3$, $NH_2$, $NH(C_1$-$C_6$ alkyl) or $N(C_1$-$C_6$ alkyl) ($C_1$-$C_6$ alkyl).

Embodiment 30A includes compounds of embodiments 27, 28, and 29, wherein $R_2$ and $R_3$ are independently H or methyl. In another aspect, at least one of $R_2$ and $R_3$ is H.

Preferred compounds of Embodiment 30A include those of Embodiment 30B, i.e., compounds of Embodiment 30A where wherein $R_4$ is H, $C_1$-$C_6$ alkyl, or $C_1$-$C_4$ alkoxy $C_1$-$C_6$ alkyl.

Preferred compounds of Embodiment 30B include those of Embodiment 30C, i.e., compounds of Embodiment 30B where $R_5$ is piperidinyl, pyrrolidinyl, morpholinyl, phenyl, furanyl, or pyridyl, wherein the cyclic portion of each of the above is unsubstituted or substituted with one or more groups that are independently $C_1$-$C_4$ alkyl, $C_1$-$C_4$ alkoxy, halogen, —$SO_2$—($C_1$-$C_6$) alkyl, $CF_3$, $OCF_3$, $NO_2$, CN, OH, phenyl $C_1$-$C_4$ alkyl wherein the phenyl is optionally substituted with 1, 2, 3, 4, or 5 groups that are independently selected from $C_1$-$C_4$ alkyl, $C_1$-$C_4$ alkoxy, CN, halogen, OH, and alkanoyl, $C_1$-$C_6$ alkoxy $C_1$-$C_6$ alkyl, $C_1$-$C_6$ alkoxycarbonyl, $C_1$-$C_6$ alkanoyl, $NR_7R_8$, or —C(O)$NR_7R_8$,
  wherein $R_7$ and $R_8$ are independently H or $C_1$-$C_6$ alkyl,
    wherein the $C_1$-$C_6$ alkyl is optionally substituted with 1, 2, or 3 groups that are independently $C_1$-$C_6$ alkoxycarbonyl, halogen, $C_1$-$C_6$ alkoxy, $C_1$-$C_6$ alkanoyl, $NH_2$, NH($C_1$-$C_6$ alkyl), N($C_1$-$C_6$ alkyl)($C_1$-$C_6$ alkyl) or $CO_2H$;
  wherein the heterocycloalkyl and the cycloalkyl portions of $R_4$ and $R_5$ are further optionally substituted with =O, =N—OH, or =N—$OCH_3$.

Preferred compounds of Embodiment 30B include those of Embodiment 30D, i.e., compounds of Embodiment 30B where
$R_5$ is morpholinyl $C_1$-$C_4$ alkyl, piperidinyl $C_1$-$C_4$ alkyl, pyrrolidinyl $C_1$-$C_4$ alkyl, pyrazinyl $C_1$-$C_4$ alkyl, pyridyl $C_1$-$C_4$ alkyl, imidazolyl $C_1$-$C_4$ alkyl, furanyl $C_1$-$C_4$ alkyl, thienyl $C_1$-$C_4$ alkyl, or phenyl $C_1$-$C_4$ alkyl, wherein the cyclic portion of each of the above is unsubstituted or substituted with one or more groups that are independently $C_1$-$C_4$ alkyl, $C_1$-$C_4$ alkoxy, halogen, —$SO_2$—($C_1$-$C_6$) alkyl, $CF_3$, $OCF_3$, $NO_2$, CN, OH, phenyl $C_1$-$C_4$ alkyl wherein the phenyl is optionally substituted with 1, 2, 3, 4, or 5 groups that are independently selected from $C_1$-$C_4$ alkyl, $C_1$-$C_4$ alkoxy, CN, halogen, OH, and alkanoyl, $C_1$-$C_6$ alkoxy $C_1$-$C_6$ alkyl, $C_1$-$C_6$ alkoxycarbonyl, $C_1$-$C_6$ alkanoyl, $NR_7R_8$, or —C(O)$NR_7R_8$,
  wherein $R_7$ and $R_8$ are independently H or $C_1$-$C_6$ alkyl,
    wherein the $C_1$-$C_6$ alkyl is optionally substituted with 1, 2, or 3 groups that are independently $C_1$-$C_6$ alkoxycarbonyl, halogen, $C_1$-$C_6$ alkoxy, $C_1$-$C_6$ alkanoyl, $NH_2$, NH($C_1$-$C_6$ alkyl), N($C_1$-$C_6$ alkyl)($C_1$-$C_6$ alkyl) or $CO_2H$;
  wherein the heterocycloalkyl and the cycloalkyl portions of $R_4$ and $R_5$ are further optionally substituted with =O, =N—OH, or =N—$OCH_3$.

Embodiment 30E includes compounds of embodiments 30C and 30D, wherein Z is a bond.

Embodiment 30F includes compounds of embodiments 30C and 30D, wherein Z is —$CH_2$—.

Embodiment 30G includes compounds of embodiments 30C and 30D, wherein Z is —NH—.

Embodiment 30H includes compounds of embodiments 30C and 30D, wherein Z is —S— or —$SO_2$—.

Embodiment 30I includes compounds of embodiments 30C and 30D, wherein Z is —N($C_1$-$C_4$ alkyl)-. In another aspect, Z is —N($C_1$-$C_2$ alkyl)-. In still another aspect, Z is —N($C_2$-$C_3$ alkyl)-.

30J. A compound according to either embodiment 30C or 30D, wherein Z is —$SO_2$NH—, or —$SO_2$N($C_1$-$C_4$ alkyl)-.

In still another aspect, the invention provides compounds according to embodiments 27, 28, 29, 30, and 30A-30I, wherein $R_{21}$ is H.

In yet still another aspect, the invention provides compounds according to embodiments 27, 28, 29, 30, and 30A-30I, wherein $R_{21}$ is CN.

In still yet another aspect, the invention provides compounds according to embodiments 27, 28, 29, 30, and 30A-30I, wherein $R_{21}$ is amino, monoalkylamino, or dialkylamino.

In yet another aspect, the invention provides compounds of embodiments 27, 28, 29, 30, and 30A-30I, wherein $R_{21}$ is OH.

In still another aspect, the invention provides compounds of embodiments 27, 28, 29, 30, and 30A-30I, wherein $R_{21}$ is phenyl.

In still another aspect, the invention provides compounds of embodiments 27, 28, 29, 30, and 30A-30I, wherein $R_{21}$ is pyridyl.

In still another aspect, the invention provides compounds of embodiments 27, 28, 29, 30, and 30A-30I, wherein $R_{21}$ is halogen.

In yet another aspect, the invention provides compounds of embodiments 27, 28, 29, 30, and 30A-30I, wherein $R_{21}$ is phenyl, which is substituted with 1-5 groups that are independently $C_1$-$C_6$ alkyl, $C_1$-$C_6$ alkoxy, halogen, OH, hydroxyl $C_1$-$C_4$ alkyl, haloalkyl (in one aspect, $CF_3$), or haloalkoxy (in one aspect, $OCF_3$)).

In yet still another aspect, the invention provides compounds of embodiments 27, 28, 29, 30, and 30A-30I, wherein $R_{21}$ is pyridyl or pyrimidyl, each of which is optionally substituted with 1-5 groups that are independently $C_1$-$C_6$ alkyl, $C_1$-$C_6$ alkoxy, halogen, OH, hydroxyl $C_1$-$C_4$ alkyl, haloalkyl (in one aspect, $CF_3$), or haloalkoxy (in one aspect, $OCF_3$)).

In yet still another aspect, the invention provides compounds of embodiments 27, 28, 29, 30, and 30A-30I, wherein $R_{21}$ is indolyl or (iso)quinolinyl, each of which is optionally substituted with 1-5 groups that are independently $C_1$-$C_6$ alkyl, $C_1$-$C_6$ alkoxy, halogen, OH, hydroxyl $C_1$-$C_4$ alkyl, haloalkyl (in one aspect, $CF_3$), or haloalkoxy (in one aspect, $OCF_3$)).

In still another aspect, the invention provides compounds of embodiments 27, 28, 29, 30, and 30A-30I, wherein $R_{21}$ is $C_1$-$C_6$ alkyl, $C_2$-$C_6$ alkynyl, or $C_2$-$C_6$ alkenyl.

In still yet another aspect, the invention provides compounds of embodiments 27, 28, 29, 30, and 30A-30I, wherein $R_{21}$ is —C(O)$NH_2$, —C(O)NH($C_1$-$C_6$ alkyl), or —C(O)N($C_1$-$C_6$ alkyl)($C_1$-$C_6$ alkyl).

Other preferred compounds of Embodiment 17 include those of Embodiment 31, i.e., compounds of Embodiment 17 where
$R_4$ and $R_5$ are independently H, $C_1$-$C_6$ alkyl, or $C_3$-$C_6$ cycloalkyl, wherein the cycloalkyl is unsubstituted or substituted with one or more groups that are independently $C_1$-$C_6$ alkyl, $C_1$-$C_6$ alkoxy, halogen, —$SO_2$—($C_1$-$C_6$) alkyl, $C_1$-$C_4$ haloalkyl, $C_1$-$C_4$ haloalkoxy, $NO_2$, CN, OH, phenyl $C_1$-$C_6$ alkyl wherein the phenyl is optionally substituted with 1, 2, 3, 4, or 5 groups that are independently selected from $C_1$-$C_4$ alkyl, $C_1$-$C_4$ alkoxy, CN, halogen, OH, and alkanoyl, $C_1$-$C_6$ alkoxy $C_1$-$C_6$ alkyl, $C_1$-$C_6$ alkoxycarbonyl, $C_1$-$C_6$ alkanoyl, $NR_7R_8$, or —C(O)$NR_7R_8$,
  wherein $R_7$ and $R_8$ are independently H or $C_1$-$C_6$ alkyl,
    wherein the $C_1$-$C_6$ alkyl is optionally substituted with 1, 2, or 3 groups that are independently $C_1$-$C_6$ alkoxycarbonyl, halogen, $C_1$-$C_6$ alkoxy, $C_1$-$C_6$ alkanoyl, $NH_2$, NH($C_1$-$C_6$ alkyl), N($C_1$-$C_6$ alkyl)($C_1$-$C_6$ alkyl) or $CO_2H$;
  wherein the cycloalkyl portion of $R_4$ and $R_5$ is further optionally substituted with =O, =N—OH, or =N—$OCH_3$.

Other preferred compounds of Embodiment 31 include those of Embodiment 32, i.e., compounds of Embodiment 31 where
$R_1$ is $C_1$-$C_6$ alkyl, $C_2$-$C_6$ alkynyl, $C_2$-$C_6$ alkenyl, each of which is unsubstituted or substituted with 1, 2, or 3 groups that are independently $C_1$-$C_6$ alkyl, halogen, $C_1$-$C_6$ alkoxy, OH, CN, $CO_2H$, $CF_3$, $OCF_3$, —OC(O)—$C_1$-$C_6$ alkyl, $C_1$-$C_6$ alkoxycarbonyl, $C_1$-$C_6$ alkanoyl, —C(O)$R_{10}$, $NR_6R_7$, —($C_1$-$C_4$ alkyl)-$NR_6R_7$, —C(O)$NR_6R_7$, pyridyl, piperidinyl, or phenyl, wherein the phenyl is optionally substituted with 1 or more groups that are independently selected from $C_1$-$C_4$ alkyl, $C_1$-$C_4$ alkoxy, halogen, OH, $CF_3$, and $OCF_3$, wherein each $R_6$ and $R_7$ is independently H, $C_1$-$C_6$ alkyl, $C_1$-$C_4$ alkoxyalkyl, $C_1$-$C_6$ alkoxycarbonyl, wherein the alkyl portion of each is unsubstituted or substituted with 1, 2, or 3, groups that are independently halogen, OH, $C_1$-$C_4$ haloalkyl, $C_1$-$C_4$ haloalkoxy, $NH_2$, $NH(C_1$-$C_6$ alkyl) or $N(C_1$-$C_6$ alkyl) ($C_1$-$C_6$ alkyl);

$R_{10}$ is phenyl or pyridyl, each of which is optionally substituted with halogen, $C_1$-$C_6$ alkyl, $C_1$-$C_6$ alkoxy, OH, $CO_2H$, CN, $NO_2$, $CF_3$ or $OCF_3$.

Other preferred compounds of Embodiment 31 include those of Embodiment 33, i.e., compounds of Embodiment 31 where $R_1$ is $C_2$-$C_6$ alkynyl substituted with 1, 2, or 3 groups that are independently $C_1$-$C_6$ alkyl, halogen, $C_1$-$C_6$ alkoxy, OH, CN, $CO_2H$, $CF_3$, $OCF_3$, —OC(O)—$C_1$-$C_6$ alkyl, $C_1$-$C_6$ alkoxycarbonyl, $C_1$-$C_6$ alkanoyl, —C(O)$R_{10}$, $NR_6R_7$, —($C_1$-$C_4$ alkyl) —$NR_6R_7$, —C(O)$NR_6R_7$, pyridyl, piperidinyl, or phenyl, wherein the phenyl is optionally substituted with 1 or more groups that are independently selected from $C_1$-$C_4$ alkyl, $C_1$-$C_4$ alkoxy, halogen, OH, $CF_3$, and $OCF_3$, wherein each $R_6$ and $R_7$ is independently H, $C_1$-$C_6$ alkyl, $C_1$-$C_6$ alkoxycarbonyl, wherein the alkyl portion of each is unsubstituted or substituted with 1, or 2 groups that are independently halogen, OH, $CF_3$, $OCF_3$, $NH_2$, $NH(C_1$-$C_6$ alkyl) or $N(C_1$-$C_6$ alkyl) ($C_1$-$C_6$ alkyl)

Other preferred compounds of Embodiment 31 include those of Embodiment 34, i.e., compounds of Embodiment 31 where $R_1$ is $C_1$-$C_6$ alkyl substituted with 1, 2, or 3 groups that are independently $C_1$-$C_6$ alkyl, halogen, $C_1$-$C_6$ alkoxy, OH, CN, $CO_2H$, $CF_3$, $OCF_3$, —OC(O)—$C_1$-$C_6$ alkyl, $C_1$-$C_6$ alkoxycarbonyl, $C_1$-$C_6$ alkanoyl, —C(O)$R_{10}$, $NR_6R_7$, —($C_1$-$C_4$ alkyl) —$NR_6R_7$, —C(O)$NR_6R_7$, pyridyl, piperidinyl, or phenyl, wherein the phenyl is optionally substituted with 1 or more groups that are independently selected from $C_1$-$C_4$ alkyl, $C_1$-$C_4$ alkoxy, halogen, OH, $CF_3$, and $OCF_3$, wherein each $R_6$ and $R_7$ is independently H, $C_1$-$C_6$ alkyl, $C_1$-$C_6$ alkoxycarbonyl, wherein the alkyl portion of each is unsubstituted or substituted with 1, or 2 groups that are independently halogen, OH, $CF_3$, $OCF_3$, $NH_2$, $NH(C_1$-$C_6$ alkyl) or $N(C_1$-$C_6$ alkyl) ($C_1$-$C_6$ alkyl)

Other preferred compounds of Embodiment 31 include those of Embodiment 35, i.e., compounds of Embodiment 31 where $R_1$ is $C_1$-$C_6$ alkenyl substituted with 1, 2, or 3 groups that are independently $C_1$-$C_6$ alkyl, halogen, $C_1$-$C_6$ alkoxy, OH, CN, $CO_2H$, $CF_3$, $OCF_3$, —OC(O)—$C_1$-$C_6$ alkyl, $C_1$-$C_6$ alkoxycarbonyl, $C_1$-$C_6$ alkanoyl, —C(O)$R_{10}$, $NR_6R_7$, —($C_1$-$C_4$ alkyl)-$NR_6R_7$, —C(O)$NR_6R_7$, pyridyl, piperidinyl, or phenyl, wherein the phenyl is optionally substituted with 1 or more groups that are independently selected from $C_1$-$C_4$ alkyl, $C_1$-$C_4$ alkoxy, halogen, OH, $CF_3$, and $OCF_3$, wherein each $R_6$ and $R_7$ is independently H, $C_1$-$C_6$ alkyl, $C_1$-$C_6$ alkoxycarbonyl, wherein the alkyl portion of each is unsubstituted or substituted with 1, or 2 groups that are independently halogen, OH, $CF_3$, $OCF_3$, $NH_2$, $NH(C_1$-$C_6$ alkyl) or $N(C_1$-$C_6$ alkyl) ($C_1$-$C_6$ alkyl).

Other preferred compounds of Embodiment 31 include those of Embodiment 35A, i.e., compounds of Embodiment 31 where $R_1$ is halogen.

Embodiment 35B includes compounds of embodiments 33, 34, and 35, wherein $R_4$ is H, $C_1$-$C_6$ alkyl, or $C_1$-$C_4$ alkoxy $C_1$-$C_6$ alkyl.

Other preferred compounds of Embodiment 35B include those of Embodiment 35C, i.e., compounds of Embodiment 35B where $R_5$ is $C_3$-$C_6$ cycloalkyl, wherein the cycloalkyl is unsubstituted or substituted with 1, 2, or 3 groups that are independently $C_1$-$C_4$ alkyl, $C_1$-$C_4$ alkoxy, halogen, —$SO_2$—($C_1$-$C_4$) alkyl, $CF_3$, $OCF_3$, $NO_2$, CN, OH, phenyl $C_1$-$C_4$ alkyl wherein the phenyl is optionally substituted with 1, 2, 3, 4, or 5 groups that are independently selected from $C_1$-$C_4$ alkyl, $C_1$-$C_4$ alkoxy, CN, halogen, OH, and alkanoyl, $C_1$-$C_4$ alkoxy $C_1$-$C_4$ alkyl, $C_1$-$C_4$ alkoxycarbonyl, $C_1$-$C_4$ alkanoyl, $NR_7R_8$, or —C(O)$NR_7R_8$, wherein $R_7$ and $R_8$ are independently H or $C_1$-$C_6$ alkyl, wherein the $C_1$-$C_6$ alkyl is optionally substituted with 1, 2, or 3 groups that are independently $C_1$-$C_6$ alkoxycarbonyl, halogen, $C_1$-$C_6$ alkoxy, $C_1$-$C_6$ alkanoyl, $NH_2$, $NH(C_1$-$C_6$ alkyl), $N(C_1$-$C_6$ alkyl) ($C_1$-$C_6$ alkyl) or $CO_2H$;

wherein the cycloalkyl portion of $R_4$ and $R_5$ is further optionally substituted with =O, =N—OH, or =N—$OCH_3$; and at least one of $R_2$ and $R_3$ is H.

Other preferred compounds of Embodiment 35C include those of Embodiment 35D, i.e., compounds of Embodiment 35C where wherein Z is a bond.

Other preferred compounds of Embodiment 35C include those of Embodiment 35E, wherein Z is —$CH_2$—.

Other preferred compounds of Embodiment 35C include those of Embodiment 35F wherein Z is —NH—.

Other preferred compounds of Embodiment 35C include those of Embodiment 35G wherein Z is —S— or —$SO_2$—.

Other preferred compounds of Embodiment 35C include those of Embodiment 35H wherein Z is —N($C_1$-$C_4$ alkyl)-. In another aspect, Z is —N($C_1$-$C_2$ alkyl)-. In still another aspect, Z is —N($C_2$-$C_3$ alkyl)-.

Other preferred compounds of Embodiment 35C include those of Embodiment 35I wherein Z is —$SO_2NH$—, or —$SO_2N(C_1$-$C_4$ alkyl)-.

In still another aspect, the invention provides compounds according to embodiments 33, 34, 35, and 35A-35I, wherein $R_{21}$ is H.

In yet still another aspect, the invention provides compounds according to embodiments 33, 34, 35, and 35A-35I, wherein $R_{21}$ is CN.

In still yet another aspect, the invention provides compounds according embodiments 33, 34, 35, and 35A-35I, wherein $R_{21}$ is amino, monoalkylamino, or dialkylamino.

In yet another aspect, the invention provides compounds of embodiments 33, 34, 35, and 35A-35I, wherein $R_{21}$ is OH.

In still another aspect, the invention provides compounds of embodiments 33, 34, 35, and 35A-35I, wherein $R_{21}$ is phenyl.

In still another aspect, the invention provides compounds of embodiments 33, 34, 35, and 35A-35I, wherein $R_{21}$ is pyridyl.

In still another aspect, the invention provides compounds of embodiments 33, 34, 35, and 35A-35I, wherein $R_{21}$ is halogen.

In yet another aspect, the invention provides compounds of embodiments 33, 34, 35, and 35A-35I, wherein $R_{21}$ is phenyl, which is substituted with 1-5 groups that are independently $C_1$-$C_6$ alkyl, $C_1$-$C_6$ alkoxy, halogen, OH, hydroxyl $C_1$-$C_4$ alkyl, haloalkyl (in one aspect, $CF_3$), or haloalkoxy (in one aspect, $OCF_3$)).

In yet still another aspect, the invention provides compounds of embodiments 33, 34, 35, and 35A-35I, wherein $R_{21}$ is pyridyl or pyrimidyl, each of which is optionally substituted with 1-5 groups that are independently $C_1$-$C_6$ alkyl, $C_1$-$C_6$ alkoxy, halogen, OH, hydroxyl $C_1$-$C_4$ alkyl, haloalkyl (in one aspect, $CF_3$), or haloalkoxy (in one aspect, $OCF_3$)).

In yet still another aspect, the invention provides compounds of embodiments 33, 34, 35, and 35A-35I, wherein $R_{21}$ is indolyl or (iso)quinolinyl, each of which is optionally substituted with 1-5 groups that are independently $C_1$-$C_6$ alkyl, $C_1$-$C_6$ alkoxy, halogen, OH, hydroxyl $C_1$-$C_4$ alkyl, haloalkyl (in one aspect, $CF_3$), or haloalkoxy (in one aspect, $OCF_3$)).

In still another aspect, the invention provides compounds of embodiments 33, 34, 35, and 35A-35I, wherein $R_{21}$ is $C_1$-$C_6$ alkyl, $C_2$-$C_6$ alkynyl, or $C_2$-$C_6$ alkenyl.

In still yet another aspect, the invention provides compounds of embodiments 33, 34, 35, and 35A-35I, wherein $R_{21}$ is —C(O)NH$_2$, —C(O)NH($C_1$-$C_6$ alkyl), or —C(O)N($C_1$-$C_6$ alkyl)($C_1$-$C_6$ alkyl).

Other preferred compounds of Embodiment 5 include those of Embodiment 36, i.e., compounds of Embodiment 5 where Z is a bond;

$R_1$ is phenyl, naphthyl, thienyl, furanyl, indolyl, pyridyl, pyridazinyl, pyrimidyl, pyrazinyl, triazolyl, imidazolyl, benzofuranyl, piperidinyl, pyrrolidinyl, piperazinyl, or morpholinyl, each of which is unsubstituted or substituted with 1, 2, 3, 4, or 5 groups that are independently $C_1$-$C_6$ alkyl, halogen, $C_1$-$C_6$ alkoxy, OH, CN, $CO_2H$, $C_1$-$C_4$ haloalkyl, $C_1$-$C_4$ haloalkoxy, —OC(O)—$C_1$-$C_6$ alkyl, $C_1$-$C_6$ alkoxycarbonyl, $C_1$-$C_6$ alkanoyl, —C(O)R$_{10}$, NR$_6$R$_7$, —($C_1$-$C_4$ alkyl)-NR$_6$R$_7$, —C(O)NR$_6$R$_7$, heteroaryl selected from pyridyl, pyrimidyl, pyrazinyl, (iso)quinolinyl, indolyl, thienyl, furanyl, pyrrolyl, triazinyl, 1H-indazolyl, and benzimidazolyl, heterocycloalkyl selected from piperidinyl, pyrrolidinyl, tetrahydrofuranyl, tetrahydroisoquinolinyl, imidazolidinyl, piperazinyl, morpholinyl, and S,S-dioxomorpholinyl, phenyl, naphthyl, wherein the heteroaryl, heterocycloalkyl, or phenyl, which is optionally substituted with 1, 2, 3, 4, or 5 groups that are independently selected from $C_1$-$C_4$ alkyl, $C_1$-$C_4$ alkoxy, halogen, $CF_3$, and $OCF_3$, wherein each $R_6$ and $R_7$ is independently H, $C_1$-$C_6$ alkyl, $C_1$-$C_4$ alkoxyalkyl, $C_1$-$C_6$ alkoxycarbonyl, wherein the alkyl portion of each is unsubstituted or substituted with 1, 2, or 3, groups that are independently halogen, OH, $C_1$-$C_4$ haloalkyl, $C_1$-$C_4$ haloalkoxy, NH$_2$, NH($C_1$-$C_6$ alkyl) or N($C_1$-$C_6$ alkyl)($C_1$-$C_6$ alkyl); and $R_{10}$ is $C_2$-$C_6$ alkenyl, $C_2$-$C_6$ alkynyl, phenyl, naphthyl, pyridyl, quinolinyl, pyrimidyl, furanyl, indolyl, $C_3$-$C_8$ cycloalkyl, wherein the cyclic portions are optionally substituted with halogen, $C_1$-$C_6$ alkyl, $C_1$-$C_6$ alkoxy, OH, $CO_2H$, CN, $NO_2$, $C_1$-$C_4$ haloalkyl, or $C_1$-$C_4$ haloalkoxy;

wherein the heterocycloalkyl and the cycloalkyl portions of $R_1$ and $R_{10}$ are further optionally substituted with =O, =N—OH, or =N—OCH$_3$.

Other preferred compounds of Embodiment 36 include those of Embodiment 37, i.e., compounds of Embodiment 36 where $R_4$ and $R_5$ and the nitrogen to which they are attached form a piperazinyl, morpholinyl, piperidinyl, imidazolidinyl, or pyrrolidinyl ring, each of which is unsubstituted or substituted with 1 or more groups that are independently $C_1$-$C_4$ alkyl, $C_1$-$C_4$ alkoxy, halogen, phenyl $C_1$-$C_4$ alkyl, $C_1$-$C_6$ alkanoyl, OH, pyridyl, pyrimidyl, pyrazinyl, pyrimidyl $C_1$-$C_4$ alkyl, pyrazinyl $C_1$-$C_4$ alkyl, phenyl, —OCH$_2$CH$_2$O—, —OCH$_2$O—, wherein the pyridyl, pyrimidyl, pyrazinyl, pyrimidyl $C_1$-$C_6$ alkyl, and phenyl groups are unsubstituted or substituted with 1 or more groups that are independently $C_1$-$C_4$ alkyl, $C_1$-$C_4$ alkoxy, halogen, $CF_3$ or $OCF_3$.

Other preferred compounds of Embodiment 37 include those of Embodiment 38, i.e., compounds of Embodiment 37 where $R_1$ is phenyl which is unsubstituted or substituted with 1, 2, 3, 4, or 5 groups that are independently $C_1$-$C_6$ alkyl, halogen, $C_1$-$C_6$ alkoxy, OH, CN, $CO_2H$, $C_1$-$C_4$ haloalkyl, $C_1$-$C_4$ haloalkoxy, —OC(O)—$C_1$-$C_6$ alkyl, $C_1$-$C_6$ alkoxycarbonyl, $C_1$-$C_6$ alkanoyl, —C(O)R$_{10}$, NR$_6$R$_7$, —($C_1$-$C_4$ alkyl)—NR$_6$R$_7$, —C(O)NR$_6$R$_7$, heteroaryl selected from pyridyl, pyrimidyl, indolyl, thienyl, furanyl, and pyrrolyl, heterocycloalkyl selected from piperidinyl, pyrrolidinyl, piperazinyl, and morpholinyl, phenyl, wherein the heteroaryl, heterocycloalkyl phenyl and naphthyl groups are optionally substituted with each of which is optionally substituted with 1, 2, 3, 4, or 5 groups that are independently selected from $C_1$-$C_4$ alkyl, $C_1$-$C_4$ alkoxy, halogen, $CF_3$, and $OCF_3$, wherein each $R_6$ and $R_7$ is independently H, $C_1$-$C_6$ alkyl, $C_1$-$C_4$ alkoxyalkyl, $C_1$-$C_6$ alkoxycarbonyl, wherein the alkyl portion of each is unsubstituted or substituted with 1, 2, or 3, groups that are independently halogen, OH, $CF_3$, $OCF_3$, NH$_2$, NH($C_1$-$C_6$ alkyl) or N($C_1$-$C_6$ alkyl)($C_1$-$C_6$ alkyl)

Other preferred compounds of Embodiment 38 include those of Embodiment 39, i.e., compounds of Embodiment 38 where $R_2$ and $R_3$ are both H; and $R_4$ and $R_5$ and the nitrogen to which they are attached form a piperazinyl, morpholinyl, piperidinyl, or pyrrolidinyl ring, each of which is substituted with 1 or more groups that are independently $C_1$-$C_4$ alkyl, $C_1$-$C_4$ alkoxy, halogen, phenyl $C_1$-$C_4$ alkyl, $C_1$-$C_6$ alkanoyl, OH, pyridyl, pyrimidyl, pyrazinyl, pyrimidyl $C_1$-$C_4$ alkyl, pyrazinyl $C_1$-$C_4$ alkyl, phenyl, —OCH$_2$CH$_2$O—, or —OCH$_2$O—.

Preferred compounds of Embodiment 39 include those of Embodiment 39A, i.e., compounds of Embodiment 39 where $R_4$ and $R_5$ and the nitrogen to which they are attached form a piperazinyl, morpholinyl, piperidinyl, or pyrrolidinyl ring, wherein the piperazinyl and piperidinyl rings are substituted at position 4, wherein the morpholinyl, and pyrrolidinyl rings are substituted at position 3.

Preferred compounds of Embodiment 37 include those of Embodiment 40, i.e., compounds of Embodiment 37 where $R_1$ is thienyl, furanyl, indolyl, pyridyl, pyridazinyl, pyrimidyl, pyrazinyl, triazolyl, imidazolyl, benzofuranyl, piperidinyl, pyrrolidinyl, piperazinyl, or morpholinyl, each of which is unsubstituted or substituted with 1, 2, 3, or 4 groups that are independently $C_1$-$C_6$ alkyl, halogen, $C_1$-$C_6$ alkoxy, OH, CN, $CO_2H$, $CF_3$, $OCF_3$, —OC(O)— $C_1$-$C_6$ alkyl, $C_1$-$C_6$ alkoxycarbonyl, $C_1$-$C_6$ alkanoyl, $NR_6R_7$, —($C_1$-$C_4$ alkyl)—$NR_6R_7$, —$C(O)NR_6R_7$, pyridyl, piperidinyl, or phenyl, wherein the pyridyl, piperidinyl, and phenyl groups are optionally substituted with 1, 2, 3, 4, or 5 groups that are independently selected from $C_1$-$C_4$ alkyl, $C_1$-$C_4$ alkoxy, halogen, $CF_3$, and $OCF_3$, wherein each $R_6$ and $R_7$ is independently H, $C_1$-$C_6$ alkyl, $C_1$-$C_4$ alkoxyalkyl, $C_1$-$C_6$ alkoxycarbonyl, wherein the alkyl portion of each is unsubstituted or substituted with 1, 2, or 3, groups that are independently halogen, OH, $C_1$-$C_4$ haloalkyl, $C_1$-$C_4$ haloalkoxy, $NH_2$, $NH(C_1$-$C_6$ alkyl) or $N(C_1$-$C_6$ alkyl)($C_1$-$C_6$ alkyl); and wherein the heterocycloalkyl portion of $R_{10}$ is further optionally substituted with =O, =N—OH, or =N—$OCH_3$.

Preferred compounds of Embodiment 40 include those of Embodiment 41, i.e., compounds of Embodiment 40 where $R_2$ and $R_3$ are both H; and $R_4$ and $R_5$ and the nitrogen to which they are attached form a piperazinyl, morpholinyl, piperidinyl, or pyrrolidinyl ring, each of which is substituted with 1 or more groups that are independently $C_1$-$C_4$ alkyl, $C_1$-$C_4$ alkoxy, halogen, phenyl $C_1$-$C_4$ alkyl, $C_1$-$C_6$ alkanoyl, OH, pyridyl, pyrimidyl, pyrazinyl, pyrimidyl $C_1$-$C_4$ alkyl, pyrazinyl $C_1$-$C_4$ alkyl, phenyl, —$OCH_2CH_2O$—, or —$OCH_2O$—.

Preferred compounds of Embodiment 41 include those of Embodiment 42, i.e., compounds of Embodiment 41 where $R_1$ is thienyl optionally substituted with 1, 2, 3, or 4 groups that are independently $C_1$-$C_6$ alkyl, halogen, $C_1$-$C_6$ alkoxy, OH, CN, $CO_2H$, $CF_3$, $OCF_3$, —OC(O)—$C_1$-$C_6$ alkyl, $C_1$-$C_6$ alkoxycarbonyl, $C_1$-$C_6$ alkanoyl, $NR_6R_7$, —($C_1$-$C_4$ alkyl)-$NR_6R_7$, —$C(O)NR_6R_7$, pyridyl, piperidinyl, or phenyl, which is optionally substituted with 1, 2, 3, 4, or 5 groups that are independently selected from $C_1$-$C_4$ alkyl, $C_1$-$C_4$ alkoxy, halogen, $CF_3$, and $OCF_3$, wherein each $R_6$ and $R_7$ is independently H, $C_1$-$C_6$ alkyl, $C_1$-$C_4$ alkoxyalkyl, $C_1$-$C_6$ alkoxycarbonyl, wherein the alkyl portion of each is unsubstituted or substituted with 1, 2, or 3, groups that are independently halogen, OH, $C_1$-$C_4$ haloalkyl, $C_1$-$C_4$ haloalkoxy, $NH_2$, $NH(C_1$-$C_6$ alkyl) or $N(C_1$-$C_6$ alkyl)($C_1$-$C_6$ alkyl)

Preferred compounds of Embodiment 41 include those of Embodiment 43, i.e., compounds of Embodiment 41 where $R_1$ is benzofuranyl optionally substituted with 1, 2, 3, or 4 groups that are independently $C_1$-$C_6$ alkyl, halogen, $C_1$-$C_6$ alkoxy, OH, CN, $CO_2H$, $CF_3$, $OCF_3$, —OC(O)—$C_1$-$C_6$ alkyl, $C_1$-$C_6$ alkoxycarbonyl, $C_1$-$C_6$ alkanoyl, $NR_6R_7$, —($C_1$-$C_4$ alkyl)—$NR_6R_7$, —$C(O)NR_6R_7$, pyridyl, piperidinyl, or phenyl, which is optionally substituted with 1, 2, 3, 4, or 5 groups that are independently selected from $C_1$-$C_4$ alkyl, $C_1$-$C_4$ alkoxy, halogen, $CF_3$, and $OCF_3$, wherein each $R_6$ and $R_7$ is independently H, $C_1$-$C_6$ alkyl, $C_1$-$C_4$ alkoxyalkyl, $C_1$-$C_6$ alkoxycarbonyl, wherein the alkyl portion of each is unsubstituted or substituted with 1, 2, or 3, groups that are independently halogen, OH, $C_1$-$C_4$ haloalkyl, $C_1$-$C_4$ haloalkoxy, $NH_2$, $NH(C_1$-$C_6$ alkyl) or $N(C_1$-$C_6$ alkyl)($C_1$-$C_6$ alkyl)

Preferred compounds of Embodiment 36 include those of Embodiment 44, i.e., compounds of Embodiment 36 where $R_4$ and $R_5$ are independently H, $C_1$-$C_6$ alkyl, $C_1$-$C_4$ alkoxy $C_1$-$C_6$ alkyl, $C_3$-$C_8$ cycloalkyl, piperidinyl, pyrrolidinyl, morpholinyl, morpholinyl $C_1$-$C_6$ alkyl, piperidinyl $C_1$-$C_6$ alkyl, pyrrolidinyl $C_1$-$C_6$ alkyl, piperidinyl $C_2$-$C_6$ alkenyl, pyrrolidinyl $C_2$-$C_6$ alkenyl, morpholinyl $C_2$-$C_6$ alkenyl, piperidinyl $C_2$-$C_6$ alkynyl, pyrrolidinyl $C_2$-$C_6$ alkynyl, morpholinyl $C_2$-$C_6$ alkynyl, phenyl, furanyl, pyridyl, pyrazinyl $C_1$-$C_6$ alkyl, pyridyl $C_1$-$C_6$ alkyl, imidazolyl $C_1$-$C_6$ alkyl, furanyl $C_1$-$C_6$ alkyl, thienyl $C_1$-$C_6$ alkyl, phenyl $C_1$-$C_6$ alkyl, phenyl $C_2$-$C_6$ alkenyl, phenyl $C_2$-$C_6$ alkynyl, wherein the cyclic portion of each of the above is unsubstituted or substituted with one or more groups that are independently $C_1$-$C_6$ alkyl, $C_1$-$C_6$ alkoxy, halogen, —$SO_2$— ($C_1$-$C_6$) alkyl, $C_1$-$C_4$ haloalkyl, $C_1$-$C_4$ haloalkoxy, $NO_2$, CN, OH, phenyl $C_1$-$C_6$ alkyl wherein the phenyl is optionally substituted with 1, 2, 3, 4, or 5 groups that are independently selected from $C_1$-$C_4$ alkyl, $C_1$-$C_4$ alkoxy, CN, halogen, OH, and alkanoyl, $C_1$-$C_6$ alkoxy $C_1$-$C_6$ alkyl, $C_1$-$C_6$ alkoxycarbonyl, $C_1$-$C_6$ alkanoyl, $NR_7R_8$, or —$C(O)NR_7R_8$, wherein $R_7$ and $R_8$ are independently H or $C_1$-$C_6$ alkyl, wherein the $C_1$-$C_6$ alkyl is optionally substituted with 1, 2, or 3 groups that are independently $C_1$-$C_6$ alkoxycarbonyl, halogen, $C_1$-$C_6$ alkoxy, $C_1$-$C_6$ alkanoyl, $NH_2$, $NH(C_1$-$C_6$ alkyl), $N(C_1$-$C_6$ alkyl) ($C_1$-$C_6$ alkyl) or $CO_2H$;

wherein the heterocycloalkyl and the cycloalkyl portions of $R_4$ and $R_5$ are further optionally substituted with =O, =N—OH, or =N—$OCH_3$.

Preferred compounds of Embodiment 44 include those of Embodiment 45, i.e., compounds of Embodiment 44 where $R_1$ is phenyl which is unsubstituted or substituted with 1, 2, 3, 4, or 5 groups that are independently $C_1$-$C_6$ alkyl, halogen, $C_1$-$C_6$ alkoxy, OH, CN, $CO_2H$, $C_1$-$C_4$ haloalkyl, $C_1$-$C_4$ haloalkoxy, —OC(O)—$C_1$-$C_6$ alkyl, $C_1$-$C_6$ alkoxycarbonyl, $C_1$-$C_6$ alkanoyl, —$C(O)R_{10}$, $NR_6R_7$, —($C_1$-$C_4$ alkyl)-$NR_6R_7$, —$C(O)NR_6R_7$, pyridyl, piperidinyl, or phenyl, which is optionally substituted with 1, 2, 3, 4, or 5 groups that are independently selected from $C_1$-$C_4$ alkyl, $C_1$-$C_4$ alkoxy, halogen, $CF_3$, and $OCF_3$, wherein each $R_6$ and $R_7$ is independently H, $C_1$-$C_6$ alkyl, $C_1$-$C_4$ alkoxyalkyl, $C_1$-$C_6$ alkoxycarbonyl, wherein the alkyl portion of each is unsubstituted or substituted with 1, 2, or 3, groups that are independently halogen, OH, $CF_3$, $OCF_3$, $NH_2$, $NH(C_1$-$C_6$ alkyl) or $N(C_1$-$C_6$ alkyl)($C_1$-$C_6$ alkyl).

Preferred compounds of Embodiment 45 include those of Embodiment 45A, i.e., compounds of Embodiment 45 where A compound according to embodiment 36, wherein $R_4$ is H, $C_1$-$C_6$ alkyl, or $C_1$-$C_4$ alkoxy $C_1$-$C_6$ alkyl.

Preferred compounds of Embodiment 45A include those of Embodiment 45B, i.e., compounds of Embodiment 45A where $R_5$ is $C_3$-$C_8$ cycloalkyl, which is unsubstituted or substituted with one or more groups that are independently $C_1$-$C_6$ alkyl, $C_1$-$C_6$ alkoxy, halogen, —$SO_2$—($C_1$-$C_6$) alkyl, $C_1$-$C_4$ haloalkyl, $C_1$-$C_4$ haloalkoxy, $NO_2$, CN, OH, phenyl $C_1$-$C_6$ alkyl wherein the phenyl is optionally substituted with 1, 2, 3, 4, or 5 groups that are independently selected from $C_1$-$C_4$ alkyl, $C_1$-$C_4$ alkoxy, CN, halogen, OH, and alkanoyl, $C_1$-$C_6$ alkoxy $C_1$-$C_6$ alkyl, $C_1$-$C_6$ alkoxycarbonyl, $C_1$-$C_6$ alkanoyl, $NR_7R_8$, or —$C(O)NR_7R_8$, wherein $R_7$ and $R_8$ are independently H or $C_1$-$C_6$ alkyl, wherein the $C_1$-$C_6$ alkyl is optionally substituted with 1, 2, or 3 groups that are independently $C_1$-$C_6$ alkoxycarbonyl, halogen, $C_1$-$C_6$ alkoxy, $C_1$-$C_6$ alkanoyl, $NH_2$, $NH(C_1$-$C_6$ alkyl), $N(C_1$-$C_6$ alkyl) ($C_1$-$C_6$ alkyl) or $CO_2H$;

wherein the cycloalkyl portion of $R_5$ is further optionally substituted with =O, =N—OH, or =N—$OCH_3$.

Preferred compounds of Embodiment 45A include those of Embodiment 45C, i.e., compounds of Embodiment 45A where $R_5$ is piperidinyl, pyrrolidinyl, morpholinyl, phenyl, furanyl, or pyridyl, wherein the cyclic portion of each of the above is unsubstituted or substituted with one or more groups that are independently $C_1$-$C_6$ alkyl, $C_1$-$C_6$ alkoxy, halogen, —$SO_2$—($C_1$-$C_6$) alkyl, $C_1$-$C_4$ haloalkyl, $C_1$-$C_4$ haloalkoxy, $NO_2$, CN, OH, phenyl $C_1$-$C_6$ alkyl wherein the phenyl is optionally substituted with 1, 2, 3, 4, or 5 groups that are independently selected from $C_1$-$C_4$ alkyl, $C_1$-$C_4$ alkoxy, CN, halogen, OH, and alkanoyl, $C_1$-$C_6$ alkoxy $C_1$-$C_6$ alkyl, $C_1$-$C_6$ alkoxycarbonyl, $C_1$-$C_6$ alkanoyl, $NR_7R_8$, or —$C(O)NR_7R_8$, wherein $R_7$ and $R_8$ are independently H or $C_1$-$C_6$ alkyl, wherein the $C_1$-$C_6$ alkyl is optionally substituted with 1, 2, or 3 groups that are independently $C_1$-$C_6$ alkoxycarbonyl, halogen, $C_1$-$C_6$ alkoxy, $C_1$-$C_6$ alkanoyl, $NH_2$, $NH(C_1$-$C_6$ alkyl), $N(C_1$-$C_6$ alkyl) ($C_1$-$C_6$ alkyl) or $CO_2H$;

wherein the heterocycloalkyl portion of $R_5$ is further optionally substituted with =O, =N—OH, or =N—$OCH_3$.

Preferred compounds of Embodiment 45A include those of Embodiment 45D, i.e., compounds of Embodiment 45A where $R_5$ is morpholinyl $C_1$-$C_6$ alkyl, piperidinyl $C_1$-$C_6$ alkyl, pyrrolidinyl $C_1$-$C_6$ alkyl, piperidinyl $C_2$-$C_6$ alkenyl, pyrrolidinyl $C_2$-$C_6$ alkenyl, morpholinyl $C_2$-$C_6$ alkenyl, piperidinyl $C_2$-$C_6$ alkynyl, pyrrolidinyl $C_2$-$C_6$ alkynyl, morpholinyl $C_2$-$C_6$ alkynyl, pyrazinyl $C_1$-$C_6$ alkyl, pyridyl $C_1$-$C_6$ alkyl, imidazolyl $C_1$-$C_6$ alkyl, furanyl $C_1$-$C_6$ alkyl, thienyl $C_1$-$C_6$ alkyl, phenyl $C_1$-$C_6$ alkyl, phenyl $C_2$-$C_6$ alkenyl, phenyl $C_2$-$C_6$ alkynyl, wherein the cyclic portion of each of the above is unsubstituted or substituted with one or more groups that are independently $C_1$-$C_6$ alkyl, $C_1$-$C_6$ alkoxy, halogen, —$SO_2$—($C_1$-$C_6$) alkyl, $C_1$-$C_4$ haloalkyl, $C_1$-$C_4$ haloalkoxy, $NO_2$, CN, OH, phenyl $C_1$-$C_6$ alkyl wherein the phenyl is optionally substituted with 1, 2, 3, 4, or 5 groups that are independently selected from $C_1$-$C_4$ alkyl, $C_1$-$C_4$ alkoxy, CN, halogen, OH, and alkanoyl, $C_1$-$C_6$ alkoxy $C_1$-$C_6$ alkyl, $C_1$-$C_6$ alkoxycarbonyl, $C_1$-$C_6$ alkanoyl, $NR_7R_8$, or —$C(O)NR_7R_8$, wherein $R_7$ and $R_8$ are independently H or $C_1$-$C_6$ alkyl, wherein the $C_1$-$C_6$ alkyl is optionally substituted with 1, 2, or 3 groups that are independently $C_1$-$C_6$ alkoxycarbonyl, halogen, $C_1$-$C_6$ alkoxy, $C_1$-$C_6$ alkanoyl, $NH_2$, $NH(C_1$-$C_6$ alkyl), $N(C_1$-$C_6$ alkyl) ($C_1$-$C_6$ alkyl) or $CO_2H$;

wherein the heterocycloalkyl portion of $R_5$ is further optionally substituted with =O, =N—OH, or =N—$OCH_3$.

Preferred compounds of Embodiment 45A include those of Embodiment 45E, i.e., compounds of Embodiment 45A where $R_5$ is morpholinyl $C_1$-$C_6$ alkyl, piperidinyl $C_1$-$C_6$ alkyl, pyrrolidinyl $C_1$-$C_6$ alkyl, pyrazinyl $C_1$-$C_6$ alkyl, pyridyl $C_1$-$C_6$ alkyl, imidazolyl $C_1$-$C_6$ alkyl, furanyl $C_1$-$C_6$ alkyl, thienyl $C_1$-$C_6$ alkyl, or phenyl $C_1$-$C_6$ alkyl, wherein the cyclic portion of each of the above is unsubstituted or substituted with one or more groups that are independently $C_1$-$C_6$ alkyl, $C_1$-$C_6$ alkoxy, halogen, —$SO_2$—($C_1$-$C_6$) alkyl, $C_1$-$C_4$ haloalkyl, $C_1$-$C_4$ haloalkoxy, $NO_2$, CN, OH, phenyl $C_1$-$C_6$ alkyl wherein the phenyl is optionally substituted with 1, 2, 3, 4, or 5 groups that are independently selected from $C_1$-$C_4$ alkyl, $C_1$-$C_4$ alkoxy, CN, halogen, OH, and alkanoyl, $C_1$-$C_6$ alkoxy $C_1$-$C_6$ alkyl, $C_1$-$C_6$ alkoxycarbonyl, $C_1$-$C_6$ alkanoyl, $NR_7R_8$, or —$C(O)NR_7R_8$, wherein $R_7$ and $R_8$ are independently H or $C_1$-$C_6$ alkyl, wherein the $C_1$-$C_6$ alkyl is optionally substituted with 1, 2, or 3 groups that are independently $C_1$-$C_6$ alkoxycarbonyl, halogen, $C_1$-$C_6$ alkoxy, $C_1$-$C_6$ alkanoyl, $NH_2$, $NH(C_1$-$C_6$ alkyl), $N(C_1$-$C_6$ alkyl) ($C_1$-$C_6$ alkyl) or $CO_2H$;

wherein the heterocycloalkyl portion of $R_5$ is further optionally substituted with =O, =N—OH, or =N—$OCH_3$.

Preferred compounds of Embodiment 45A include those of Embodiment 45F, i.e., compounds of Embodiment 45A where $R_5$ is piperidinyl $C_2$-$C_6$ alkenyl, pyrrolidinyl $C_2$-$C_6$ alkenyl, morpholinyl $C_2$-$C_6$ alkenyl, piperidinyl $C_2$-$C_6$ alkynyl, pyrrolidinyl $C_2$-$C_6$ alkynyl, morpholinyl $C_2$-$C_6$ alkynyl, phenyl $C_2$-$C_6$ alkenyl, or phenyl $C_2$-$C_6$ alkynyl, wherein the cyclic portion of each of the above is unsubstituted or substituted with one or more groups that are independently $C_1$-$C_6$ alkyl, $C_1$-$C_6$ alkoxy, halogen, —$SO_2$—($C_1$-$C_6$) alkyl, $C_1$-$C_4$ haloalkyl, $C_1$-$C_4$ haloalkoxy, $NO_2$, CN, OH, phenyl $C_1$-$C_6$ alkyl wherein the phenyl is optionally substituted with 1, 2, 3, 4, or 5 groups that are independently selected from $C_1$-$C_4$ alkyl, $C_1$-$C_4$ alkoxy, CN, halogen, OH, and alkanoyl, $C_1$-$C_6$ alkoxy $C_1$-$C_6$ alkyl, $C_1$-$C_6$ alkoxycarbonyl, $C_1$-$C_6$ alkanoyl, $NR_7R_8$, or —$C(O)NR_7R_8$, wherein $R_7$ and $R_8$ are independently H or $C_1$-$C_6$ alkyl, wherein the $C_1$-$C_6$ alkyl is optionally substituted with 1, 2, or 3 groups that are independently $C_1$-$C_6$ alkoxycarbonyl, halogen, $C_1$-$C_6$ alkoxy, $C_1$-$C_6$ alkanoyl, $NH_2$, $NH(C_1$-$C_6$ alkyl), $N(C_1$-$C_6$ alkyl) ($C_1$-$C_6$ alkyl) or $CO_2H$;

wherein the heterocycloalkyl portion of $R_5$ is further optionally substituted with =O, =N—OH, or =N—$OCH_3$.

In still another aspect, the invention provides compounds according to embodiments 45 and 45A-45F, wherein $R_{21}$ is H.

In yet still another aspect, the invention provides compounds according to embodiments 45 and 45A-45F, wherein $R_{21}$ is CN.

In still yet another aspect, the invention provides compounds according to embodiments 45 and 45A-45F, wherein $R_{21}$ is amino, monoalkylamino, or dialkylamino.

In yet another aspect, the invention provides compounds of embodiments 45 and 45A-45F, wherein $R_{21}$ is OH.

In still another aspect, the invention provides compounds of embodiments 45 and 45A-45F, wherein $R_{21}$ is phenyl.

In still another aspect, the invention provides compounds of embodiments 45 and 45A-45F, wherein $R_{21}$ is pyridyl.

In still another aspect, the invention provides compounds of embodiments 45 and 45A-45F, wherein $R_{21}$ is halogen.

In yet another aspect, the invention provides compounds of embodiments 45 and 45A-45F, wherein $R_{21}$ is phenyl, which is substituted with 1-5 groups that are independently $C_1$-$C_6$ alkyl, $C_1$-$C_6$ alkoxy, halogen, OH, hydroxyl $C_1$-$C_4$ alkyl, haloalkyl (in one aspect, $CF_3$), or haloalkoxy (in one aspect, $OCF_3$)).

In yet still another aspect, the invention provides compounds of embodiments 45 and 45A-45F, wherein $R_{21}$ is pyridyl or pyrimidyl, each of which is optionally substituted with 1-5 groups that are independently $C_1$-$C_6$ alkyl, $C_1$-$C_6$ alkoxy, halogen, OH, hydroxyl $C_1$-$C_4$ alkyl, haloalkyl (in one aspect, $CF_3$), or haloalkoxy (in one aspect, $OCF_3$)).

In yet still another aspect, the invention provides compounds of embodiments 45 and 45A-45F, wherein $R_{21}$ is indolyl or (iso)quinolinyl, each of which is optionally substituted with 1-5 groups that are independently $C_1$-$C_6$ alkyl, $C_1$-$C_6$ alkoxy, halogen, OH, hydroxyl $C_1$-$C_4$ alkyl, haloalkyl (in one aspect, $CF_3$), or haloalkoxy (in one aspect, $OCF_3$)).

In still another aspect, the invention provides compounds of embodiments 45 or 45A-45F, wherein $R_{21}$ is $C_1$-$C_6$ alkyl, $C_2$-$C_6$ alkynyl, or $C_2$-$C_6$ alkenyl.

In still yet another aspect, the invention provides compounds of embodiments 45 or 45A-45F, wherein $R_{21}$ is —C(O)NH$_2$, —C(O)NH($C_1$-$C_6$ alkyl), or —C(O)N($C_1$-$C_6$ alkyl) ($C_1$-$C_6$ alkyl).

Preferred compounds of Embodiment 36 include those of Embodiment 46, i.e., compounds of Embodiment 36 where $R_2$ and $R_3$ are both H; and $R_4$ and $R_5$ are independently H, $C_1$-$C_6$ alkyl, $C_1$-$C_4$ alkoxy $C_1$-$C_6$ alkyl, piperidinyl, pyrrolidinyl, morpholinyl, morpholinyl $C_1$-$C_6$ alkyl, piperidinyl $C_1$-$C_6$ alkyl, pyrrolidinyl $C_1$-$C_6$ alkyl, phenyl, furanyl, pyridyl, pyrazinyl $C_1$-$C_6$ alkyl, pyridyl $C_1$-$C_6$ alkyl, imidazolyl $C_1$-$C_6$ alkyl, furanyl $C_1$-$C_6$ alkyl, thienyl $C_1$-$C_6$ alkyl, phenyl $C_1$-$C_6$ alkyl, wherein the cyclic portion of each of the above is unsubstituted or substituted with one or more groups that are independently $C_1$-$C_6$ alkyl, $C_1$-$C_6$ alkoxy, halogen, —SO$_2$—($C_1$-$C_6$) alkyl, $C_1$-$C_4$ haloalkyl, $C_1$-$C_4$ haloalkoxy, NO$_2$, CN, OH, phenyl $C_1$-$C_6$ alkyl wherein the phenyl is optionally substituted with 1, 2, 3, 4, or 5 groups that are independently selected from $C_1$-$C_4$ alkyl, $C_1$-$C_4$ alkoxy, CN, halogen, OH, and alkanoyl, $C_1$-$C_6$ alkoxy $C_1$-$C_6$ alkyl, $C_1$-$C_6$ alkoxycarbonyl, $C_1$-$C_6$ alkanoyl, NR$_7$R$_8$, or —C(O)NR$_7$R$_8$,
  wherein $R_7$ and $R_8$ are independently H or $C_1$-$C_6$ alkyl, wherein the $C_1$-$C_6$ alkyl is optionally substituted with 1, 2, or 3 groups that are independently $C_1$-$C_6$ alkoxycarbonyl, halogen, $C_1$-$C_6$ alkoxy, $C_1$-$C_6$ alkanoyl, NH$_2$, NH($C_1$-$C_6$ alkyl), N($C_1$-$C_6$ alkyl) ($C_1$-$C_6$ alkyl) or CO$_2$H;
  wherein the heterocycloalkyl and the cycloalkyl portions of $R_4$ and $R_5$ are further optionally substituted with =O, =N—OH, or =N—OCH$_3$.

Preferred compounds of Embodiment 46 include those of Embodiment 47, i.e., compounds of Embodiment 46 where $R_1$ is thienyl, furanyl, indolyl, pyridyl, pyridazinyl, pyrimidyl, pyrazinyl, triazolyl, imidazolyl, benzofuranyl, piperidinyl, pyrrolidinyl, piperazinyl, or morpholinyl, each of which is unsubstituted or substituted with 1, 2, 3, or 4 groups that are independently $C_1$-$C_6$ alkyl, halogen, $C_1$-$C_6$ alkoxy, OH, CN, CO$_2$H, CF$_3$, OCF$_3$, —OC(O)—$C_1$-$C_6$ alkyl, $C_1$-$C_6$ alkoxycarbonyl, $C_1$-$C_6$ alkanoyl, NR$_6$R$_7$, —($C_1$-$C_4$ alkyl)-NR$_6$R$_7$, —C(O)NR$_6$R$_7$, pyridyl, piperidinyl, or phenyl, which is optionally substituted with 1, 2, 3, 4, or 5 groups that are independently selected from $C_1$-$C_4$ alkyl, $C_1$-$C_4$ alkoxy, halogen, CF$_3$, and OCF$_3$, wherein
  each $R_6$ and $R_7$ is independently H, $C_1$-$C_6$ alkyl, $C_1$-$C_4$ alkoxyalkyl, $C_1$-$C_6$ alkoxycarbonyl, wherein the alkyl portion of each is unsubstituted or substituted with 1, 2, or 3, groups that are independently halogen, OH, $C_1$-$C_4$ haloalkyl, $C_1$-$C_4$ haloalkoxy, NH$_2$, NH($C_1$-$C_6$ alkyl) or N($C_1$-$C_6$ alkyl) ($C_1$-$C_6$ alkyl).

Preferred compounds of Embodiment 47 include those of Embodiment 48, i.e., compounds of Embodiment 47 where $R_1$ is thienyl optionally substituted with 1, 2, 3, or 4 groups that are independently $C_1$-$C_6$ alkyl, halogen, $C_1$-$C_6$ alkoxy, OH, CN, CO$_2$H, CF$_3$, OCF$_3$, —OC(O)—$C_1$-$C_6$ alkyl, $C_1$-$C_6$ alkoxycarbonyl, $C_1$-$C_6$ alkanoyl, NR$_6$R$_7$, —($C_1$-$C_4$ alkyl)-NR$_6$R$_7$, —C(O)NR$_6$R$_7$, pyridyl, piperidinyl, or phenyl, which is optionally substituted with 1, 2, 3, 4, or 5 groups that are independently selected from $C_1$-$C_4$ alkyl, $C_1$-$C_4$ alkoxy, halogen, CF$_3$, and OCF$_3$, wherein
  each $R_6$ and $R_7$ is independently H, $C_1$-$C_6$ alkyl, $C_1$-$C_4$ alkoxyalkyl, $C_1$-$C_6$ alkoxycarbonyl, wherein the alkyl portion of each is unsubstituted or substituted with 1, 2, or 3, groups that are independently halogen, OH, $C_1$-$C_4$ haloalkyl, $C_1$-$C_4$ haloalkoxy, NH$_2$, NH($C_1$-$C_6$ alkyl) or N($C_1$-$C_6$ alkyl) ($C_1$-$C_6$ alkyl)

Preferred compounds of Embodiment 47 include those of Embodiment 49, i.e., compounds of Embodiment 47 where $R_1$ is benzofuranyl optionally substituted with 1, 2, 3, or 4 groups that are independently $C_1$-$C_6$ alkyl, halogen, $C_1$-$C_6$ alkoxy, OH, CN, CO$_2$H, CF$_3$, OCF$_3$, —OC(O)—$C_1$-$C_6$ alkyl, $C_1$-$C_6$ alkoxycarbonyl, $C_1$-$C_6$ alkanoyl, NR$_6$R$_7$, —($C_1$-$C_4$ alkyl)-NR$_6$R$_7$, —C(O)NR$_6$R$_7$, or phenyl, which is optionally substituted with 1, 2, 3, 4, or 5 groups that are independently selected from $C_1$-$C_4$ alkyl, $C_1$-$C_4$ alkoxy, halogen, CF$_3$, and OCF$_3$, wherein
  each $R_6$ and $R_7$ is independently H, $C_1$-$C_6$ alkyl, $C_1$-$C_4$ alkoxyalkyl, $C_1$-$C_6$ alkoxycarbonyl, wherein the alkyl portion of each is unsubstituted or substituted with 1, 2, or 3, groups that are independently halogen, OH, $C_1$-$C_4$ haloalkyl, $C_1$-$C_4$ haloalkoxy, NH$_2$, NH($C_1$-$C_6$ alkyl) or N($C_1$-$C_6$ alkyl) ($C_1$-$C_6$ alkyl).

Embodiment 49A includes compounds of embodiments 47, 48 and 49, wherein, $R_4$ is H, $C_1$-$C_6$ alkyl, or $C_1$-$C_4$ alkoxy $C_1$-$C_6$ alkyl.

Preferred compounds of Embodiment 49A include those of Embodiment 49B, i.e., compounds of Embodiment 49A where
$R_5$ is piperidinyl, pyrrolidinyl, morpholinyl, phenyl, furanyl, or pyridyl, wherein the cyclic portion of each of the above is unsubstituted or substituted with one or more groups that are independently $C_1$-$C_6$ alkyl, $C_1$-$C_6$ alkoxy, halogen, —SO$_2$—($C_1$-$C_6$) alkyl, CF$_3$, OCF$_3$, NO$_2$, CN, OH, phenyl $C_1$-$C_4$ alkyl wherein the phenyl is optionally substituted with 1, 2, 3, 4, or 5 groups that are independently selected from $C_1$-$C_4$ alkyl, $C_1$-$C_4$ alkoxy, CN, halogen, OH, and alkanoyl, $C_1$-$C_6$ alkoxy $C_1$-$C_6$ alkyl, $C_1$-$C_6$ alkoxycarbonyl, $C_1$-$C_6$ alkanoyl, NR$_7$R$_8$, or —C(O)NR$_7$R$_8$,
  wherein $R_7$ and $R_8$ are independently H or $C_1$-$C_6$ alkyl, wherein the $C_1$-$C_6$ alkyl is optionally substituted with 1, 2, or 3 groups that are independently $C_1$-$C_4$ alkoxycarbonyl, halogen, $C_1$-$C_6$ alkoxy, $C_1$-$C_6$ alkanoyl, NH$_2$, NH($C_1$-$C_6$ alkyl), N($C_1$-$C_6$ alkyl) ($C_1$-$C_6$ alkyl) or CO$_2$H;
  wherein the heterocycloalkyl portion of $R_5$ is further optionally substituted with =O, =N—OH, or =N—OCH$_3$.

Preferred compounds of Embodiment 49A include those of Embodiment 49C, i.e., compounds of Embodiment 49A where
$R_5$ is morpholinyl $C_1$-$C_4$ alkyl, piperidinyl $C_1$-$C_4$ alkyl, pyrrolidinyl $C_1$-$C_4$ alkyl, pyrazinyl $C_1$-$C_4$ alkyl, pyridyl $C_1$-$C_4$ alkyl, imidazolyl $C_1$-$C_4$ alkyl, furanyl $C_1$-$C_4$ alkyl, thienyl $C_1$-$C_4$ alkyl, or phenyl $C_1$-$C_4$ alkyl, wherein the cyclic portion of each of the above is unsubstituted or substituted with one or more groups that are independently $C_1$-$C_6$ alkyl, $C_1$-$C_6$ alkoxy, halogen, —SO$_2$—($C_1$-$C_6$) alkyl, CF$_3$, OCF$_3$, NO$_2$, CN, OH, phenyl $C_1$-$C_6$ alkyl wherein the phenyl is optionally substituted with 1, 2, 3, 4, or 5 groups that are independently selected from $C_1$-$C_4$ alkyl, $C_1$-$C_4$ alkoxy, CN, halogen, OH, and alkanoyl, $C_1$-$C_6$ alkoxy $C_1$-$C_6$ alkyl, $C_1$-$C_6$ alkoxycarbonyl, $C_1$-$C_6$ alkanoyl, $NR_7R_8$, or —C(O)$NR_7R_8$, wherein $R_7$ and $R_8$ are independently H or $C_1$-$C_6$ alkyl, wherein the $C_1$-$C_6$ alkyl is optionally substituted with 1, 2, or 3 groups that are independently $C_1$-$C_6$ alkoxycarbonyl, halogen, $C_1$-$C_6$ alkoxy, $C_1$-$C_6$ alkanoyl, $NH_2$, NH($C_1$-$C_6$ alkyl), N($C_1$-$C_6$ alkyl) ($C_1$-$C_6$ alkyl) or $CO_2H$;

wherein the heterocycloalkyl portion of $R_5$ is further optionally substituted with =O, =N—OH, or =N—$OCH_3$.

In still another aspect, the invention provides compounds according to embodiments 47, 48, 49, and 49A-49C, wherein $R_{21}$ is H.

In yet still another aspect, the invention provides compounds according to embodiments 47, 48, 49, and 49A-49C, wherein $R_{21}$ is CN.

In still yet another aspect, the invention provides compounds according to embodiments 47, 48, 49, and 49A-49C, wherein $R_{21}$ is amino, monoalkylamino, or dialkylamino.

In yet another aspect, the invention provides compounds of embodiments 47, 48, 49, and 49A-49C, wherein $R_{21}$ is OH.

In still another aspect, the invention provides compounds of embodiments 47, 48, 49, and 49A-49C, wherein $R_{21}$ is phenyl.

In still another aspect, the invention provides compounds of embodiments 47, 48, 49, and 49A-49C, wherein $R_{21}$ is pyridyl.

In still another aspect, the invention provides compounds of embodiments 47, 48, 49, and 49A-49C, wherein $R_{21}$ is halogen.

In yet another aspect, the invention provides compounds of embodiments 47, 48, 49, and 49A-49C, wherein $R_{21}$ is phenyl, which is substituted with 1-5 groups that are independently $C_1$-$C_6$ alkyl, $C_1$-$C_6$ alkoxy, halogen, OH, hydroxyl $C_1$-$C_4$ alkyl, haloalkyl (in one aspect, $CF_3$), or haloalkoxy (in one aspect, $OCF_3$)).

In yet still another aspect, the invention provides compounds of embodiments 47, 48, 49, and 49A-49C, wherein $R_{21}$ is pyridyl or pyrimidyl, each of which is optionally substituted with 1-5 groups that are independently $C_1$-$C_6$ alkyl, $C_1$-$C_6$ alkoxy, halogen, OH, hydroxyl $C_1$-$C_4$ alkyl, haloalkyl (in one aspect, $CF_3$), or haloalkoxy (in one aspect, $OCF_3$)).

In yet still another aspect, the invention provides compounds of embodiments 47, 48, 49, and 49A-49C, wherein $R_{21}$ is indolyl or (iso)quinolinyl, each of which is optionally substituted with 1-5 groups that are independently $C_1$-$C_6$ alkyl, $C_1$-$C_6$ alkoxy, halogen, OH, hydroxyl $C_1$-$C_4$ alkyl, haloalkyl (in one aspect, $CF_3$), or haloalkoxy (in one aspect, $OCF_3$)).

In still another aspect, the invention provides compounds of embodiments 47, 48, 49, and 49A-49C, wherein $R_{21}$ is $C_1$-$C_6$ alkyl, $C_2$-$C_6$ alkynyl, or $C_2$-$C_6$ alkenyl.

In still yet another aspect, the invention provides compounds of embodiments 45 and 45A-45F, wherein $R_{21}$ is —C(O)$NH_2$, —C(O)NH($C_1$-$C_6$ alkyl), or —C(O)N($C_1$-$C_6$ alkyl) ($C_1$-$C_6$ alkyl).

Preferred compounds of Embodiment 2 include those of Embodiment 50, i.e., compounds of Embodiment 2 where X is —C(O)$R_{20}$, or —$NR_xR_y$; wherein $R_{20}$ is OH or $C_1$-$C_6$ alkoxy; and $R_x$ and $R_y$ are independently H, $C_1$-$C_6$ alkyl, $C_1$-$C_6$ alkoxycarbonyl, phenyl $C_1$-$C_4$ alkoxycarbonyl, phenyl, naphthyl, phenyl $C_1$-$C_4$ alkyl, —C(O)-phenyl, —C(O)-naphthyl, pyridyl, pyrimidyl, pyrazinyl, benzofuranyl, indolyl, benzimidazolyl, thienyl, furanyl, quinolinyl, isoquinolinyl, pyridyl $C_1$-$C_6$ alkyl, pyrimidyl $C_1$-$C_6$ alkyl, pyrazinyl $C_1$-$C_6$ alkyl, benzofuranyl $C_1$-$C_6$ alkyl, indolyl $C_1$-$C_6$ alkyl, benzimidazolyl $C_1$-$C_6$ alkyl, thienyl $C_1$-$C_6$ alkyl, furanyl $C_1$-$C_6$ alkyl, quinolinyl $C_1$-$C_6$ alkyl, isoquinolinyl $C_1$-$C_6$ alkyl, or —C(O)-pyridyl, —C(O)-pyrimidyl, —C(O) -pyrazinyl, —C(O)-benzofuranyl, —C(O)-indolyl, —C(O)-benzimidazolyl, —C(O)-thienyl, —C(O)-furanyl, —C(O)-quinolinyl, or —C(O)-isoquinolinyl, wherein the ring portions of the above are optionally substituted with 1, 2, 3, 4, or 5 groups that are independently $C_1$-$C_6$ alkyl, $C_1$-$C_6$ alkoxy, halogen, $CO_2H$, $NR_6R_7$, —C(O)$NR_6R_7$, —($C_1$-$C_4$ alkyl)-$NR_6R_7$, —($C_1$-$C_4$ alkyl)-C(O)$NR_6R_7$, $CF_3$, or $OCF_3$.

Preferred compounds of Embodiment 50 include those of Embodiment 51, i.e., compounds of Embodiment 50 where $R_1$ is halogen, $C_1$-$C_6$ alkyl, $C_2$-$C_6$ alkynyl, $C_2$-$C_6$ alkenyl, each of which is unsubstituted or substituted with 1, 2, or 3 groups that are independently $C_1$-$C_6$ alkyl, halogen, $C_1$-$C_6$ alkoxy, OH, CN, $CO_2H$, heteroaryl selected from pyridyl, pyrimidyl, pyrazinyl, (iso)quinolinyl, indolyl, thienyl, furanyl, pyrrolyl, triazinyl, 1H-indazolyl, and benzimidazolyl, heterocycloalkyl selected from piperidinyl, pyrrolidinyl, tetrahydrofuranyl, tetrahydroisoquinolinyl, imidazolidinyl, piperazinyl, morpholinyl, and S,S-dioxomorpholinyl, phenyl, or naphthyl, wherein the heteroaryl, heterocycloalkyl, phenyl and naphthyl groups are optionally substituted with 1 or more groups that are independently selected from $C_1$-$C_4$ alkyl, $C_1$-$C_4$ alkoxy, halogen, OH, $CF_3$, and $OCF_3$, $CF_3$, $OCF_3$, —OC(O)—$C_1$-$C_6$ alkyl, $C_1$-$C_6$ alkoxycarbonyl, $C_1$-$C_6$ alkanoyl, —C(O)$R_{10}$, $NR_6R_7$, —($C_1$-$C_4$ alkyl)-$NR_6R_7$, or —C(O)$NR_6R_7$, wherein each $R_6$ and $R_7$ is independently H, $C_1$-$C_6$ alkyl, $C_1$-$C_4$ alkoxyalkyl, $C_1$-$C_6$ alkoxycarbonyl, wherein the alkyl portion of each is unsubstituted or substituted with 1, 2, or 3, groups that are independently halogen, OH, $C_1$-$C_4$ haloalkyl, $C_1$-$C_4$ haloalkoxy, $NH_2$, NH($C_1$-$C_6$ alkyl) or N($C_1$-$C_6$ alkyl) ($C_1$-$C_6$ alkyl);

$R_{10}$ is $C_2$-$C_6$ alkenyl, $C_2$-$C_6$ alkynyl, phenyl, naphthyl, pyridyl, quinolinyl, pyrimidyl, furanyl, indolyl, $C_3$-$C_8$ cycloalkyl, wherein the cyclic portions are optionally substituted with halogen, $C_1$-$C_6$ alkyl, $C_1$-$C_6$ alkoxy, OH, $CO_2H$, CN, $NO_2$, $C_1$-$C_4$ haloalkyl, or $C_1$-$C_4$ haloalkoxy;

wherein the cycloalkyl portion of $R_{10}$ is further optionally substituted with =O, =N—OH, or =N—$OCH_3$.

Preferred compounds of Embodiment 51 include those of Embodiment 52, i.e., compounds of Embodiment 51 where $R_4$ and $R_5$ and the nitrogen to which they are attached form a piperazinyl, morpholinyl, piperidinyl, thiomorpholinyl, imidazolidinyl, S,S,-dioxothiomorpholinyl, piperidinyl, pyrrolidinyl, ring, which is unsubstituted or substituted with 1 or more groups that are independently $C_1$-$C_6$ alkyl, $C_1$-$C_6$ alkoxy, halogen, phenyl $C_1$-$C_6$ alkyl, naphthyl $C_1$-$C_6$ alkyl, $C_1$-$C_6$ alkanoyl, OH, =O, pyridyl, pyrimidyl, pyrazinyl, pyrimidyl $C_1$-$C_6$ alkyl, pyrazinyl $C_1$-$C_6$ alkyl, phenyl, naphthyl, —$OCH_2CH_2O$—, or —$OCH_2O$—, wherein the pyridyl, pyrimidyl, pyrazinyl, pyrimidyl $C_1$-$C_6$ alkyl, phenyl and naphthyl groups are unsubstituted or substituted with 1 or more groups that are independently $C_1$-$C_4$ alkyl, $C_1$-$C_4$ alkoxy, halogen, $CF_3$ or $OCF_3$.

Preferred compounds of Embodiment 52 include those of Embodiment 53, i.e., compounds of Embodiment 52 where $R_1$ is halogen.

Preferred compounds of Embodiment 52 include those of Embodiment 54, i.e., compounds of Embodiment 52 where $R_1$ is $C_1$-$C_6$ alkyl, $C_2$-$C_6$ alkynyl, $C_2$-$C_6$ alkenyl, each of which is unsubstituted or substituted with 1, 2, or 3 groups that are independently $C_1$-$C_6$ alkyl, halogen, $C_1$-$C_6$ alkoxy, OH, CN, $CO_2H$, $CF_3$, $OCF_3$, —OC(O)—$C_1$-$C_6$ alkyl, $C_1$-$C_6$ alkoxycarbonyl, $C_1$-$C_6$ alkanoyl, —C(O)$R_{10}$, $NR_6R_7$, —($C_1$-$C_4$ alkyl)-$NR_6R_7$, —C(O)$NR_6R_7$, pyridyl, piperidinyl, or phenyl, wherein the phenyl is optionally substituted with 1 or more groups that are independently selected from $C_1$-$C_4$ alkyl, $C_1$-$C_4$ alkoxy, halogen, OH, $CF_3$, and $OCF_3$, wherein each $R_6$ and $R_7$ is independently H, $C_1$-$C_6$ alkyl, $C_1$-$C_4$ alkoxyalkyl, $C_1$-$C_6$ alkoxycarbonyl, wherein the alkyl portion of each is unsubstituted or substituted with 1, 2, or 3, groups that are independently halogen, OH, $C_1$-$C_4$ haloalkyl, $C_1$-$C_4$ haloalkoxy, $NH_2$, $NH(C_1$-$C_6$ alkyl) or $N(C_1$-$C_6$ alkyl) ($C_1$-$C_6$ alkyl);

$R_{10}$ is phenyl or pyridyl, each of which is optionally substituted with halogen, $C_1$-$C_6$ alkyl, $C_1$-$C_6$ alkoxy, OH, $CO_2H$, CN, $NO_2$, $CF_3$ or $OCF_3$.

Preferred compounds of Embodiment 54 include those of Embodiment 55, i.e., compounds of Embodiment 54 where $R_4$ and $R_5$ and the nitrogen to which they are attached form a piperazinyl, morpholinyl, piperidinyl, piperidinyl, or pyrrolidinyl ring, each of which is unsubstituted or substituted with 1 or more groups that are independently $C_1$-$C_6$ alkyl, $C_1$-$C_6$ alkoxy, halogen, phenyl $C_1$-$C_6$ alkyl, naphthyl $C_1$-$C_6$ alkyl, $C_1$-$C_6$ alkanoyl, OH, =O, pyridyl, pyrimidyl, pyrazinyl, pyrimidyl $C_1$-$C_6$ alkyl, pyrazinyl $C_1$-$C_6$ alkyl, phenyl, naphthyl, —OCH$_2$CH$_2$O—, or —OCH$_2$O—.

Preferred compounds of Embodiment 55 include those of Embodiment 56, i.e., compounds of Embodiment 55 where $R_1$ is $C_2$-$C_6$ alkynyl substituted with 1, 2, or 3 groups that are independently $C_1$-$C_6$ alkyl, halogen, $C_1$-$C_6$ alkoxy, OH, CN, $CO_2H$, $CF_3$, $OCF_3$, —OC(O)—$C_1$-$C_6$ alkyl, $C_1$-$C_6$ alkoxycarbonyl, $C_1$-$C_6$ alkanoyl, —C(O)$R_{10}$, $NR_6R_7$, —($C_1$-$C_4$ alkyl)-$NR_6R_7$, —C(O)$NR_6R_7$, pyridyl, piperidinyl, or phenyl, wherein the phenyl is optionally substituted with 1 or more groups that are independently selected from $C_1$-$C_4$ alkyl, $C_1$-$C_4$ alkoxy, halogen, OH, $CF_3$, and $OCF_3$, wherein each $R_6$ and $R_7$ is independently H, $C_1$-$C_6$ alkyl, $C_1$-$C_6$ alkoxycarbonyl, wherein the alkyl portion of each is unsubstituted or substituted with 1, or 2 groups that are independently halogen, OH, $CF_3$, $OCF_3$, $NH_2$, $NH(C_1$-$C_6$ alkyl) or $N(C_1$-$C_6$ alkyl) ($C_1$-$C_6$ alkyl)

Preferred compounds of Embodiment 55 include those of Embodiment 57, i.e., compounds of Embodiment 55 where $R_1$ is $C_1$-$C_6$ alkyl substituted with 1, 2, or 3 groups that are independently $C_1$-$C_6$ alkyl, halogen, $C_1$-$C_6$ alkoxy, OH, CN, $CO_2H$, $CF_3$, $OCF_3$, —OC(O)—$C_1$-$C_6$ alkyl, $C_1$-$C_6$ alkoxycarbonyl, $C_1$-$C_6$ alkanoyl, —C(O)$R_{10}$, $NR_6R_7$, —($C_1$-$C_4$ alkyl)-$NR_6R_7$, —C(O)$NR_6R_7$, pyridyl, piperidinyl, or phenyl, wherein the phenyl is optionally substituted with 1 or more groups that are independently selected from $C_1$-$C_4$ alkyl, $C_1$-$C_4$ alkoxy, halogen, OH, $CF_3$, and $OCF_3$, wherein each $R_6$ and $R_7$ is independently H, $C_1$-$C_6$ alkyl, $C_1$-$C_6$ alkoxycarbonyl, wherein the alkyl portion of each is unsubstituted or substituted with 1, or 2 groups that are independently halogen, OH, $CF_3$, $OCF_3$, $NH_2$, $NH(C_1$-$C_6$ alkyl) or $N(C_1$-$C_6$ alkyl) ($C_1$-$C_6$ alkyl).

Preferred compounds of Embodiment 55 include those of Embodiment 58, i.e., compounds of Embodiment 55 where $R_1$ is $C_1$-$C_6$ alkenyl substituted with 1, 2, or 3 groups that are independently $C_1$-$C_6$ alkyl, halogen, $C_1$-$C_6$ alkoxy, OH, CN, $CO_2H$, $CF_3$, $OCF_3$, —OC(O)—$C_1$-$C_6$ alkyl, $C_1$-$C_6$ alkoxycarbonyl, $C_1$-$C_6$ alkanoyl, —C(O)$R_{10}$, $NR_6R_7$, —($C_1$-$C_4$ alkyl)-$NR_6R_7$, —C(O)$NR_6R_7$, pyridyl, piperidinyl, or phenyl, wherein the phenyl is optionally substituted with 1 or more groups that are independently selected from $C_1$-$C_4$ alkyl, $C_1$-$C_4$ alkoxy, halogen, OH, $CF_3$, and $OCF_3$, wherein each $R_6$ and $R_7$ is independently H, $C_1$-$C_6$ alkyl, $C_1$-$C_6$ alkoxycarbonyl, wherein the alkyl portion of each is unsubstituted or substituted with 1, or 2 groups that are independently halogen, OH, $CF_3$, $OCF_3$, $NH_2$, $NH(C_1$-$C_6$ alkyl) or $N(C_1$-$C_6$ alkyl) ($C_1$-$C_6$ alkyl).

Preferred compounds of Embodiment 51 include those of Embodiment 59, i.e., compounds of Embodiment 51 where $R_4$ and $R_5$ are independently H, $C_1$-$C_6$ alkyl, $C_1$-$C_4$ alkoxy $C_1$-$C_6$ alkyl, $C_3$-$C_8$ cycloalkyl, piperidinyl, pyrrolidinyl, morpholinyl, morpholinyl $C_1$-$C_6$ alkyl, piperidinyl $C_1$-$C_6$ alkyl, pyrrolidinyl $C_1$-$C_6$ alkyl, piperidinyl $C_2$-$C_6$ alkenyl, pyrrolidinyl $C_2$-$C_6$ alkenyl, morpholinyl $C_2$-$C_6$ alkenyl, piperidinyl $C_2$-$C_6$ alkynyl, pyrrolidinyl $C_2$-$C_6$ alkynyl, morpholinyl $C_2$-$C_6$ alkynyl, phenyl, furanyl, pyridyl, pyrazinyl $C_1$-$C_6$ alkyl, pyridyl $C_1$-$C_6$ alkyl, imidazolyl $C_1$-$C_6$ alkyl, furanyl $C_1$-$C_6$ alkyl, thienyl $C_1$-$C_6$ alkyl, phenyl $C_1$-$C_6$ alkyl, phenyl $C_2$-$C_6$ alkenyl, phenyl $C_2$-$C_6$ alkynyl, wherein the cyclic portion of each of the above is unsubstituted or substituted with one or more groups that are independently $C_1$-$C_6$ alkyl, $C_1$-$C_6$ alkoxy, halogen, —SO$_2$—($C_1$-$C_6$) alkyl, $C_1$-$C_4$ haloalkyl, $C_1$-$C_4$ haloalkoxy, $NO_2$, CN, OH, phenyl $C_1$-$C_6$ alkyl wherein the phenyl is optionally substituted with 1, 2, 3, 4, or 5 groups that are independently selected from $C_1$-$C_4$ alkyl, $C_1$-$C_4$ alkoxy, CN, halogen, OH, and alkanoyl, $C_1$-$C_6$ alkoxy $C_1$-$C_6$ alkyl, $C_1$-$C_6$ alkoxycarbonyl, $C_1$-$C_6$ alkanoyl, $NR_7R_8$, or —C(O)$NR_7R_8$, wherein $R_7$ and $R_8$ are independently H or $C_1$-$C_6$ alkyl, wherein the $C_1$-$C_6$ alkyl is optionally substituted with 1, 2, or 3 groups that are independently $C_1$-$C_6$ alkoxycarbonyl, halogen, $C_1$-$C_6$ alkoxy, $C_1$-$C_6$ alkanoyl, $NH_2$, $NH(C_1$-$C_6$ alkyl), $N(C_1$-$C_6$ alkyl) ($C_1$-$C_6$ alkyl) or $CO_2H$;

wherein the heterocycloalkyl and the cycloalkyl portions of $R_4$ and $R_5$ are further optionally substituted with =O, =N—OH, or =N—OCH$_3$.

Preferred compounds of Embodiment 59 include those of Embodiment 60, i.e., compounds of Embodiment 59 where $R_1$ is $C_1$-$C_6$ alkyl, $C_2$-$C_6$ alkynyl, $C_2$-$C_6$ alkenyl, each of which is unsubstituted or substituted with 1, 2, or 3 groups that are independently $C_1$-$C_6$ alkyl, halogen, $C_1$-$C_6$ alkoxy, OH, CN, $CO_2H$, $CF_3$, $OCF_3$, —OC(O)—$C_1$-$C_6$ alkyl, $C_1$-$C_6$ alkoxycarbonyl, $C_1$-$C_6$ alkanoyl, —C(O)$R_{10}$, $NR_6R_7$, —($C_1$-$C_4$ alkyl)-$NR_6R_7$, —C(O)$NR_6R_7$, pyridyl, piperidinyl, or phenyl, wherein the phenyl is optionally substituted with 1 or more groups that are independently selected from $C_1$-$C_4$ alkyl, $C_1$-$C_4$ alkoxy, halogen, OH, $CF_3$, and $OCF_3$, wherein each $R_6$ and $R_7$ is independently H, $C_1$-$C_6$ alkyl, $C_1$-$C_4$ alkoxyalkyl, $C_1$-$C_6$ alkoxycarbonyl, wherein the alkyl portion of each is unsubstituted or substituted with 1, 2, or 3, groups that are independently halogen, OH, $C_1$-$C_4$ haloalkyl, $C_1$-$C_4$ haloalkoxy, $NH_2$, $NH(C_1$-$C_6$ alkyl) or $N(C_1$-$C_6$ alkyl) $(C_1$-$C_6$ alkyl);

$R_{10}$ is phenyl or pyridyl, each of which is optionally substituted with halogen, $C_1$-$C_6$ alkyl, $C_1$-$C_6$ alkoxy, OH, $CO_2H$, CN, $NO_2$, $CF_3$ or $OCF_3$.

Preferred compounds of Embodiment 60 include those of Embodiment 61, i.e., compounds of Embodiment 60 where $R_4$ and $R_5$ are independently H, $C_1$-$C_6$ alkyl, $C_1$-$C_4$ alkoxy $C_1$-$C_6$ alkyl, piperidinyl, pyrrolidinyl, morpholinyl, morpholinyl $C_1$-$C_6$ alkyl, piperidinyl $C_1$-$C_6$ alkyl, pyrrolidinyl $C_1$-$C_6$ alkyl, phenyl, furanyl, pyridyl, pyrazinyl $C_1$-$C_6$ alkyl, pyridyl $C_1$-$C_6$ alkyl, imidazolyl $C_1$-$C_6$ alkyl, furanyl $C_1$-$C_6$ alkyl, thienyl $C_1$-$C_6$ alkyl, phenyl $C_1$-$C_6$ alkyl, wherein the cyclic portion of each of the above is unsubstituted or substituted with one or more groups that are independently $C_1$-$C_6$ alkyl, $C_1$-$C_6$ alkoxy, halogen, —$SO_2$—$(C_1$-$C_6)$ alkyl, $C_1$-$C_4$ haloalkyl, $C_1$-$C_4$ haloalkoxy, $NO_2$, CN, OH, phenyl $C_1$-$C_6$ alkyl wherein the phenyl is optionally substituted with 1, 2, 3, 4, or 5 groups that are independently selected from $C_1$-$C_4$ alkyl, $C_1$-$C_4$ alkoxy, CN, halogen, OH, and alkanoyl, $C_1$-$C_6$ alkoxy $C_1$-$C_6$ alkyl, $C_1$-$C_6$ alkoxycarbonyl, $C_1$-$C_6$ alkanoyl, $NR_7R_8$, or —$C(O)NR_7R_8$, wherein $R_7$ and $R_8$ are independently H or $C_1$-$C_6$ alkyl, wherein the $C_1$-$C_6$ alkyl is optionally substituted with 1, 2, or 3 groups that are independently $C_1$-$C_6$ alkoxycarbonyl, halogen, $C_1$-$C_6$ alkoxy, $C_1$-$C_6$ alkanoyl, $NH_2$, $NH(C_1$-$C_6$ alkyl), $N(C_1$-$C_6$ alkyl) $(C_1$-$C_6$ alkyl) or $CO_2H$;

wherein the heterocycloalkyl and the cycloalkyl portions of $R_4$ and $R_5$ are further optionally substituted with =O, =N—OH, or =N—$OCH_3$.

Preferred compounds of Embodiment 61 include those of Embodiment 62, i.e., compounds of Embodiment 61 where $R_1$ is $C_2$-$C_6$ alkynyl substituted with 1, 2, or 3 groups that are independently $C_1$-$C_6$ alkyl, halogen, $C_1$-$C_6$ alkoxy, OH, CN, $CO_2H$, $CF_3$, $OCF_3$, —OC(O)—$C_1$-$C_6$ alkyl, $C_1$-$C_6$ alkoxycarbonyl, $C_1$-$C_6$ alkanoyl, —$C(O)R_{10}$, $NR_6R_7$, —$(C_1$-$C_4$ alkyl)-$NR_6R_7$, —$C(O)NR_6R_7$, pyridyl, piperidinyl, or phenyl, wherein the phenyl is optionally substituted with 1 or more groups that are independently selected from $C_1$-$C_4$ alkyl, $C_1$-$C_4$ alkoxy, halogen, OH, $CF_3$, and $OCF_3$, wherein each $R_6$ and $R_7$ is independently H, $C_1$-$C_6$ alkyl, $C_1$-$C_6$ alkoxycarbonyl, wherein the alkyl portion of each is unsubstituted or substituted with 1, or 2 groups that are independently halogen, OH, $CF_3$, $OCF_3$, $NH_2$, $NH(C_1$-$C_6$ alkyl) or $N(C_1$-$C_6$ alkyl) $(C_1$-$C_6$ alkyl)

Preferred compounds of Embodiment 61 include those of Embodiment 63, i.e., compounds of Embodiment 61 where $R_1$ is $C_1$-$C_6$ alkyl substituted with 1, 2, or 3 groups that are independently $C_1$-$C_6$ alkyl, halogen, $C_1$-$C_6$ alkoxy, OH, CN, $CO_2H$, $CF_3$, $OCF_3$, —OC(O)—$C_1$-$C_6$ alkyl, $C_1$-$C_6$ alkoxycarbonyl, $C_1$-$C_6$ alkanoyl, —$C(O)R_{10}$, $NR_6R_7$, —$(C_1$-$C_4$ alkyl) —$NR_6R_7$, —$C(O)NR_6R_7$, pyridyl, piperidinyl, or phenyl, wherein the phenyl is optionally substituted with 1 or more groups that are independently selected from $C_1$-$C_4$ alkyl, $C_1$-$C_4$ alkoxy, halogen, OH, $CF_3$, and $OCF_3$, wherein each $R_6$ and $R_7$ is independently H, $C_1$-$C_6$ alkyl, $C_1$-$C_6$ alkoxycarbonyl, wherein the alkyl portion of each is unsubstituted or substituted with 1, or 2 groups that are independently halogen, OH, $CF_3$, $OCF_3$, $NH_2$, $NH(C_1$-$C_6$ alkyl) or $N(C_1$-$C_6$ alkyl) $(C_1$-$C_6$ alkyl).

Preferred compounds of Embodiment 61 include those of Embodiment 64, i.e., compounds of Embodiment 61 where $R_1$ is $C_1$-$C_6$ alkenyl substituted with 1, 2, or 3 groups that are independently $C_1$-$C_6$ alkyl, halogen, $C_1$-$C_6$ alkoxy, OH, CN, $CO_2H$, $CF_3$, $OCF_3$, —OC(O)—$C_1$-$C_6$ alkyl, $C_1$-$C_6$ alkoxycarbonyl, $C_1$-$C_6$ alkanoyl, —$C(O)R_{10}$, $NR_6R_7$, —$(C_1$-$C_4$ alkyl)-$NR_6R_7$, —$C(O)NR_6R_7$, pyridyl, piperidinyl, or phenyl, wherein the phenyl is optionally substituted with 1 or more groups that are independently selected from $C_1$-$C_4$ alkyl, $C_1$-$C_4$ alkoxy, halogen, OH, $CF_3$, and $OCF_3$, wherein each $R_6$ and $R_7$ is independently H, $C_1$-$C_6$ alkyl, $C_1$-$C_6$ alkoxycarbonyl, wherein the alkyl portion of each is unsubstituted or substituted with 1, or 2 groups that are independently halogen, OH, $CF_3$, $OCF_3$, $NH_2$, $NH(C_1$-$C_6$ alkyl) or $N(C_1$-$C_6$ alkyl) $(C_1$-$C_6$ alkyl)

Preferred compounds of Embodiment 51 include those of Embodiment 65, i.e., compounds of Embodiment 51 where $R_4$ and $R_5$ are independently H, $C_1$-$C_6$ alkyl, or $C_3$-$C_6$ cycloalkyl, wherein the cycloalkyl is unsubstituted or substituted with one or more groups that are independently $C_1$-$C_6$ alkyl, $C_1$-$C_6$ alkoxy, halogen, —$SO_2$—$(C_1$-$C_6)$ alkyl, $C_1$-$C_4$ haloalkyl, $C_1$-$C_4$ haloalkoxy, $NO_2$, CN, OH, phenyl $C_1$-$C_6$ alkyl wherein the phenyl is optionally substituted with 1, 2, 3, 4, or 5 groups that are independently selected from $C_1$-$C_4$ alkyl, $C_1$-$C_4$ alkoxy, CN, halogen, OH, and alkanoyl, $C_1$-$C_6$ alkoxy $C_1$-$C_6$ alkyl, $C_1$-$C_6$ alkoxycarbonyl, $C_1$-$C_6$ alkanoyl, $NR_7R_8$, or —$C(O)NR_7R_8$, wherein $R_7$ and $R_8$ are independently H or $C_1$-$C_6$ alkyl, wherein the $C_1$-$C_6$ alkyl is optionally substituted with 1, 2, or 3 groups that are independently $C_1$-$C_6$ alkoxycarbonyl, halogen, $C_1$-$C_6$ alkoxy, $C_1$-$C_6$ alkanoyl, $NH_2$, $NH(C_1$-$C_6$ alkyl), $N(C_1$-$C_6$ alkyl) $(C_1$-$C_6$ alkyl) or $CO_2H$;

wherein the cycloalkyl portion of $R_4$ and $R_5$ is further optionally substituted with =O, =N-OH, or =N—$OCH_3$.

Preferred compounds of Embodiment 65 include those of Embodiment 66, i.e., compounds of Embodiment 65 where $R_1$ is $C_1$-$C_6$ alkyl, $C_2$-$C_6$ alkynyl, $C_2$-$C_6$ alkenyl, each of which is unsubstituted or substituted with 1, 2, or 3 groups that are independently $C_1$-$C_6$ alkyl, halogen, $C_1$-$C_6$ alkoxy, OH, CN, $CO_2H$, $CF_3$, $OCF_3$, —OC(O)—$C_1$-$C_6$ alkyl, $C_1$-$C_6$ alkoxycarbonyl, $C_1$-$C_6$ alkahoyl, —$C(O)R_{10}$, $NR_6R_7$, —$(C_1$-$C_4$ alkyl)-$NR_6R_7$, —$C(O)NR_6R_7$, pyridyl, piperidinyl, or phenyl, wherein the phenyl is optionally substituted with 1 or more groups that are independently selected from $C_1$-$C_4$ alkyl, $C_1$-$C_4$ alkoxy, halogen, OH, $CF_3$, and $OCF_3$, wherein each $R_6$ and $R_7$ is independently H, $C_1$-$C_6$ alkyl, $C_1$-$C_4$ alkoxyalkyl, $C_1$-$C_6$ alkoxycarbonyl, wherein the alkyl portion of each is unsubstituted or substituted with 1, 2, or 3, groups that are independently halogen, OH, $C_1$-$C_4$ haloalkyl, $C_1$-$C_4$ haloalkoxy, $NH_2$, $NH(C_1$-$C_6$ alkyl) or $N(C_1$-$C_6$ alkyl) $(C_1$-$C_6$ alkyl);

$R_{10}$ is phenyl or pyridyl, each of which is optionally substituted with halogen, $C_1$-$C_6$ alkyl, $C_1$-$C_6$ alkoxy, OH, $CO_2H$, CN, $NO_2$, $CF_3$ or $OCF_3$.

Preferred compounds of Embodiment 66 include those of Embodiment 67, i.e., compounds of Embodiment 66 where $R_1$ is $C_2$-$C_6$ alkynyl substituted with 1, 2, or 3 groups that are independently $C_1$-$C_6$ alkyl, halogen, $C_1$-$C_6$ alkoxy, OH, CN, $CO_2H$, $CF_3$, $OCF_3$, —OC(O)—$C_1$-$C_6$ alkyl, $C_1$-$C_6$ alkoxycarbonyl, $C_1$-$C_6$ alkanoyl, —C(O)$R_{10}$, $NR_6R_7$, —($C_1$-$C_4$ alkyl)-$NR_6R_7$, —C(O)$NR_6R_7$, pyridyl, piperidinyl, or phenyl,
  wherein the phenyl is optionally substituted with 1 or more groups that are independently selected from $C_1$-$C_4$ alkyl, $C_1$-$C_4$ alkoxy, halogen, OH, $CF_3$, and $OCF_3$, wherein
  each $R_6$ and $R_7$ is independently H, $C_1$-$C_6$ alkyl, $C_1$-$C_6$ alkoxycarbonyl, wherein the alkyl portion of each is unsubstituted or substituted with 1, or 2 groups that are independently halogen, OH, $CF_3$, $OCF_3$, $NH_2$, NH($C_1$-$C_6$ alkyl) or N($C_1$-$C_6$ alkyl) ($C_1$-$C_6$ alkyl).

Preferred compounds of Embodiment 66 include those of Embodiment 68, i.e., compounds of Embodiment 66 where $R_1$ is $C_1$-$C_6$ alkyl substituted with 1, 2, or 3 groups that are independently $C_1$-$C_6$ alkyl, halogen, $C_1$-$C_6$ alkoxy, OH, CN, $CO_2$H, $CF_3$, $OCF_3$, —OC(O)—$C_1$-$C_6$ alkyl, $C_1$-$C_6$ alkoxycarbonyl, $C_1$-$C_6$ alkanoyl, —C(O)$R_{10}$, $NR_6R_7$, —($C_1$-$C_4$ alkyl)-$NR_6R_7$, —C(O)$NR_6R_7$, pyridyl, piperidinyl, or phenyl,
  wherein the phenyl is optionally substituted with 1 or more groups that are independently selected from $C_1$-$C_4$ alkyl, $C_1$-$C_4$ alkoxy, halogen, OH, $CF_3$, and $OCF_3$, wherein
  each $R_6$ and $R_7$ is independently H, $C_1$-$C_6$ alkyl, $C_1$-$C_6$ alkoxycarbonyl, wherein the alkyl portion of each is unsubstituted or substituted with 1, or 2 groups that are independently halogen, OH, $CF_3$, $OCF_3$, $NH_2$, NH($C_1$-$C_6$ alkyl) or N($C_1$-$C_6$ alkyl) ($C_1$-$C_6$ alkyl)

Preferred compounds of Embodiment 66 include those of Embodiment 69, i.e., compounds of Embodiment 66 where $R_1$ is $C_1$-$C_6$ alkenyl substituted with 1, 2, or 3 groups that are independently $C_1$-$C_6$ alkyl, halogen, $C_1$-$C_6$ alkoxy, OH, CN, $CO_2$H, $CF_3$, $OCF_3$, —OC(O)—$C_1$-$C_6$ alkyl, $C_1$-$C_6$ alkoxycarbonyl, $C_1$-$C_6$ alkanoyl, —C(O)$R_{10}$, $NR_6R_7$, —($C_1$-$C_4$ alkyl)-$NR_6R_7$, —C(O)$NR_6R_7$, pyridyl, piperidinyl, or phenyl,
  wherein the phenyl is optionally substituted with 1 or more groups that are independently selected from $C_1$-$C_4$ alkyl, $C_1$-$C_4$ alkoxy, halogen, OH, $CF_3$, and $OCF_3$, wherein
  each $R_6$ and $R_7$ is independently H, $C_1$-$C_6$ alkyl, $C_1$-$C_6$ alkoxycarbonyl, wherein the alkyl portion of each is unsubstituted or substituted with 1, or 2 groups that are independently halogen, OH, $CF_3$, $OCF_3$, $NH_2$, NH($C_1$-$C_6$ alkyl) or N($C_1$-$C_6$ alkyl) ($C_1$-$C_6$ alkyl).

Preferred compounds of Embodiment 65 include those of Embodiment 70, i.e., compounds of Embodiment 65 where $R_1$ is halogen.

Preferred compounds of Embodiment 50 include those of Embodiment 70A, i.e., compounds of Embodiment 50 where Z is a bond.

Preferred compounds of Embodiment 50 include those of Embodiment 70B, i.e., compounds of Embodiment 50 where Z is —$CH_2$—.

Preferred compounds of Embodiment 50 include those of Embodiment 70C, i.e., compounds of Embodiment 50 where Z is —NH—.

Preferred compounds of Embodiment 50 include those of Embodiment 70D, i.e., compounds of Embodiment 50 where Z is —S— or —$SO_2$—.

Preferred compounds of Embodiment 50 include those of Embodiment 70E, i.e., compounds of Embodiment 50 where Z is —N($C_1$-$C_4$ alkyl)-. In another aspect, Z is —N($C_1$-$C_2$ alkyl)-. In still another aspect, Z is —N($C_2$-$C_3$ alkyl)-.

Preferred compounds of Embodiment 50 include those of Embodiment 70F, i.e., compounds of Embodiment 50 where Z is —$SO_2$NH—, or —$SO_2$N($C_1$-$C_4$ alkyl)-.

In still another aspect, the invention provides compounds according to embodiment 50, wherein $R_{21}$ is H.

In yet still another aspect, the invention provides compounds according to embodiment 50, wherein $R_{21}$ is CN.

In still yet another aspect, the invention provides compounds according to embodiment 50, wherein $R_{21}$ is amino, monoalkylamino, or dialkylamino.

In yet another aspect, the invention provides compounds of embodiment 50, wherein $R_{21}$ is OH.

In still another aspect, the invention provides compounds of embodiment 50, wherein $R_{21}$ is phenyl.

In still another aspect, the invention provides compounds of embodiment 50, wherein $R_{21}$ is pyridyl.

In still another aspect, the invention provides compounds of embodiment 50, wherein $R_{21}$ is halogen.

In yet another aspect, the invention provides compounds of embodiment 50, wherein $R_{21}$ is phenyl, which is substituted with 1-5 groups that are independently $C_1$-$C_6$ alkyl, $C_1$-$C_6$ alkoxy, halogen, OH, hydroxyl $C_1$-$C_4$ alkyl, haloalkyl (in one aspect, $CF_3$), or haloalkoxy (in one aspect, $OCF_3$)).

In yet still another aspect, the invention provides compounds of embodiment 50, wherein $R_{21}$ is pyridyl or pyrimidyl, each of which is optionally substituted with 1-5 groups that are independently $C_1$-$C_6$ alkyl, $C_1$-$C_6$ alkoxy, halogen, OH, hydroxyl $C_1$-$C_4$ alkyl, haloalkyl (in one aspect, $CF_3$), or haloalkoxy (in one aspect, $OCF_3$)).

In yet still another aspect, the invention provides compounds of embodiment 50, wherein $R_{21}$ is indolyl or (iso)quinolinyl, each of which is optionally substituted with 1-5 groups that are independently $C_1$-$C_6$ alkyl, $C_1$-$C_6$ alkoxy, halogen, OH, hydroxyl $C_1$-$C_4$ alkyl, haloalkyl (in one aspect, $CF_3$), or haloalkoxy (in one aspect, $OCF_3$)).

In still another aspect, the invention provides compounds of embodiment 50, wherein $R_{21}$ is $C_1$-$C_6$ alkyl, $C_2$-$C_6$ alkynyl, or $C_2$-$C_6$ alkenyl.

In still yet another aspect, the invention provides compounds of embodiment 50, wherein $R_{21}$ is —C(O)$NH_2$, —C(O)NH($C_1$-$C_6$ alkyl), or —C(O)N($C_1$-$C_6$ alkyl) ($C_1$-$C_6$ alkyl).

Preferred compounds of Embodiment 51 include those of Embodiment 71, i.e., compounds of Embodiment 51 where
  Z is a bond;
  $R_1$ is phenyl, naphthyl, thienyl, furanyl, indolyl, pyridyl, pyridazinyl, pyrimidyl, pyrazinyl, triazolyl, imidazolyl, benzofuranyl, piperidinyl, pyrrolidinyl, piperazinyl, or morpholinyl, each of which is unsubstituted or substituted with 1, 2, 3, 4, or 5 groups that are independently $C_1$-$C_6$ alkyl, halogen, $C_1$-$C_6$ alkoxy, OH, CN, $CO_2$H, $C_1$-$C_4$ haloalkyl, $C_1$-$C_4$ haloalkoxy, —OC(O)—$C_1$-$C_6$ alkyl, $C_1$-$C_6$ alkoxycarbonyl, $C_1$-$C_6$ alkanoyl, —C(O)$R_{10}$, $NR_6R_7$, —($C_1$-$C_4$ alkyl)-$NR_6R_7$, —C(O)$NR_6R_7$, heteroaryl selected from pyridyl, pyrimidyl, pyrazinyl, indolyl, thienyl, furanyl, pyrrolyl, and benzimidazolyl, heterocycloalkyl selected from piperidinyl, pyrrolidinyl, piperazinyl, morpholinyl, and phenyl, naphthyl, wherein the heteroaryl, heterocycloalkyl, phenyl and naphthyl groups are optionally substituted with or phenyl, which is optionally substituted with 1, 2, 3, 4, or 5 groups that are independently selected from $C_1$-$C_4$ alkyl, $C_1$-$C_4$ alkoxy, halogen, $CF_3$, and $OCF_3$, wherein
  each $R_6$ and $R_7$ is independently H, $C_1$-$C_6$ alkyl, $C_1$-$C_4$ alkoxyalkyl, $C_1$-$C_6$ alkoxycarbonyl, wherein the alkyl portion of each is unsubstituted or substituted with 1, 2, or 3, groups that are independently halogen, OH, $C_1$-$C_4$ haloalkyl, $C_1$-$C_4$ haloalkoxy, $NH_2$, $NH(C_1$-$C_6$ alkyl) or $N(C_1$-$C_6$ alkyl) ($C_1$-$C_6$ alkyl); and $R_{10}$ is $C_2$-$C_6$ alkenyl, $C_2$-$C_6$ alkynyl, phenyl, naphthyl, pyridyl, quinolinyl, pyrimidyl, furanyl, indolyl, $C_3$-$C_8$ cycloalkyl, wherein the cyclic portions are optionally substituted with halogen, $C_1$-$C_6$ alkyl, $C_1$-$C_6$ alkoxy, OH, $CO_2H$, CN, $NO_2$, $C_1$-$C_4$ haloalkyl, or $C_1$-$C_4$ haloalkoxy;

wherein the heterocycloalkyl and the cycloalkyl portions of $R_1$ and $R_{10}$ are further optionally substituted with =O, =N—OH, or =N—$OCH_3$.

Preferred compounds of Embodiment 71 include those of Embodiment 72, i.e., compounds of Embodiment 71 where $R_4$ and $R_5$ and the nitrogen to which they are attached form a piperazinyl, morpholinyl, piperidinyl, imidazolidinyl, or pyrrolidinyl ring, each of which is unsubstituted or substituted with 1 or more groups that are independently $C_1$-$C_4$ alkyl, $C_1$-$C_4$ alkoxy, halogen, phenyl $C_1$-$C_4$ alkyl, $C_1$-$C_6$ alkanoyl, OH, pyridyl, pyrimidyl, pyrazinyl, pyrimidyl $C_1$-$C_4$ alkyl, pyrazinyl $C_1$-$C_4$ alkyl, phenyl, —$OCH_2CH_2O$—, —$OCH_2O$—, wherein the pyridyl, pyrimidyl, pyrazinyl, pyrimidyl $C_1$-$C_6$ alkyl, and phenyl groups are unsubstituted or substituted with 1 or more groups that are independently $C_1$-$C_4$ alkyl, $C_1$-$C_4$ alkoxy, halogen, $CF_3$ or $OCF_3$.

Preferred compounds of Embodiment 72 include those of Embodiment 73, i.e., compounds of Embodiment 72 where $R_1$ is phenyl which is unsubstituted or substituted with 1, 2, 3, 4, or 5 groups that are independently $C_1$-$C_6$ alkyl, halogen, $C_1$-$C_6$ alkoxy, OH, CN, $CO_2H$, $C_1$-$C_4$ haloalkyl, $C_1$-$C_4$ haloalkoxy, —OC(O)—$C_1$-$C_6$ alkyl, $C_1$-$C_6$ alkoxycarbonyl, $C_1$-$C_6$ alkanoyl, —C(O)$R_{10}$, $NR_6R_7$, —($C_1$-$C_4$ alkyl)-$NR_6R_7$, —C(O)$NR_6R_7$, pyridyl, piperidinyl, or phenyl, which is optionally substituted with 1, 2, 3, 4, or 5 groups that are independently selected from $C_1$-$C_4$ alkyl, $C_1$-$C_4$ alkoxy, halogen, $CF_3$, and $OCF_3$, wherein each $R_6$ and $R_7$ is independently H, $C_1$-$C_6$ alkyl, $C_1$-$C_4$ alkoxyalkyl, $C_1$-$C_6$ alkoxycarbonyl, wherein the alkyl portion of each is unsubstituted or substituted with 1, 2, or 3, groups that are independently halogen, OH, $CF_3$, $OCF_3$, $NH_2$, $NH(C_1$-$C_6$ alkyl) or $N(C_1$-$C_6$ alkyl) ($C_1$-$C_6$ alkyl).

Preferred compounds of Embodiment 73 include those of Embodiment 74, i.e., compounds of Embodiment 73 where $R_2$ and $R_3$ are both H; and $R_4$ and $R_5$ and the nitrogen to which they are attached form a piperazinyl, morpholinyl, piperidinyl, or pyrrolidinyl ring, each of which is substituted with 1 or more groups that are independently $C_1$-$C_4$ alkyl, $C_1$-$C_4$ alkoxy, halogen, phenyl $C_1$-$C_4$ alkyl, $C_1$-$C_6$ alkanoyl, OH, pyridyl, pyrimidyl, pyrazinyl, pyrimidyl $C_1$-$C_4$ alkyl, pyrazinyl $C_1$-$C_4$ alkyl, phenyl, —$OCH_2CH_2O$—, or —$OCH_2O$—.

Preferred compounds of Embodiment 72 include those of Embodiment 75, i.e., compounds of Embodiment 72 where $R_1$ is thienyl, furanyl, indolyl, pyridyl, pyridazinyl, pyrimidyl, pyrazinyl, triazolyl, imidazolyl, benzofuranyl, piperidinyl, pyrrolidinyl, piperazinyl, or morpholinyl, each of which is unsubstituted or substituted with 1, 2, 3, or 4 groups that are independently $C_1$-$C_6$ alkyl, halogen, $C_1$-$C_6$ alkoxy, OH, CN, $CO_2H$, $CF_3$, $OCF_3$, —OC(O)—$C_1$-$C_6$ alkyl, $C_1$-$C_6$ alkoxycarbonyl, $C_1$-$C_6$ alkanoyl, $NR_6R_7$, —($C_1$-$C_4$ alkyl) —$NR_6R_7$, —C(O)$NR_6R_7$, pyridyl, piperidinyl, or phenyl, which is optionally substituted with 1, 2, 3, 4, or 5 groups that are independently selected from $C_1$-$C_4$ alkyl, $C_1$-$C_4$ alkoxy, halogen, $CF_3$, and $OCF_3$, wherein each $R_6$ and $R_7$ is independently H, $C_1$-$C_6$ alkyl, $C_1$-$C_4$ alkoxyalkyl, $C_1$-$C_6$ alkoxycarbonyl, wherein the alkyl portion of each is unsubstituted or substituted with 1, 2, or 3, groups that are independently halogen, OH, $C_1$-$C_4$ haloalkyl, $C_1$-$C_4$ haloalkoxy, $NH_2$, $NH(C_1$-$C_6$ alkyl) or $N(C_1$-$C_6$ alkyl) ($C_1$-$C_6$ alkyl); and wherein the heterocycloalkyl portion of $R_{10}$ is further optionally substituted with =O, =N—OH, or =N—$OCH_3$.

Preferred compounds of Embodiment 75 include those of Embodiment 76, i.e., compounds of Embodiment 75 where $R_2$ and $R_3$ are both H; and $R_4$ and $R_5$ and the nitrogen to which they are attached form a piperazinyl, morpholinyl, piperidinyl, or pyrrolidinyl ring, each of which is substituted with 1 or more groups that are independently $C_1$-$C_4$ alkyl, $C_1$-$C_4$ alkoxy, halogen, phenyl $C_1$-$C_4$ alkyl, $C_1$-$C_6$ alkanoyl, OH, pyridyl, pyrimidyl, pyrazinyl, pyrimidyl $C_1$-$C_4$ alkyl, pyrazinyl $C_1$-$C_4$ alkyl, phenyl, —$OCH_2CH_2O$—, or —$OCH_2O$—.

Preferred compounds of Embodiment 76 include those of Embodiment 77, i.e., compounds of Embodiment 76 where $R_1$ is thienyl optionally substituted with 1, 2, 3, or 4 groups that are independently $C_1$-$C_6$ alkyl, halogen, $C_1$-$C_6$ alkoxy, OH, CN, $CO_2H$, $CF_3$, $OCF_3$, —OC(O)—$C_1$-$C_6$ alkyl, $C_1$-$C_6$ alkoxycarbonyl, $C_1$-$C_6$ alkanoyl, $NR_6R_7$, —($C_1$-$C_4$ alkyl)-$NR_6R_7$, —C(O)$NR_6R_7$, pyridyl, piperidinyl, or phenyl, which is optionally substituted with 1, 2, 3, 4, or 5 groups that are independently selected from $C_1$-$C_4$ alkyl, $C_1$-$C_4$ alkoxy, halogen, $CF_3$, and $OCF_3$, wherein each $R_6$ and $R_7$ is independently H, $C_1$-$C_6$ alkyl, $C_1$-$C_4$ alkoxyalkyl, $C_1$-$C_6$ alkoxycarbonyl, wherein the alkyl portion of each is unsubstituted or substituted with 1, 2, or 3, groups that are independently halogen, OH, $C_1$-$C_4$ haloalkyl, $C_1$-$C_4$ haloalkoxy, $NH_2$, $NH(C_1$-$C_6$ alkyl) or $N(C_1$-$C_6$ alkyl) ($C_1$-$C_6$ alkyl).

Preferred compounds of Embodiment 76 include those of Embodiment 78, i.e., compounds of Embodiment 76 where $R_1$ is benzofuranyl optionally substituted with 1, 2, 3, or 4 groups that are independently $C_1$-$C_6$ alkyl, halogen, $C_1$-$C_6$ alkoxy, OH, CN, $CO_2H$, $CF_3$, $OCF_3$, —OC(O)— $C_1$-$C_6$ alkyl, $C_1$-$C_6$ alkoxycarbonyl, $C_1$-$C_6$ alkanoyl, $NR_6R_7$, —($C_1$-$C_4$ alkyl)-$NR_6R_7$, —C(O)$NR_6R_7$, pyridyl, piperidinyl, or phenyl, which is optionally substituted with 1, 2, 3, 4, or 5 groups that are independently selected from $C_1$-$C_4$ alkyl, $C_1$-$C_4$ alkoxy, halogen, $CF_3$, and $OCF_3$, wherein each $R_6$ and $R_7$ is independently H, $C_1$-$C_6$ alkyl, $C_1$-$C_4$ alkoxyalkyl, $C_1$-$C_6$ alkoxycarbonyl, wherein the alkyl portion of each is unsubstituted or substituted with 1, 2, or 3, groups that are independently halogen, OH, $C_1$-$C_4$ haloalkyl, $C_1$-$C_4$ haloalkoxy, $NH_2$, $NH(C_1$-$C_6$ alkyl) or $N(C_1$-$C_6$ alkyl) ($C_1$-$C_6$ alkyl).

Preferred compounds of Embodiment 71 include those of Embodiment 78, i.e., compounds of Embodiment 71 where $R_4$ and $R_5$ are independently H, $C_1$-$C_6$ alkyl, $C_1$-$C_4$ alkoxy $C_1$-$C_6$ alkyl, $C_3$-$C_8$ cycloalkyl, piperidinyl, pyrrolidinyl, morpholinyl, morpholinyl $C_1$-$C_6$ alkyl, piperidinyl $C_1$-$C_6$ alkyl, pyrrolidinyl $C_1$-$C_6$ alkyl, piperidinyl $C_2$-$C_6$ alkenyl, pyrrolidinyl $C_2$-$C_6$ alkenyl, morpholinyl $C_2$-$C_6$ alkenyl, piperidinyl $C_2$-$C_6$ alkynyl, pyrrolidinyl $C_2$-$C_6$ alkynyl, morpholinyl $C_2$-$C_6$ alkynyl, phenyl, furanyl, pyridyl, pyrazinyl $C_1$-$C_6$ alkyl, pyridyl $C_1$-$C_6$ alkyl, imidazolyl $C_1$-$C_6$ alkyl, furanyl $C_1$-$C_6$ alkyl, thienyl $C_1$-$C_6$ alkyl, phenyl $C_1$-$C_6$ alkyl, phenyl $C_2$-$C_6$ alkenyl, phenyl $C_2$-$C_6$ alkynyl, or $C_3$-$C_8$ cycloalkyl, wherein the cyclic portion of each of the above is unsubstituted or substituted with one or more groups that are independently $C_1$-$C_6$ alkyl, $C_1$-$C_6$ alkoxy, halogen, —$SO_2$—($C_1$-$C_6$) alkyl, $C_1$-$C_4$ haloalkyl, $C_1$-$C_4$ haloalkoxy, $NO_2$, CN, OH, phenyl $C_1$-$C_6$ alkyl wherein the phenyl is optionally substituted with 1, 2, 3, 4, or 5 groups that are independently selected from $C_1$-$C_4$ alkyl, $C_1$-$C_4$ alkoxy, CN, halogen, OH, and alkanoyl, $C_1$-$C_6$ alkoxy $C_1$-$C_6$ alkyl, $C_1$-$C_6$ alkoxycarbonyl, $C_1$-$C_6$ alkanoyl, $NR_7R_8$, or —C(O) $NR_7R_8$, wherein $R_7$ and $R_8$ are independently H or $C_1$-$C_6$ alkyl, wherein the $C_1$-$C_6$ alkyl is optionally substituted with 1, 2, or 3 groups that are independently $C_1$-$C_6$ alkoxycarbonyl, halogen, $C_1$-$C_6$ alkoxy, $C_1$-$C_6$ alkanoyl, $NH_2$, NH($C_1$-$C_6$ alkyl), N($C_1$-$C_6$ alkyl) ($C_1$-$C_6$ alkyl) or $CO_2H$;

wherein the heterocycloalkyl and the cycloalkyl portions of $R_4$ and $R_5$ are further optionally substituted with =O, =N—OH, or =N—$OCH_3$.

Preferred compounds of Embodiment 79 include those of Embodiment 80, i.e., compounds of Embodiment 79 where $R_1$ is phenyl which is unsubstituted or substituted with 1, 2, 3, 4, or 5 groups that are independently $C_1$-$C_6$ alkyl, halogen, $C_1$-$C_6$ alkoxy, OH, CN, $CO_2H$, $C_1$-$C_4$ haloalkyl, $C_1$-$C_4$ haloalkoxy, —OC(O)—$C_1$-$C_6$ alkyl, $C_1$-$C_6$ alkoxycarbonyl, $C_1$-$C_6$ alkanoyl, —C(O)$R_{10}$, $NR_6R_7$, —($C_1$-$C_4$ alkyl)-$NR_6R_7$, —C(O)$NR_6R_7$, pyridyl, piperidinyl, or phenyl, which is optionally substituted with 1, 2, 3, 4, or 5 groups that are independently selected from $C_1$-$C_4$ alkyl, $C_1$-$C_4$ alkoxy, halogen, $CF_3$, and $OCF_3$, wherein each $R_6$ and $R_7$ is independently H, $C_1$-$C_6$ alkyl, $C_1$-$C_4$ alkoxyalkyl, $C_1$-$C_6$ alkoxycarbonyl, wherein the alkyl portion of each is unsubstituted or substituted with 1, 2, or 3, groups that are independently halogen, OH, $CF_3$, $OCF_3$, $NH_2$, NH($C_1$-$C_6$ alkyl) or N($C_1$-$C_6$ alkyl) ($C_1$-$C_6$ alkyl).

Preferred compounds of Embodiment 71 include those of Embodiment 80A, i.e., compounds of Embodiment 71 where
Z is a bond.

Preferred compounds of Embodiment 71 include those of Embodiment 80B, i.e., compounds of Embodiment 71 where Z is —$CH_2$—.

Preferred compounds of Embodiment 71 include those of Embodiment 80C, i.e., compounds of Embodiment 71 where wherein Z is —NH—.

Preferred compounds of Embodiment 71 include those of Embodiment 80D, i.e., compounds of Embodiment 71 where Z is —S— or —$SO_2$—.

Preferred compounds of Embodiment 71 include those of Embodiment 80e, i.e., compounds of Embodiment 71 where Z is —N($C_1$-$C_4$ alkyl)-. In another aspect, Z is —N($C_1$-$C_2$ alkyl)-. In still another aspect, Z is —N($C_2$-$C_3$ alkyl)-.

Preferred compounds of Embodiment 71 include those of Embodiment 80F, i.e., compounds of Embodiment 71 where Z is —$SO_2NH$—, or —$SO_2N$($C_1$-$C_4$ alkyl)-.

In still another aspect, the invention provides compounds according to embodiment 71, wherein $R_{21}$ is H.

In yet still another aspect, the invention provides compounds according to embodiment 71, wherein $R_{21}$ is CN.

In still yet another aspect, the invention provides compounds according to embodiment 71, wherein $R_{21}$ is amino, monoalkylamino, or dialkylamino.

In yet another aspect, the invention provides compounds of embodiment 71, wherein $R_{21}$ is OH.

In still another aspect, the invention provides compounds of embodiment 71, wherein $R_{21}$ is phenyl.

In still another aspect, the invention provides compounds of embodiment 71, wherein $R_{21}$ is pyridyl.

In still another aspect, the invention provides compounds of embodiment 71, wherein $R_{21}$ is halogen.

In yet another aspect, the invention provides compounds of embodiment 71, wherein $R_{21}$ is phenyl, which is substituted with 1-5 groups that are independently $C_1$-$C_6$ alkyl, $C_1$-$C_6$ alkoxy, halogen, OH, hydroxyl $C_1$-$C_4$ alkyl, haloalkyl (in one aspect, $CF_3$), or haloalkoxy (in one aspect, $OCF_3$)).

In yet still another aspect, the invention provides compounds of embodiment 71, wherein $R_{21}$ is pyridyl or pyrimidyl, each of which is optionally substituted with 1-5 groups that are independently $C_1$-$C_6$ alkyl, $C_1$-$C_6$ alkoxy, halogen, OH, hydroxyl $C_1$-$C_4$ alkyl, haloalkyl (in one aspect, $CF_3$), or haloalkoxy (in one aspect, $OCF_3$)).

In yet still another aspect, the invention provides compounds of embodiment 71, wherein $R_{21}$ is indolyl or (iso) quinolinyl, each of which is optionally substituted with 1-5 groups that are independently $C_1$-$C_6$ alkyl, $C_1$-$C_6$ alkoxy, halogen, OH, hydroxyl $C_1$-$C_4$ alkyl, haloalkyl (in one aspect, $CF_3$), or haloalkoxy (in one aspect, $OCF_3$)).

In still another aspect, the invention provides compounds of embodiment 71, wherein $R_{21}$ is $C_1$-$C_6$ alkyl, $C_2$-$C_6$ alkynyl, or $C_2$-$C_6$ alkenyl.

In still yet another aspect, the invention provides compounds of embodiment 71, wherein $R_{21}$ is —C(O)$NH_2$, —C(O)NH($C_1$-$C_6$ alkyl), or —C(O)N($C_1$-$C_6$ alkyl) ($C_1$-$C_6$ alkyl).

Preferred compounds of Embodiment 71 include those of Embodiment 81, i.e., compounds of Embodiment 71 where $R_2$ and $R_3$ are both H; and $R_4$ and $R_5$ are independently H, $C_1$-$C_6$ alkyl, $C_1$-$C_4$ alkoxy $C_1$-$C_6$ alkyl, piperidinyl, pyrrolidinyl, morpholinyl, morpholinyl $C_1$-$C_6$ alkyl, piperidinyl $C_1$-$C_6$ alkyl, pyrrolidinyl $C_1$-$C_6$ alkyl, phenyl, furanyl, pyridyl, pyrazinyl $C_1$-$C_6$ alkyl, pyridyl $C_1$-$C_6$ alkyl, imidazolyl $C_1$-$C_6$ alkyl, furanyl $C_1$-$C_6$ alkyl, thienyl $C_1$-$C_6$ alkyl, phenyl $C_1$-$C_6$ alkyl, wherein the cyclic portion of each of the above is unsubstituted or substituted with one or more groups that are independently $C_1$-$C_6$ alkyl, $C_1$-$C_6$ alkoxy, halogen, —$SO_2$—($C_1$-$C_6$) alkyl, $C_1$-$C_4$ haloalkyl, $C_1$-$C_4$ haloalkoxy, $NO_2$, CN, OH, phenyl $C_1$-$C_6$ alkyl wherein the phenyl is optionally substituted with 1, 2, 3, 4, or 5 groups that are independently selected from $C_1$-$C_4$ alkyl, $C_1$-$C_4$ alkoxy, CN, halogen, OH, and alkanoyl, $C_1$-$C_6$ alkoxy $C_1$-$C_6$ alkyl, $C_1$-$C_6$ alkoxycarbonyl, $C_1$-$C_6$ alkanoyl, $NR_7R_8$, or —C(O)$NR_7R_8$, wherein $R_7$ and $R_8$ are independently H or $C_1$-$C_6$ alkyl, wherein the $C_1$-$C_6$ alkyl is optionally substituted with 1, 2, or 3 groups that are independently $C_1$-$C_6$ alkoxycarbonyl, halogen, $C_1$-$C_6$ alkoxy, $C_1$-$C_6$ alkanoyl, $NH_2$, NH($C_1$-$C_6$ alkyl), N($C_1$-$C_6$ alkyl) ($C_1$-$C_6$ alkyl) or $CO_2H$;

wherein the heterocycloalkyl and the cycloalkyl portions of $R_4$ and $R_5$ are further optionally substituted with =O, =N—OH, or =N—$OCH_3$.

Preferred compounds of Embodiment 81 include those of Embodiment 82, i.e., compounds of Embodiment 81 where $R_1$ is thienyl, furanyl, indolyl, pyridyl, pyridazinyl, pyrimidyl, pyrazinyl, triazolyl, imidazolyl, benzofuranyl, piperidinyl, pyrrolidinyl, piperazinyl, or morpholinyl, each of which is unsubstituted or substituted with 1, 2, 3, or 4 groups that are independently $C_1$-$C_6$ alkyl, halogen, $C_1$-$C_6$ alkoxy, OH, CN, $CO_2H$, $CF_3$, $OCF_3$, —OC(O)—$C_1$-$C_6$ alkyl, $C_1$-$C_6$ alkoxycarbonyl, $C_1$-$C_6$ alkanoyl, $NR_6R_7$, —($C_1$-$C_4$ alkyl) -$NR_6R_7$, —C(O)$NR_6R_7$, pyridyl, piperidinyl, or phenyl, which is optionally substituted with 1, 2, 3, 4, or 5 groups that are independently selected from $C_1$-$C_4$ alkyl, $C_1$-$C_4$ alkoxy, halogen, $CF_3$, and $OCF_3$, wherein each $R_6$ and $R_7$ is independently H, $C_1$-$C_6$ alkyl, $C_1$-$C_4$ alkoxyalkyl, $C_1$-$C_6$ alkoxycarbonyl, wherein the alkyl portion of each is unsubstituted or substituted with 1, 2, or 3, groups that are independently halogen, OH, $C_1$-$C_4$ haloalkyl, $C_1$-$C_4$ haloalkoxy, $NH_2$, $NH(C_1$-$C_6$ alkyl) or $N(C_1$-$C_6$ alkyl) ($C_1$-$C_6$ alkyl).

Preferred compounds of Embodiment 82 include those of Embodiment 83, i.e., compounds of Embodiment 82 where $R_1$ is thienyl optionally substituted with 1, 2, 3, or 4 groups that are independently $C_1$-$C_6$ alkyl, halogen, $C_1$-$C_6$ alkoxy, OH, CN, $CO_2H$, $CF_3$, $OCF_3$, —OC(O)—$C_1$-$C_6$ alkyl, $C_1$-$C_6$ alkoxycarbonyl, $C_1$-$C_6$ alkanoyl, $NR_6R_7$, —($C_1$-$C_4$ alkyl)-$NR_6R_7$, —C(O)$NR_6R_7$, pyridyl, piperidinyl, or phenyl, which is optionally substituted with 1, 2, 3, 4, or 5 groups that are independently selected from $C_1$-$C_4$ alkyl, $C_1$-$C_4$ alkoxy, halogen, $CF_3$, and $OCF_3$, wherein each $R_6$ and $R_7$ is independently H, $C_1$-$C_6$ alkyl, $C_1$-$C_4$ alkoxyalkyl, $C_1$-$C_6$ alkoxycarbonyl, wherein the alkyl portion of each is unsubstituted or substituted with 1, 2, or 3, groups that are independently halogen, OH, $C_1$-$C_4$ haloalkyl, $C_1$-$C_4$ haloalkoxy, $NH_2$, $NH(C_1$-$C_6$ alkyl) or $N(C_1$-$C_6$ alkyl) ($C_1$-$C_6$ alkyl)

Preferred compounds of Embodiment 82 include those of Embodiment 84, i.e., compounds of Embodiment 82 where $R_1$ is benzofuranyl optionally substituted with 1, 2, 3, or 4 groups that are independently $C_1$-$C_6$ alkyl, halogen, $C_1$-$C_6$ alkoxy, OH, CN, $CO_2H$, $CF_3$, $OCF_3$, —OC(O)—$C_1$-$C_6$ alkyl, $C_1$-$C_6$ alkoxycarbonyl, $C_1$-$C_6$ alkanoyl, $NR_6R_7$, —($C_1$-$C_4$ alkyl)-$NR_6R_7$, —C(O)$NR_6R_7$, pyridyl, piperidinyl, or phenyl, which is optionally substituted with 1, 2, 3, 4, or 5 groups that are independently selected from $C_1$-$C_4$ alkyl, $C_1$-$C_4$ alkoxy, halogen, $CF_3$, and $OCF_3$, wherein each $R_6$ and $R_7$ is independently H, $C_1$-$C_6$ alkyl, $C_1$-$C_4$ alkoxyalkyl, $C_1$-$C_6$ alkoxycarbonyl, wherein the alkyl portion of each is unsubstituted or substituted with 1, 2, or 3, groups that are independently halogen, OH, $C_1$-$C_4$ haloalkyl, $C_1$-$C_4$ haloalkoxy, $NH_2$, $NH(C_1$-$C_6$ alkyl) or $N(C_1$-$C_6$ alkyl) ($C_1$-$C_6$ alkyl)

Preferred compounds of Embodiment 51 include those of Embodiment 85, i.e., compounds of Embodiment 51 where $R_4$ and $R_5$ are independently H, methyl, or —$CH_2$-(furan-2-yl), or $C_3$-$C_6$ cycloalkyl, wherein the cycloalkyl group is optionally substituted with =O, =N—OH, or =N—$OCH_3$.

The invention also provides pharmaceutical compositions comprising a compound of Formula A and at least one pharmaceutically acceptable solvent, carrier, excipient, adjuvant or a combination thereof.

The invention further provides packaged pharmaceutical compositions comprising a pharmaceutical composition of the invention in a container together with instructions on how to use the compound or composition.

The invention further provides methods of treating a disease or condition related to cell differentiation comprising administering a therapeutically effective amount of a compound of Formula A to a patient in need of such treatment. In another embodiment, the patient is a mammal. In a more preferred embodiment, the mammal is a human.

In preferred methods of the invention, the disease or condition is cancer, inflammation, arthritis, or angiogenesis.

Other preferred compounds of the invention include those of Embodiment 91, i.e., compounds of embodiments 51-85 wherein X is —C(O)$R_{20}$, and $R_{20}$ is OH.

Other preferred compounds of the invention include those of Embodiment 92, i.e., compounds of embodiments 51-85, wherein X is —C(O)$R_{20}$, and $R_{20}$ is $C_1$-$C_6$ alkoxy (in another aspect, $C_1$-$C_4$ alkoxy.)

Other preferred compounds of the invention include those of Embodiment 93, i.e., compounds of embodiments 51-85, wherein X is —$NR_xR_y$; wherein $R_x$ and $R_y$ are independently H, $C_1$-$C_6$ alkyl, $C_1$-$C_6$ alkoxycarbonyl, phenyl $C_1$-$C_4$ alkoxycarbonyl, phenyl, naphthyl, phenyl $C_1$-$C_4$ alkyl, —C(O)—phenyl, or —C(O)—naphthyl, wherein the phenyl and naphthyl groups are optionally substituted with 1, 2, 3, 4, or 5 groups that are independently $C_1$-$C_6$ alkyl, $C_1$-$C_6$ alkoxy, halogen, $CO_2H$, $NR_6R_7$, —C(O)$NR_6R_7$, —($C_1$-$C_4$ alkyl)-$NR_6R_7$, —($C_1$-$C_4$ alkyl)-C(O)$NR_6R_7$, $CF_3$, or $OCF_3$; wherein, within the definition of $R_x$ and $R_y$.

$R_6$ and $R_7$ are independently H, $C_1$-$C_6$ alkyl, $C_1$-$C_4$ alkoxyalkyl, $C_1$-$C_6$ alkoxycarbonyl, wherein the alkyl portion of each is unsubstituted or substituted with 1, 2, or 3, groups that are independently halogen, OH, $CF_3$, OC$F_3$, $NH_2$, $NH(C_1$-$C_6$ alkyl) or $N(C_1$-$C_6$ alkyl) ($C_1$-$C_6$ alkyl); or $R_6$ and $R_7$ and the nitrogen to which they are attached form a ring having from 5 to 6 members, wherein the ring optionally contains 1-2 additional heteroatoms selected from N, O, and S, where the ring is optionally substituted with 1, 2, or 3 groups that are independently $C_1$-$C_4$ alkyl, $C_1$-$C_4$ alkoxy, OH, halogen, amino, $NH(C_1$-$C_6$ alkyl), or $N(C_1$-$C_6$ alkyl) ($C_1$-$C_6$ alkyl).

Preferred compounds of Embodiment 93 include those of Embodiment 94, i.e., compounds of Embodiment 93 where $R_x$ and $R_y$ are independently H, $C_1$-$C_6$ alkyl, $C_1$-$C_6$ alkoxycarbonyl, phenyl $C_1$-$C_4$ alkoxycarbonyl, phenyl, phenyl $C_1$-$C_4$ alkyl, or —C(O)-phenyl, wherein the phenyl group is optionally substituted with 1, 2, 3, 4, or 5 groups that are independently $C_1$-$C_4$ alkyl, $C_1$-$C_4$ alkoxy, halogen, $CO_2H$, $NR_6R_7$, —C(O)$NR_6R_7$, —($C_1$-$C_4$ alkyl)-$NR_6R_7$, —($C_1$-$C_4$ alkyl)-C(O)$NR_6R_7$, $CF_3$, or $OCF_3$.

Preferred compounds of Embodiment 94 include those of Embodiment 95, i.e., compounds of Embodiment 94 where $R_x$ and $R_y$ are independently H, $C_1$-$C_6$ alkyl, benzyl, or —C(O)-phenyl, wherein the phenyl groups are optionally substituted with 1, 2, 3, 4, or 5 groups that are independently $C_1$-$C_4$ alkyl, $C_1$-$C_4$ alkoxy, halogen, $CO_2H$, $NR_6R_7$, —C(O)$NR_6R_7$, —($C_1$-$C_4$ alkyl)-$NR_6R_7$, —($C_1$-$C_4$ alkyl)-C(O)$NR_6R_7$, $CF_3$, or $OCF_3$.

Preferred compounds of Embodiment 93 include those of Embodiment 96, i.e., compounds of Embodiment 93 where $R_x$ and $R_y$ are independently H, $C_1$-$C_6$ alkyl, pyridyl, pyrimidyl, pyrazinyl, benzofuranyl, indolyl, benzimidazolyl, thienyl, furanyl, quinolinyl, or isoquinolinyl, wherein the ring portions of the above are optionally substituted with 1, 2, 3, 4, or 5 groups that are independently $C_1$-$C_6$ alkyl, $C_1$-$C_6$ alkoxy, halogen, $CO_2H$, $NR_6R_7$, —C(O)$NR_6R_7$, —($C_1$-$C_4$ alkyl)-$NR_6R_7$, —($C_1$-$C_4$ alkyl)-C(O)$NR_6R_7$, $CF_3$, or $OCF_3$.

Preferred compounds of Embodiment 96 include those of Embodiment 96A, i.e., compounds of Embodiment 96 where $R_x$ and $R_y$ are independently H, $C_1$-$C_4$ alkyl, pyridyl, pyrimidyl, pyrazinyl, thienyl, or furanyl, wherein the ring portions of the above are optionally substituted with 1, 2, 3, 4, or 5 groups that are independently $C_1$-$C_6$ alkyl, $C_1$-$C_6$ alkoxy, halogen, $CO_2H$, $NR_6R_7$, —$C(O)NR_6R_7$, —($C_1$-$C_4$ alkyl)-$NR_6R_7$, —($C_1$-$C_4$ alkyl)-$C(O)NR_6R_7$, $CF_3$, or $OCF_3$.

Preferred compounds of Embodiment 96 include those of Embodiment 96B, i.e., compounds of Embodiment 96 where $R_x$ and $R_y$ are independently H, $C_1$-$C_6$ alkyl, benzofuranyl, indolyl, benzimidazolyl, quinolinyl, or isoquinolinyl, wherein the ring portions of the above are optionally substituted with 1, 2, 3, 4, or 5 groups that are independently $C_1$-$C_6$ alkyl, $C_1$-$C_6$ alkoxy, halogen, $CO_2H$, $NR_6R_7$, —$C(O)NR_6R_7$, —($C_1$-$C_4$ alkyl)-$NR_6R_7$, —($C_1$-$C_4$ alkyl)-$C(O)NR_6R_7$, $CF_3$, or $OCF_3$.

Preferred compounds of Embodiment 93 include those of Embodiment 97, i.e., compounds of Embodiment 93 where, wherein $R_x$ and $R_y$ are independently H, $C_1$-$C_6$ alkyl, pyridyl $C_1$-$C_6$ alkyl, pyrimidyl $C_1$-$C_6$ alkyl, pyrazinyl $C_1$-$C_6$ alkyl, benzofuranyl $C_1$-$C_6$ alkyl, indolyl $C_1$-$C_6$ alkyl, benzimidazolyl $C_1$-$C_6$ alkyl, thienyl $C_1$-$C_6$ alkyl, furanyl $C_1$-$C_6$ alkyl, quinolinyl $C_1$-$C_6$ alkyl, or isoquinolinyl $C_1$-$C_6$ alkyl, wherein the ring portions of the above are optionally substituted with 1, 2, 3, 4, or 5 groups that are independently $C_1$-$C_6$ alkyl, $C_1$-$C_6$ alkoxy, halogen, $CO_2H$, $NR_6R_7$, —$C(O)NR_6R_7$, —($C_1$-$C_4$ alkyl)-$NR_6R_7$, —($C_1$-$C_4$ alkyl)-$C(O)NR_6R_7$, $CF_3$, or $OCF_3$.

Preferred compounds of Embodiment 97 include those of Embodiment 97A, i.e., compounds of Embodiment 97 where $R_x$ and $R_y$ are independently H, $C_1$-$C_6$ alkyl, pyridyl $C_1$-$C_6$ alkyl, pyrimidyl $C_1$-$C_6$ alkyl, pyrazinyl $C_1$-$C_6$ alkyl, thienyl $C_1$-$C_6$ alkyl, or furanyl $C_1$-$C_6$ alkyl, wherein the ring portions of the above are optionally substituted with 1, 2, 3, 4, or 5 groups that are independently $C_1$-$C_6$ alkyl, $C_1$-$C_6$ alkoxy, halogen, $CO_2H$, $NR_6R_7$, —$C(O)NR_6R_7$, —($C_1$-$C_4$ alkyl)-$NR_6R_7$, —($C_1$-$C_4$ alkyl)-$C(O)NR_6R_7$, $CF_3$, or $OCF_3$.

Preferred compounds of Embodiment 97 include those of Embodiment 97B, i.e., compounds of Embodiment 97 where $R_x$ and $R_y$ are independently H, $C_1$-$C_6$ alkyl, benzofuranyl $C_1$-$C_6$ alkyl, indolyl $C_1$-$C_6$ alkyl, benzimidazolyl $C_1$-$C_6$ alkyl, quinolinyl $C_1$-$C_6$ alkyl, or isoquinolinyl $C_1$-$C_6$ alkyl, wherein the ring portions of the above are optionally substituted with 1, 2, 3, 4, or 5 groups that are independently $C_1$-$C_6$ alkyl, $C_1$-$C_6$ alkoxy, halogen, $CO_2H$, $NR_6R_7$, —$C(O)NR_6R_7$, —($C_1$-$C_4$ alkyl)-$NR_6R_7$, —($C_1$-$C_4$ alkyl)-$C(O)NR_6R_7$, $CF_3$, or $OCF_3$.

Preferred compounds of Embodiment 93 include those of Embodiment 98, i.e., compounds of Embodiment 93 where $R_x$ and $R_y$ are independently H, $C_1$-$C_6$ alkyl, —C(O)-pyridyl, —C(O)-pyrimidyl, —C(O)-pyrazinyl, —C(O)-benzofuranyl, —C(O)-indolyl, —C(O)-benzimidazolyl, —C(O)-thienyl, —C(O)-furanyl, —C(O)-quinolinyl, or —C(O)-isoquinolinyl, wherein the ring portions of the above are optionally substituted with 1, 2, 3, 4, or 5 groups that are independently $C_1$-$C_6$ alkyl, $C_1$-$C_6$ alkoxy, halogen, $CO_2H$, $NR_6R_7$, —$C(O)NR_6R_7$, —($C_1$-$C_4$ alkyl)-$NR_6R_7$, —($C_1$-$C_4$ alkyl)-$C(O)NR_6R_7$, $CF_3$, or $OCF_3$.

Preferred compounds of Embodiment 98 include those of Embodiment 98A, i.e., compounds of Embodiment 98 where $R_x$ and $R_y$ are independently H, $C_1$-$C_6$ alkyl, —C(O)-pyridyl, —C(O)-pyrimidyl, —C(O)-pyrazinyl, —C(O)-thienyl, or —C(O)-furanyl, wherein the ring portions of the above are optionally substituted with 1, 2, 3, 4, or 5 groups that are independently $C_1$-$C_6$ alkyl, $C_1$-$C_6$ alkoxy, halogen, $CO_2H$, $NR_6R_7$, —$C(O)NR_6R_7$, —($C_1$-$C_4$ alkyl)-$NR_6R_7$, —($C_1$-$C_4$ alkyl)-$C(O)NR_6R_7$, $CF_3$, or $OCF_3$.

Preferred compounds of Embodiment 98 include those of Embodiment 98B, i.e., compounds of Embodiment 98 where $R_x$ and $R_y$ are independently H, $C_1$-$C_6$ alkyl, —C(O)-benzofuranyl, —C(O)-indolyl, —C(O)-benzimidazolyl, —C(O)-quinolinyl, or —C(O)-isoquinolinyl, wherein the ring portions of the above are optionally substituted with 1, 2, 3, 4, or 5 groups that are independently $C_1$-$C_6$ alkyl, $C_1$-$C_6$ alkoxy, halogen, $CO_2H$, $NR_6R_7$, —$C(O)NR_6R_7$, —($C_1$-$C_4$ alkyl)-$NR_6R_7$, —($C_1$-$C_4$ alkyl)-$C(O)NR_6R_7$, $CF_3$, or $OCF_3$.

Embodiment 99 includes compounds of embodiments 93, 94, 95, 96, 96A, 96B, 97, 97A, 97B, 98, 98A, and 98B, wherein, within the definition of $R_x$ and $R_y$, $R_6$ and $R_7$ and the nitrogen to which they are attached form a ring having from 5 to 6 members, wherein the ring optionally contains 1-2 additional heteroatoms selected from N, O, and S, where the ring is optionally substituted with 1, 2, or 3 groups that are independently $C_1$-$C_4$ alkyl, $C_1$-$C_4$ alkoxy, OH, halogen, amino, $NH(C_1$-$C_6$ alkyl), or $N(C_1$-$C_6$ alkyl) ($C_1$-$C_6$ alkyl).

Preferred compounds of Embodiment 99 include those of Embodiment 100, i.e., compounds of Embodiment 99 where, within the definition of $R_x$ and $R_y$, $R_6$ and $R_7$ and the nitrogen to which they are attached form a ring that is pyridyl, pyridazinyl, pyrimidyl, pyrazinyl, oxazolyl, isoxazolyl, thiazolyl, isothiazolyl, imidazolyl, imidazolidinyl, pyrrolidinyl, pyrrolyl, piperidinyl, piperazinyl, or oxazolidinyl, each of which is optionally substituted with 1, 2, or 3 groups that are independently $C_1$-$C_4$ alkyl, $C_1$-$C_4$ alkoxy, OH, halogen, amino, $NH(C_1$-$C_6$ alkyl), or $N(C_1$-$C_6$ alkyl) ($C_1$-$C_6$ alkyl)

Embodiment 101 includes compounds of embodiments 93, 94, 95, 96, 96A, 96B, 97, 97A, 97B, 98, 98A, and 98B, wherein, within the definition of $R_x$ and $R_y$, $R_6$ and $R_7$ are independently H, $C_1$-$C_6$ alkyl, $C_1$-$C_4$ alkoxyalkyl, $C_1$-$C_6$ alkoxycarbonyl, wherein the alkyl portion of each is unsubstituted or substituted with 1, or 2 groups that are independently halogen, OH, $CF_3$, $OCF_3$, $NH_2$, $NH(C_1$-$C_6$ alkyl) or $N(C_1$-$C_6$ alkyl) ($C_1$-$C_6$ alkyl).

Embodiment 102 includes compounds of embodiments 93, 94, 95, 96, 96A, 96B, 97, 97A, 97B, 98, 98A, 98B, 99, 100, and 101 wherein, within the definition of $R_x$ and $R_y$, $R_x$ is H or $C_1$-$C_4$ alkyl.

In another aspect, the invention provides compounds according to any of the preceding embodiments wherein at least one of $A_1$ and $A_2$ is N. In another embodiment, both $A_1$ and $A_2$ are N.

In yet another aspect, the invention provides compounds according to any one of the preceding embodiments wherein at least one of ----- is a double bond. In a more preferred aspect, both ----- are double bonds.

In still another aspect, the invention provides compounds according to any one of the preceding embodiments wherein both ----- are single bonds and $A_2$ is NH or $N(C_1$-$C_4$ alkyl).

In yet still another aspect, at least one of $R_2$, $R_2'$ and $R_3$ is hydrogen. In another aspect, two of $R_2$, $R_2'$ and $R_3$ are hydrogen. In still another aspect, $R_2$ is methyl or halogen (in still another aspect, the halogen is chloro or bromo.)

In another aspect, $R_2$, $R_2'$, $R_{21}$, and $R_3$ are hydrogen.

In still another aspect, the invention provides compounds of formula A, wherein $R_{21}$ is H.

In yet still another aspect, the invention provides compounds of formula A, wherein $R_{21}$ is CN.

In still yet another aspect, the invention provides compounds of formula A, wherein $R_{21}$ is amino, monoalkylamino, or dialkylamino.

In yet another aspect, the invention provides compounds of formula A, wherein $R_{21}$ is OH.

In still another aspect, the invention provides compounds of formula A, wherein $R_{21}$ is phenyl.

In still another aspect, the invention provides compounds of formula A, wherein $R_{21}$ is pyridyl.

In still another aspect, the invention provides compounds of formula A, wherein $R_{21}$ is halogen.

In yet another aspect, the invention provides compounds of formula A, wherein $R_{21}$ is phenyl, which is substituted with 1-5 groups that are independently $C_1$-$C_6$ alkyl, $C_1$-$C_6$ alkoxy, halogen, OH, hydroxyl $C_1$-$C_4$ alkyl, haloalkyl (in one aspect, $CF_3$), or haloalkoxy (in one aspect, $OCF_3$)).

In yet still another aspect, the invention provides compounds of formula A, wherein $R_{21}$ is pyridyl or pyrimidyl, each of which is optionally substituted with 1-5 groups that are independently $C_1$-$C_6$ alkyl, $C_1$-$C_6$ alkoxy, halogen, OH, hydroxyl $C_1$-$C_4$ alkyl, haloalkyl (in one aspect, $CF_3$), or haloalkoxy (in one aspect, $OCF_3$)).

In yet still another aspect, the invention provides compounds of formula A, wherein $R_{21}$ is indolyl or (iso)quinolinyl, each of which is optionally substituted with 1-5 groups that are independently $C_1$-$C_6$ alkyl, $C_1$-$C_6$ alkoxy, halogen, OH, hydroxyl $C_1$-$C_4$ alkyl, haloalkyl (in one aspect, $CF_3$), or haloalkoxy (in one aspect, $OCF_3$)).

In still another aspect, the invention provides compounds of formula A, wherein $R_{21}$ is $C_1$-$C_6$ alkyl, $C_2$-$C_6$ alkynyl, or $C_2$-$C_6$ alkenyl.

In still yet another aspect, the invention provides compounds of formula A, wherein $R_{21}$ is —C(O)$NH_2$, —C(O)NH($C_1$-$C_6$ alkyl), or —C(O)N($C_1$-$C_6$ alkyl) ($C_1$-$C_6$ alkyl).

In another aspect, the invention encompasses a method of treating cancer comprising administering to a patient in need thereof, a pharmaceutically acceptable amount of a compound or salt of formula A or a pharmaceutical composition comprising a compound or salt of formula A.

The term "alkoxy" represents an alkyl group of indicated number of carbon atoms attached to the parent molecular moiety through an oxygen bridge. Examples of alkoxy groups include, for example, methoxy, ethoxy, propoxy and isopropoxy.

As used herein, the term "alkyl" includes those alkyl groups of a designed number of carbon atoms. Alkyl groups may be straight, or branched. Examples of "alkyl" include methyl, ethyl, propyl, isopropyl, butyl, iso-, sec- and tert-butyl, pentyl, hexyl, heptyl, 3-ethylbutyl, and the like.

The term "aryl" refers to an aromatic hydrocarbon ring system containing at least one aromatic ring. The aromatic ring may optionally be fused or otherwise attached to other aromatic hydrocarbon rings or non-aromatic hydrocarbon rings. Examples of aryl groups include, for example, phenyl, naphthyl, 1,2,3,4-tetrahydronaphthalene and biphenyl. Preferred examples of aryl groups include phenyl, naphthyl, and anthracenyl. More preferred aryl groups are phenyl and naphthyl. Most preferred is phenyl.

The term "cycloalkyl" refers to a $C_3$-$C_8$ cyclic hydrocarbon. Examples of cycloalkyl include cyclopropyl, cyclobutyl, cyclopentyl, cyclohexyl, cycloheptyl and cyclooctyl. More preferred are $C_3$-$C_6$ cycloalkyl groups.

The terms "halogen" or "halo" indicate fluorine, chlorine, bromine, and iodine.

The term "heterocycloalkyl" refers to a ring or ring system containing at least one heteroatom selected from nitrogen, oxygen, and sulfur, wherein said heteroatom is in a non-aromatic ring. The heterocycloalkyl ring is optionally fused to or otherwise attached to other heterocycloalkyl rings and/or non-aromatic hydrocarbon rings and/or phenyl rings. Preferred heterocycloalkyl groups have from 3 to 7 members. More preferred heterocycloalkyl groups have 5 or 6 members. Examples of heterocycloalkyl groups include, for example, 1,2,3,4-tetrahydroisoquinolinyl, piperazinyl, morpholinyl, piperidinyl, tetrahydrofuranyl, pyrrolidinyl, pyridinonyl, and pyrazolidinyl. Preferred heterocycloalkyl groups include piperidinyl, piperazinyl, morpholinyl, pyrrolidinyl, pyridinonyl, dihydropyrrolidinyl, and pyrrolidinonyl.

The term "heteroaryl" refers to an aromatic ring system containing at least one heteroatom selected from nitrogen, oxygen, and sulfur. The heteroaryl ring may be fused or otherwise attached to one or more heteroaryl rings, aromatic or non-aromatic hydrocarbon rings or heterocycloalkyl rings. Examples of heteroaryl groups include, for example, pyridine, furan, thienyl, 5,6,7,8-tetrahydroisoquinoline and pyrimidines.

Preferred examples of heteroaryl groups include thienyl, benzothienyl, pyridyl, quinolyl, pyrazolyl, pyrimidyl, imidazolyl, benzimidazolyl, furanyl, benzofuranyl, dibenzofuranyl, thiazolyl, benzothiazolyl, isoxazolyl, oxadiazolyl, isothiazolyl, benzisothiazolyl, triazolyl, pyrrolyl, indolyl, pyrazolyl, and benzopyrazolyl.

The compounds of this invention may contain one or more asymmetric carbon atoms, so that the compounds can exist in different stereoisomeric forms. These compounds can be, for example, racemates, chiral non-racemic or diastereomers. In these situations, the single enantiomers, i.e., optically active forms, can be obtained by asymmetric synthesis or by resolution of the racemates. Resolution of the racemates can be accomplished, for example, by conventional methods such as crystallization in the presence of a resolving agent; chromatography, using, for example a chiral HPLC column; or derivatizing the racemic mixture with a resolving reagent to generate diastereomers, separating the diastereomers via chromatography, and removing the resolving agent to generate the original compound in enantiomerically enriched form. Any of the above procedures can be repeated to increase the enantiomeric purity of a compound.

When the compounds described herein contain olefinic double bonds or other centers of geometric asymmetry, and unless otherwise specified, it is intended that the compounds include the cis, trans, Z- and E-configurations. Likewise, all tautomeric forms are also intended to be included.

The compounds of general Formula A may be administered orally, topically, parenterally, by inhalation or spray or rectally in dosage unit formulations containing conventional non-toxic pharmaceutically acceptable carriers, adjuvants and vehicles. The term parenteral as used herein includes percutaneous, subcutaneous, intravascular (e.g., intravenous), intramuscular, or intrathecal injection or infusion techniques and the like. In addition, there is provided a pharmaceutical formulation comprising a compound of general Formula A and a pharmaceutically acceptable carrier. One or more compounds of general Formula A may be present in association with one or more non-toxic pharmaceutically acceptable carriers and/or diluents and/or adjuvants, and if desired other active ingredients. The pharmaceutical compositions containing compounds of general Formula A may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preservative agents in order to provide pharmaceutically elegant and palatable preparations. Tablets contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques. In some cases such coatings may be prepared by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules, wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Formulations for oral use may also be presented as lozenges.

Aqueous suspensions contain the active materials in admixture with excipients suitable for the manufacture of aqueous suspensions. Such excipients are suspending agents, for example sodium carboxymethylcellulose, methylcellulose, hydropropyl-methylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents and flavoring agents may be added to provide palatable oral preparations. These compositions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil or a mineral oil or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol, glucose or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents that have been mentioned above. The sterile injectable preparation may also be a sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of general Formula A may also be administered in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials include cocoa butter and polyethylene glycols.

Compounds of general Formula A may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

For disorders of the eye or other external tissues, e.g., mouth and skin, the formulations are preferably applied as a topical gel, spray, ointment or cream, or as a suppository, containing the active ingredients in a total amount of, for example, 0.075 to 30% w/w, preferably 0.2 to 20% w/w and most preferably 0.4 to 15% w/w. When formulated in an ointment, the active ingredients may be employed with either paraffinic or a water-miscible ointment base.

Alternatively, the active ingredients may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound which enhances absorption or penetration of the active ingredient through the skin or other affected areas. Examples of such dermal penetration enhancers include dimethylsulfoxide and related analogs. The compounds of this invention can also be administered by a transdermal device. Preferably topical administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane. The transdermal patch may include the compound in a suitable solvent system with an adhesive system, such as an acrylic emulsion, and a polyester patch. The oily phase of the emulsions of this invention may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. Emulsifiers and emulsion stabilizers suitable for use in the formulation of the present invention include Tween 60, Span 80, cetostearyl alcohol, myristyl alcohol, glyceryl monostearate, and sodium lauryl sulfate, among others. The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredients are dissolved or suspended in suitable carrier, especially an aqueous solvent for the active ingredients. The antiinflammatory active ingredients are preferably present in such formulations in a concentration of 0.5 to 20%, advantageously 0.5 to 10% and particularly about 1.5% w/w. For therapeutic purposes, the active compounds of this combination invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Dosage levels of the order of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient. The daily dose can be administered in one to four doses per day. In the case of skin conditions, it may be preferable to apply a topical preparation of compounds of this invention to the affected area two to four times a day.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

For administration to non-human animals, the composition may also be added to the animal feed or drinking water. It may be convenient to formulate the animal feed and drinking water compositions so that the animal takes in a therapeutically appropriate quantity of the composition along with its diet. It may also be convenient to present the composition as a premix for addition to the feed or drinking water. Preferred non-human animals include domesticated animals.

The compounds of the present invention may be prepared by use of known chemical reactions and procedures. Representative methods for synthesizing compounds of the invention are presented below. It is understood that the nature of the substituents required for the desired target compound often determines the preferred method of synthesis. All variable groups of these methods are as described in the generic description if they are not specifically defined below.

Methods of Preparation

General Procedure for Amide Coupling Reactions:

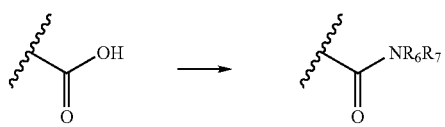

$R_6$ and $R_7$ are as defined above.

To 1 equiv. of carboxylic acid in DMF is added 1 equiv. of the appropriate amine. The reaction mixture is stirred and cooled to 0° C. in an ice bath. 1 equiv. of diethylcyanophosphonate and 2 equiv. of triethylamine are then added. After stirring for 10 minutes at 0° C., the reaction mixture is removed from the ice bath and stirred at room temperature for 18-24 hours. Once the reaction was complete, as determined by LC/MS, the reaction is concentrated to dryness. The resulting residue is dissolved in DCM (15 mL) and washed with 0.1N HCl (1×15 mL) and water (2×15 mL). The organic layer is then dried over sodium sulfate, filtered, and concentrated in vacuo to afford the crude product, which is purified via column chromatography to yield the final product.

One of skill in the art will appreciate that other methods of forming an amide bond are available. For example, the acid may be converted to an acid chloride or an acid anhydride and then treated with the amine. Or, the acid may be treated with one or more coupling reagents, such as DCC (dicyclohexyl carbodiimide), DIC (1,3 diisopropyl carbodiimide), EDCI (1-ethyl-3-(3'-dimethylaminopropyl)carbodiimide hydrochloride), BBC (1-benzotriazol-1-yloxy-bis(pyrrolidino)uronium hexafluorophosphate), BDMP (5-(1H-benzotriazol-1-yloxy)-3,4-dihydro-1-methyl 2H-pyrrolium hexachloroanitimonate), BOMI (benzotriazol-1-yloxy-N,N-dimethylmethaniminium hexachloroantimonate), HATU (O-(7-azabenzotriazol-1-yl)-1,1,3,3-tetramethyluronium hexafluorophosphate), HAPyU=O-(7-azabenzotriazol-1-yl)-1,1,3,3-bis(tetramethylene)uronium hexafluorophosphate, HBTU=O-(benzotriazol-1-yl)-1,1,3,3-tetramethyluronium hexafluorophosphate, TAPipU=O-(7-azabenzotriazol-1-yl)-1,1,3,3-bis(pentamethylene)uronium etrafluoroborate, AOP (O-(7-azabenzotriazol-1-yl)-tris(dimethylamino)phosphonium hexafluorophosphate), BDP (benzotriazol-1-yl diethyl phosphate), BOP (1-benzotriazolyoxytris(dimethylamino)phosphonium hexafluorophosphate), PyAOP (7-azobenzotriazolyoxytris(pyrrolidino)phosphonium hexafluorophosphate), PyBOP (1-benzotriazolyoxytris(pyrrolidino)phosphonium hexafluorophosphate), TDBTU (2-(3,4-dihydro-4-oxo-1,2,3-benzotriazin-3-yl)-1,1,3,3-tetramethyluronium tetrafluoroborate), TNTU (2-(5-norbornene-2,3-dicarboximido)-1,1,3,3-tetramethyluronium tetrafluoroborate), TPTU (2-(2-oxo-1(2H)-pyridyl-1,1,3,3-tetramethyluronium tetrafluoroborate), TSTU (2-succinimido-1,1,3,3-tetramethyluronium tetrafluoroborate), BEMT (2-bromo-3-ethyl-4-methyl thiazolium tetrafluoroborate), BOP-Cl (bis(2-oxo-3-oxazolidinyl)phosphinic chloride), BroP (bromotris(dimethylamino)phosphonium hexafluorophosphate), BTFFH (bis(tetramethylenefluoroformamidinium) hexafluorophosphate), ClP (2-chloro-1,3-dimethylimidazolidinium hexafluorophosphate), DEPBT (3-(diethoxyphosphoryloxy)-1,2,3-benzotriazin-4(3H)-one), Dpp-Cl (diphenylphosphinic chloride), EEDQ (2-ethoxy-1-ethoxycarbonyl-1,2-dihydroquinoline), FDPP (pentafluorophenyl diphenylphosphinate), HOTT (S-(1-oxido-2-pyridinyl)-1,1,3,3-tetramethylthiouronium hexafluorophosphate), PyBroP (bromotris(pyrrolydino)phophonium hexafluorophosphate), PyCloP (chlorotris(pyrrolydino)phophonium hexafluorophosphate), TFFH (tetramethylfluoroformamidinium hexafluorophosphate), TOTT (S-(1-oxido-2-pyridinyl)-1,1,3,3-tetramethylthiouronium tetrafluoroborate).

General Procedure for Sonogashira Couplings:

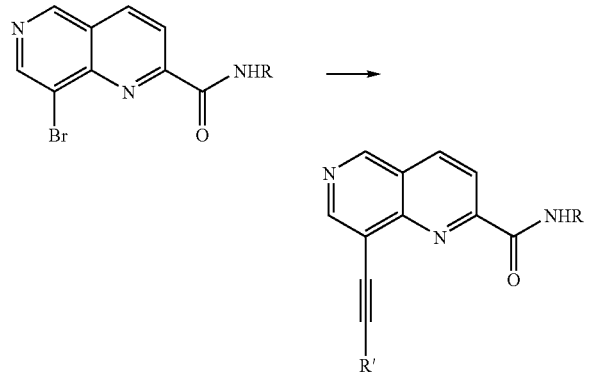

R carries the same definition as $R_4$;

R' is 1, 2, 3, 4, or 5 groups that are independently $C_1$-$C_6$ alkyl, halogen, $C_1$-$C_6$ alkoxy, OH, CN, $CO_2H$, $C_1$-$C_4$ haloalkyl, $C_1$-$C_4$ haloalkoxy, —OC(O)—$C_1$-$C_6$ alkyl, $C_1$-$C_6$ alkoxycarbonyl, $C_1$-$C_6$ alkanoyl, —C(O)$R_{10}$, $NR_6R_7$, —($C_1$-$C_4$ alkyl)-$NR_6R_7$, —C(O)$NR_6R_7$, phenyl, or naphthyl, wherein the phenyl and naphthyl groups are optionally substituted with 1 or more groups that are independently selected from $C_1$-$C_4$ alkyl, $C_1$-$C_4$ alkoxy, halogen, OH, $CF_3$, and $OCF_3$, wherein each $R_6$ and $R_7$ is independently H, $C_1$-$C_6$ alkyl, $C_1$-$C_4$ alkoxyalkyl, $C_1$-$C_6$ alkoxycarbonyl, wherein the alkyl portion of each is unsubstituted or substituted with 1, 2, or 3, groups that are independently halogen, OH, $C_1$-$C_4$ haloalkyl, $C_1$-$C_4$ haloalkoxy, $NH_2$, $NH(C_1$-$C_6$ alkyl) or $N(C_1$-$C_6$ alkyl) ($C_1$-$C_6$ alkyl); or $R_6$ and $R_7$ and the nitrogen to which they are attached form a ring having from 5 to 8 members, wherein the ring optionally contains 1-3 additional heteroatoms selected from N, O, and S, where the ring is optionally substituted with 1, 2, or 3 groups that are independently $C_1$-$C_6$ alkyl, $C_1$-$C_6$ alkoxy, halogen, OH, amino, $NH(C_1$-$C_6$ alkyl), or $N(C_1$-$C_6$ alkyl) ($C_1$-$C_6$ alkyl).

A 8-Bromo-[1,6]naphthyridine-2-carboxylic acid amide, an optionally substituted acetylene (2.5 equiv), tetrakis (triphenylphosphine)palladium (0) (5 mol %), copper (I) iodide (25 mol %), and potassium carbonate (3.0 equiv) are dissolved in 5:1 DME: water. The reaction vessel is purged with $N_2$ and stirred overnight at approximately 50° C. The solvent is removed in vacuo and the residue purified by preparative TLC, or other methods known to those skilled in the art.

General Procedure for Buchwald-Type Couplings:

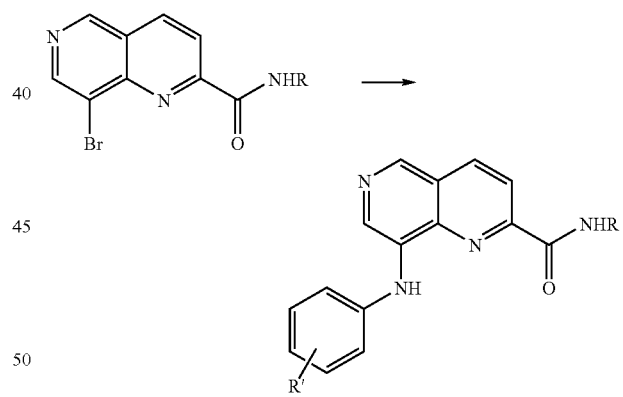

R' is 1, 2, 3, 4, or 5 groups that are independently $C_1$-$C_6$ alkyl, halogen, $C_1$-$C_6$ alkoxy, OH, CN, $CO_2H$, $C_1$-$C_4$ haloalkyl, $C_1$-$C_4$ haloalkoxy, —OC(O)—$C_1$-$C_6$ alkyl, $C_1$-$C_6$ alkoxycarbonyl, $C_1$-$C_6$ alkanoyl, —C(O)$R_{10}$, $NR_6R_7$, —($C_1$-$C_4$ alkyl)-$NR_6R_7$, —C(O)$NR_6R_7$, phenyl, or naphthyl, wherein the phenyl and naphthyl groups are optionally substituted with 1 or more groups that are independently selected from $C_1$-$C_4$ alkyl, $C_1$-$C_4$ alkoxy, halogen, OH, $CF_3$, and $OCF_3$, wherein each $R_6$ and $R_7$ is independently H, $C_1$-$C_6$ alkyl, $C_1$-$C_4$ alkoxyalkyl, $C_1$-$C_6$ alkoxycarbonyl, wherein the alkyl portion of each is unsubstituted or substituted with 1, 2, or 3, groups that are independently halogen, OH, $C_1$-$C_4$ haloalkyl, $C_1$-$C_4$ haloalkoxy, $NH_2$, $NH(C_1$-$C_6$ alkyl) or $N(C_1$-$C_6$ alkyl) ($C_1$-$C_6$ alkyl); or R$_6$ and R$_7$ and the nitrogen to which they are attached form a ring having from 5 to 8 members, wherein the ring optionally contains 1-3 additional heteroatoms selected from N, O, and S, where the ring is optionally substituted with 1, 2, or 3 groups that are independently C$_1$-C$_6$ alkyl, C$_1$-C$_6$ alkoxy, halogen, OH, amino, NH(C$_1$-C$_6$ alkyl), or N(C$_1$-C$_6$ alkyl) (C$_1$-C$_6$ alkyl).

A microwave pressure vial (Personal Chemistry) is charged with an 8-bromo-[1,6]naphthyridine-2-carboxylic acid amide (1 equiv.), an optionally substituted aniline or aminoheterocycle (4.0 equiv.), bis(dibenzylideneacetone) palladium (0) (7 mol %), 2-(dicyclohexylphosphino) biphenyl (14 mol %), and sodium tert-butoxide (2.0 equiv). The reagents are suspended in toluene to a concentration of 0.5 M (with regards to naphthyridine). The vessel is purged with N$_2$ and then the reaction mixture is heated to 110° C. via microwave radiation. After 420 seconds, the reaction vessel is allowed to cool to room temperature and then filtered through a plug of glass wool. The resulting filtrate is concentrated and purified by preparatory TLC, or other methods known to those skilled in the art.

Those having skill in the art will recognize that the starting materials and reaction conditions may be varied, the sequence of the reactions altered, and additional steps employed to produce compounds encompassed by the present invention, as demonstrated by the following examples. In some cases, protection of certain reactive functionalities may be necessary to achieve some of the above transformations. In general, the need for such protecting groups as well as the conditions necessary to attach and remove such groups will be apparent to those skilled in the art of organic synthesis.

The disclosures of all articles and references mentioned in this application, including patents, are incorporated herein by reference in their entirety.

Structures were named using Name Pro IUPAC Naming Software, version 5.09, available from Advanced Chemical Development, Inc., 90 Adelaide Street West, Toronto, Ontario, M5H 3V9, Canada or with ChemDraw v. 6.02, which is available from Cambridgesoft.com in Cambridge, Mass.

General Procedure for Suzuki Coupling Reactions:

1 equiv. 8-bromo-2-substituted-1,6-naphthyridine, 0.02 equiv. dichlorobis(triphenylphosphine)palladium (II), 1 equiv. boronic acid, 1.5 equiv. sodium carbonate and 7:3:2 DME:H$_2$O:EtOH (2-4 mL) are combined in a microwavable reaction tube. The tube is sealed and irradiated in the microwave at 140° C. for 500 seconds. The resulting reaction mixture is cooled to room temperature and diluted with water (~10-15 mL).

If final compound contains an acid, the reaction mixture is acidified to pH 6-7 with 1N HCl, and filtered. The resulting solid is washed with water (~50 mL), dried, filtered, and concentrated in vacuo to afford the crude product, which is purified by methods known in the art.

If final compound does not contain an acid, the aqueous layer is extracted with dichloromethane (4×20 mL). The dichloromethane layers are combined, dried over sodium sulfate, filtered and concentrated in vacuo to afford the crude product, which is purified by methods known in the art.

CHEMISTRY EXAMPLES

The preparation of intermediates and compounds of the invention is illustrated further by the following examples, which are not to be construed as limiting the invention in scope or spirit to the specific procedures and compounds described in them. In all cases, unless otherwise specified, the column chromatography is performed using a silica gel solid phase.

Example 1

Preparation of 8-Bromo-[1,6]naphthyridine-2-carboxylic acid methyl ester (2)

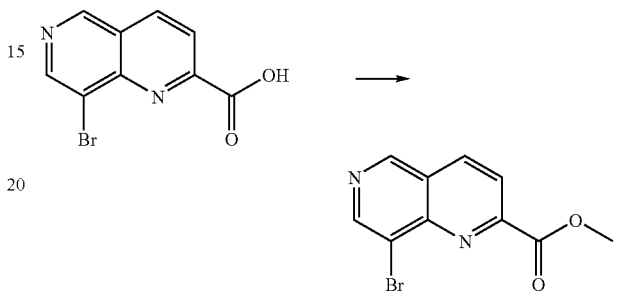

The starting acid, 8-Bromo-[1,6]naphthyridine-2-carboxylic acid (1), is prepared essentially according to the procedure described in *J. Med. Chem.* 1999, 42, 3023-3025 and the references cited therein.

8-Bromo-[1,6]naphthyridine-2-carboxylic acid methyl ester (2) is prepared by combining compound 1 (1 equiv.), cesium carbonate (1.1 equiv.) and methyl iodide (1.1 equiv.) in DMF (10 mL) and stirring for 16 hrs. at room temperature. The reaction is concentrated in vacuo to give a brown solid, which is dissolved in EtOAc (50 mL) and washed with water (2×50 mL). The EtOAc layer is dried over sodium sulfate, filtered, and concentrated in vacuo to afford a purple solid. The crude product is purified via silica gel chromatography (EtOAc) to yield (2) as a yellow solid, 65%, LC/MS (M+H) 269.0.

Example 2

Preparation of 8-Bromo-[1,6]naphthyridine-2-carboxylic acid (furan-2-ylmethyl)-amide (3)

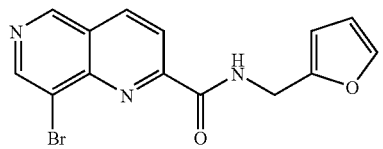

8-Bromo-[1,6]naphthyridine-2-carboxylic acid (1) is stirred in DMF (20 mL) and furfurylamine (1 equiv.) is added. The reaction mixture is cooled to 0° C. (ice bath) and diethylcyanophosphonate (1 equiv.) is added followed immediately by triethylamine (2 equiv.). The reaction mixture is removed from the ice bath and stirred at room temperature for 26 hrs. The mixture is diluted with water (50 mL) and extracted with methylene chloride (3×50 mL). The combined organic layers are dried over sodium sulfate, filtered, and concentrated in vacuo to afford a tan solid, which is purified via silica gel chromatography (1:1; hexanes:EtOAc to 1:3.) LC/MS (M+H) 332.1.

Example 3

Preparation of 5-{2-[(Furan-2-ylmethyl)-carbamoyl]-[1,6]naphthyridin-8-yl}thiophene-2-carboxylic acid (4)

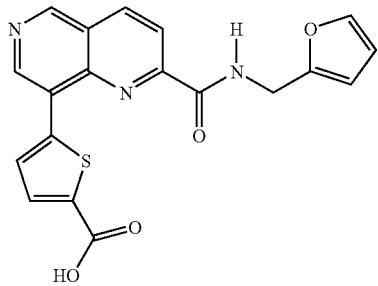

Compound 3 (above, 1 equiv.), 5-(dihydroxylboryl)-2-thiophene carboxylic acid (1 equiv.), dichloro(bistriphenylphosphine)palladium (II) (0.02 equiv.), and sodium carbonate (1.5 equiv.) are combined with 7:3:2; DME:water:methanol (4 mL) in a microwavable reaction tube. The reaction mixture is irradiated in the microwave at 140° C. for 300 seconds and then cooled to room temperature. The crude mixture is concentrated in vacuo, affording a green-brown solid. Purification via silica gel chromatography (EtOAc to 4:1; EtOAc:methanol containing 1% acetic acid) affords a bright yellow solid. LC/MS (M+H) 340.2.

Example 4

The following compounds are prepared essentially according to the procedures described above.

| Ex. No. | Name | Data | Structure |
|---|---|---|---|
| 5 | 8-[5-(2-Dimethylamino-ethylcarbamoyl)-thiophen-2-yl]-[1,6]naphthyridine-2-carboxylic acid (furan-2-ylmethyl)-amide | brownish-yellow solid: LC/MS (M + H) 450.6 | 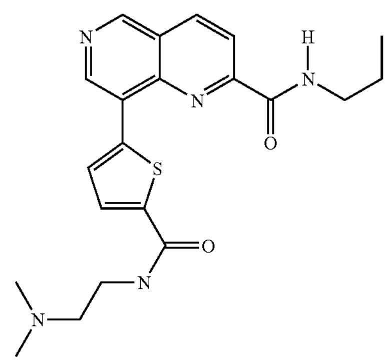 |
| 6 | 8-[5-(2-Diethylamino-ethylcarbamoyl)-thiophen-2-yl]-[1,6]naphthyridine-2-carboxylic acid (furan-2-ylmethyl)-amide | brownish-yellow solid; LC/MS (M + H) 478.3. | |
| 7 | 8-Bromo-[1,6]naphthyridine-2-carboxylic acid cyclopropylamide | yellow solid; LC/MS (M + H) 293.1 | |
| 8 | 5-(2-Cyclopropylcarbamoyl-[1,6]naphthyridin-8-yl)-thiophene-2-carboxylic acid | bright yellow solid, LC/MS (M + H) 340.2. | |
| 9 | 8-[5-(2-Dimethylamino-ethylcarbamoyl)-thiophen-2-yl]-[1,6]naphthyridine-2-carboxylic acid cyclopropylamide | yellow pseudo-solid, LC/MS (M + H) 410.4. | |
| 10 | 8-[5-(2-Diethylamino-ethylcarbamoyl)-thiophen-2-yl]-[1,6]naphthyridine-2-carboxylic acid cyclopropylamide | yellow solid, LC/MS (M + H) 438.3. | |

Example 11

Preparation of 8-Bromo-[1,6]naphthyridine-2-carboxylic acid chloride

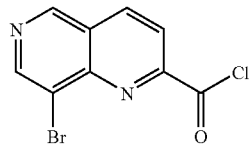

Oxalyl chloride (1.5 equiv.) is added drop wise to a slurry of 8-Bromo-[1,6]naphthyridine-2-carboxylic acid (1 equiv., in 20 mL DMF) at 0° C. (ice bath) and stirred for 30 minutes. The reaction mixture is removed from the ice bath, stirred at room temperature for 3 h and then concentrated in vacuo to give a greenish colored solid, which is used immediately without further purification.

Example 12

Preparation of 8-Bromo-[1,6]naphthyridine-2-carboxylic acid methylamide

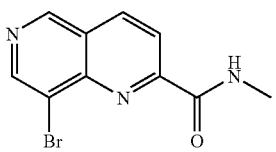

2.0 M Methylamine in ethanol is added to compound 11 and the reaction mixture is stirred for 20 h at room temperature. The reaction is concentrated in vacuo to give a greenish-brown solid that is purified via silica gel chromatography (EtOAc) to give compound 12 as a yellow solid, LC/MS (M+H) 266.9.

Example 13

Preparation of 5-(2-Methylcarbamoyl-[1,6]naphthyridin-8-yl)-thiophene-2-carboxylic acid

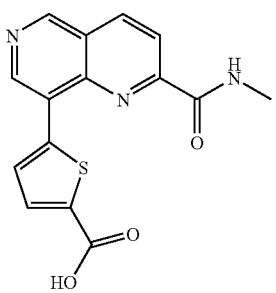

The desired compound is prepared essentially using the procedure described in Example 3. The product is a yellow solid, LC/MS (M+H) 314.16.

Example 14

Preparation of 5-(2-Methylcarbamoyl-[1,6]naphthyridin-8-yl)-thiophene-2-carboxylic acid chloride

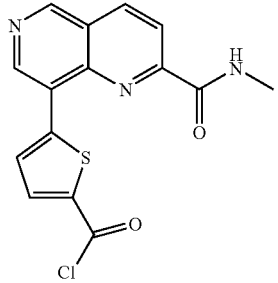

The desired compound is prepared essentially using the procedure described in Example 11. The product is a yellow paste that is used immediately without further purification.

Example 15

Preparation of 5-(2-Methylcarbamoyl-[1,6]naphthyridin-8-yl)-thiophene-2-carboxylic acid amide

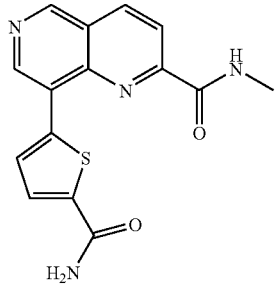

The compound is prepared by stirring compound 14 in 7N ammonia in methanol (8 mL) at room temperature for 19 h. The reaction mixture is concentrated in vacuo to afford a crude yellow solid. Purification via silica gel chromatography (CHCl$_3$/MeOH/NH4OH 80/18/2) affords the desired compound as a bright yellow solid, LC/MS (M+H) 313.4.

Preparation 1

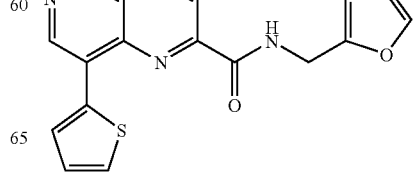

-continued

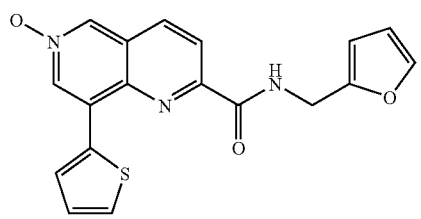

8-Thiophen-2-yl-[1,6]naphthyridine-2-carboxylic acid (furan-2-ylmethyl)-amide (1.0 equiv.) was stirred in methylene chloride (2.0 mL) under nitrogen at 0° C. (ice bath) and meta-chloroperoxybenzoic acid (1.0 equiv.) was added over 10 minutes. The reaction was warmed to room temperature and stirred for 18 hours. LC/MS indicated the N-oxide as the major product. The reaction mixture was concentrated in vacuo to afford an orange solid and used in the next reaction without further purification. LC/MS (M+H) 352.2.

Preparation 2

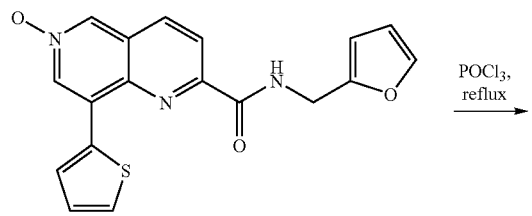

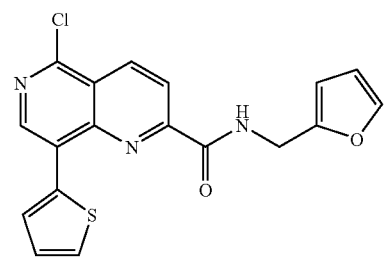

6-N-Oxo-8-thiophen-2-yl-[1,6]naphthyridine-2-carboxylic acid (furan-2-ylmethyl)-amide (1.0 equiv.) was combined with phosphorous oxychloride (8.0 mL) and refluxed for 2 hours and stirred an additional 18 hours at room temperature. The reaction mixture was poured onto ice (25 g) and stirred for 20 minutes. The resulting brown precipitate was filtered to yield the product as a brown solid. LC/MS (M+H) 370.2.

Preparation 3

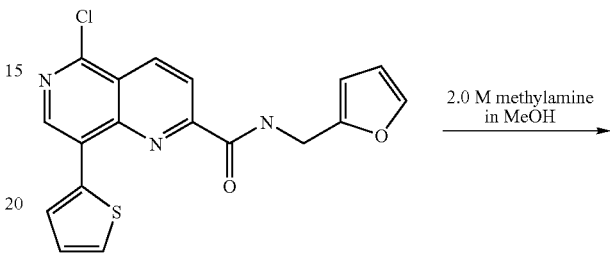

5-Chloro-8-thiophen-2-yl-[1,6]naphthyridine-2-carboxylic acid (furan-2-ylmethyl)-amide (1.0 equiv.) was combined with methylamine (10 equiv., 2.0 M in methanol) and irradiated in a microwave at 100° C. for 600 seconds. The reaction mixture was diluted with methanol (5 mL) and sonicated. The insolubles were filtered and the filtrate was evaporated to dryness to yield the expected product as an orange oil. LC/MS (M+H) 365.2.

The following compounds are prepared essentially according to the methods and procedures described above.

| Ex. No. | Name | Data | |
|---|---|---|---|
| 16 | 5-(2-Methylcarbamoyl-[1,6]naphthyridin-8-yl)-thiophene-2-carboxylic acid methylamide | bright yellow solid, LC/MS (M + H) 327.4. | 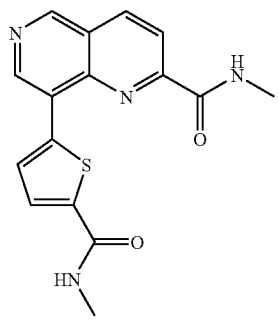 |

-continued

| Ex. No. | Name | Data | |
|---|---|---|---|
| 17 | 8-[5-(3-Morpholin-4-yl-propylcarbamoyl)-thiophen-2-yl]-[1,6]naphthyridine-2-carboxylic acid methylamide | yellow solid, LC/MS (M + H) 440.3. | |
| 18 | 8-Thiophen-3-yl[1,6]-naphthyridine-2-carboxylic acid | tan solid, LC/MS (M + H) 257.1. | |
| 19 | 8-Thiophen-3-yl[1,6]-naphthyridine-2-carboxylic acid (furan-2-ylmethyl)-amide | orange solid, LC/MS (M + H) 336.2. | |
| 20 | 8-Thiophen-3-yl[1,6]-naphthyridine-2-carboxylic acid furan-2-ylmethyl-methyl-amide | orange solid, LC/MS (M + H) 351.2. | |
| 21 | 8-Thiophen-3-yl[1,6]-naphthyridine-2-carboxylic acid cyclopropylamide | light, yellow solid, LC/MS (M + H) 296.2. | 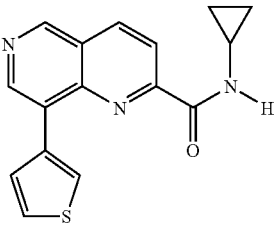 |
| 22 | 8-Thiophen-3-yl[1,6]-naphthyridine-2-carboxylic acid methylamide | tan solid, LC/MS (M + H) 270.1. | |
| 23 | 8-Thiophen-3-yl[1,6]-naphthyridine-2-carboxylic acid (2-hydroxy-cyclohexyl) amide | light, yellow solid, 58%, LC/MS (M + H) 354.2. | |
| 24 | 8-Thiophen-3-yl[1,6]-naphthyridine-2-carboxylic acid (2-oxo-cyclohexyl)amide | white solid, LC/MS (M + H) 354.2. prepared via Dess-Martin oxidation of compound 23 | |
| 25 | 8-Thiophen-3-yl-[1,6]naphthyridine-2-carboxylic acid amide | off-white solid, 27%, LC/MS (M + H) 256.3. Prepared from compound 18 | |
| 26 | 8-Thiophen-3-yl-[1,6]naphthyridine-2-carboxylic acid (tetrahydro-furan-2-ylmethyl)-amide | off-white solid, LC/MS (M + H) 340.2. | 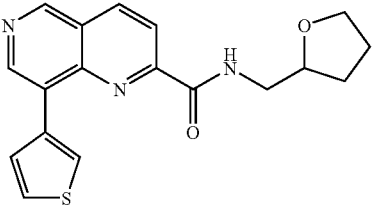 |
| 27 | 8-Phenyl[1,6]-naphthyridine-2-carboxylic acid | yellow solid, LC/MS (M + H) 251.2. | |
| 28 | 8-Phenyl[1,6]-naphthyridine-2-carboxylic acid (furan-2-ylmethyl)-amide | orange pseudo-solid, LC/MS (M + H) 330.2. | |
| 29 | 8-Phenyl[1,6]-naphthyridine-2-carboxylic acid furan-2-ylmethyl-methyl-amide | orange pseudo-solid, 73%, LC/MS (M + H) 344.3. | |
| 30 | 8-Phenyl[1,6]-naphthyridine-2-carboxylic acid cyclopropylamide | white solid, LC/MS (M + H) 290.2. | |

| Ex. No. | Name | Data | |
|---|---|---|---|
| 31 | 8-Phenyl[1,6]-naphthyridine-2-carboxylic acid amide | LC/MS (M + H) 250.2. | |
| 32 | 8-Bromo[1,6]-naphthyridine-2-carboxylic acid (2-hydroxy-cyclohexyl) amide | light, yellow solid, LC/MS (M + H) 350.2. | |
| 33 | 8-Bromo[1,6]-naphthyridine-2-carboxylic acid (2-oxo-cyclohexyl)amide | white solid, LC/MS (M + H) 348.1. prepared via Dess-Martin oxidation of compound 32 |  |
| 34 | 8-Phenyl[1,6]-naphthyridine-2-carboxylic acid (2-hydroxy-cyclohexyl) amide | white solid, LC/MS (M + H) 348.3. | |
| 35 | 8-Phenyl[1,6]-naphthyridine-2-carboxylic acid (2-oxo-cyclohexyl) amide | off-white solid, LC/MS (M + H) 346.1. | |

Example 36

Preparation of 8-(3-Hydroxy-prop-1-ynyl-[1,6]naphthyridine-2-carboxylic acid cyclopropylamide

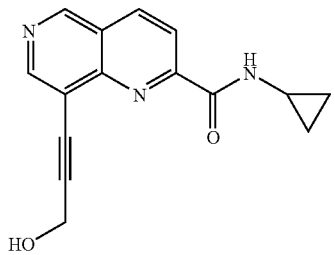

8-Bromo-[1,6]naphthyridine-2-carboxylic acid cyclopropylamide, acetylene (2.5 equiv), tetrakis(triphenylphosphine)palladium (0) (5 mol %), copper (I) iodide (25 mol %), and potassium carbonate (3.0 equiv) are dissolved in 5:1 DME:water. The reaction vessel is purged with $N_2$ and stirred overnight at 50° C. The solvent is removed in vacuo and the residue purified by preparative TLC (EtOAc) to afford the desired product as an off-white solid, LC/MS (M+H) 268.2.

| Ex. No. | Name | Data | |
|---|---|---|---|
| 37 | 8-(3-Hydroxy-prop-1-ynyl-[1,6]naphthyridine-2-carboxylic acid amide | off-white solid, LC/MS (M + H) 228.2. | 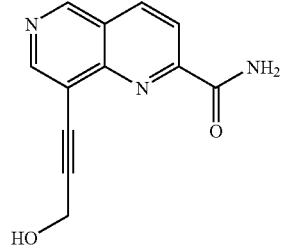 |
| 38 | 8-(3-Hydroxy-prop-1-ynyl-[1,6]naphthyridine-2-carboxylic acid (furan-2-ylmethyl) amide | off-white solid, LC/MS (M + H) 308.2. | |

| Ex. No. | Name | Data |
|---|---|---|
| 39 | (3-{2-[(Furan-2-ylmethyl)-carbamoyl]-[1,6]naphthyridin-8-yl}-prop-2-ynyl)-carbamic acid tert-butyl ester | off-white solid, LC/MS (M + H) 407.3. |
| 40 | 8-Phenylethynyl-[1,6]naphthyridine-2-carboxylic acid (furan-2-ylmethyl)-amide | off-white solid, LC/MS (M + H) 354.2. |
| 41 | 8-Ethynyl-[1,6]naphthyridine-2-carboxylic acid (furan-2-ylmethyl)-amide | off-white solid, LC/MS (M + H) 278.1. |

The following compounds were prepared essentially according to the method described for the Buchwald-type coupling.

| Ex. No. | Name | Data | Structure |
|---|---|---|---|
| 42 | 8-(4-Methoxy-phenylamino)-[1,6]naphthyridine-2-carboxylic acid (furan-2-ylmethyl)-amide | off-white solid, LC/MS (M + H) 375.2. | (structure shown) |
| 43 | 8-para-Tolylamino-[1,6]naphthyridine-2-carboxylic acid (furan-2-ylmethyl)-amide | off-white solid, LC/MS (M + H) 359.2. | |
| 44 | 8-Phenylamino-[1,6]naphthyridine-2-carboxylic acid (furan-2-ylmethyl)-amide | off-white solid, LC/MS (M + H) 345.2. | |
| 45 | 8-(3-Trifluoromethyl-phenylamino0-[1,6]naphthyridine-2-carboxylic acid (furan-2-ylmethyl)-amide | off-white solid, LC/MS (M + H) 413.2. | |
| 46 | 8-(4-Trifluoromethyl-phenylamino)-[1,6]naphthyridine-2-carboxylic acid (furan-2-ylmethyl)-amide | off-white solid, LC/MS (M + H) 413.2. | |
| 47 | 8-(Pyridin-3-ylamino)-[1,6]naphthyridine-2-carboxylic acid (furan-2-ylmethyl)-amide | off-white solid, LC/MS (M + H) 346.2. | (structure shown) |

| Ex. No. | Name | Data |
|---|---|---|
| 48 | 8-(Pyridin-4-ylamino)-[1,6]naphthyridine-2-carboxylic acid (furan-2-ylmethyl)-amide | off-white solid, LC/MS (M + H) 346.2. |
| 49 | 8-(Pyrazin-2-ylamino)-[1,6]naphthyridine-2-carboxylic acid (furan-2-ylmethyl)-amide | off-white solid, LC/MS (M + H) 347.2. |
| 50 | 8-(3,5-Dichloro-phenylamino)-[1,6]naphthyridine-2-carboxylic acid (furan-2-ylmethyl)-amide | off-white solid, LC/MS (M + H) 413.2. |
| 51 | 8-(4-Methoxy-phenylamino)-[1,6]naphthyridine-2-carboxylic acid cyclopropylamide | off-white solid, LC/MS (M + H) 335.3. |
| 52 | 8-(3,5-Dichloro-phenylamino)-[1,6]naphthyridine-2-carboxylic acid cyclopropylamide | off-white solid, LC/MS (M + H) 373.2. |

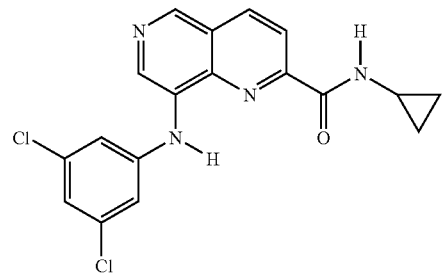

| Ex. No. | Name | Data |
|---|---|---|
| 53 | 8-(4-Methoxy-phenylamino)-[1,6]naphthyridine-2-carboxylic acid amide | off-white solid, LC/MS (M + H) 291.1. |
| 54 | 8-[(Furan-2-ylmethyl)-amino]-[1,6]naphthyridine-2-carboxylic acid (furan-2-ylmethyl)-amide | yellow solid, LC/MS (M + H) 389.3. |
| 55 | 8-[(Pyridin-4-ylmethyl)-amino]-[1,6]naphthyridine-2-carboxylic acid (furan-2-ylmethyl)-amide | yellow solid, LC/MS (M + H) 360.3. |
| 56 | 8-[(Pyridin-2-ylmethyl)-amino]-(1,6]naphthyridine-2-carboxylic acid (furan-2-ylmethyl)-amide | yellow solid, LC/MS (M + H) 360.3. |
| 57 | 8-[(Pyridin-3-ylmethyl)-amino]-[1,6]naphthyridine-2-carboxylic acid (furan-2-ylmethyl)-amide | yellow solid, LC/MS (M + H) 360.3. |

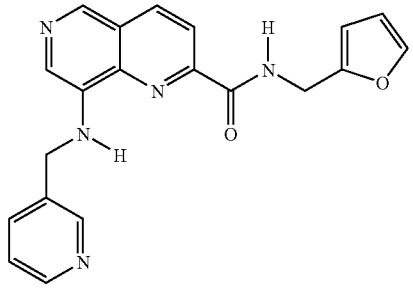

-continued

| Ex. No. | Name | Data |
|---|---|---|
| 58 | 8-(3-Methoxy-benzylamino)-[1,6]naphthyridine-2-carboxylic acid (furan-2-ylmethyl)-amide | yellow solid, LC/MS (M + H) 389.2. |
| 59 | 8-Cyclopropylamino-[1,6]naphthyridine-2-carboxylic acid (furan-2-ylmethyl)-amide | yellow solid, LC/MS (M + H) 309.2. |
| 60 | 8-Prop-2-ynylamino-[1,6]naphthyridine-2-carboxylic acid (furan-2-ylmethyl)-amide | yellow solid, LC/MS (M + H) 307.2. |
| 61 | 8-(2-Oxo-pyrrolidin-1-yl)-[1,6]naphthyridine-2-carboxylic acid (furan-2-ylmethyl)-amide | yellow solid, LC/MS (M + H) 337.3. |

Example 62

Preparation of (8-Bromo-[1,6]naphthyridin-2-yl)-carbamic acid tert-butyl ester

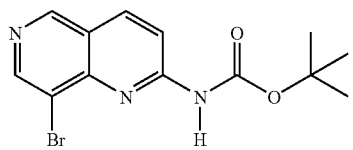

8-Bromo-[1,6]naphthyridine-2-carboxylic acid (1 equiv.) is suspended in tert-butanol (20 mL). Triethylamine (1.1 equiv.) and diphenylphosphoryl azide (1.1 equiv.) are added and the reaction is warmed to reflux. After refluxing for 2.5 hours, the reaction is allowed to cool and half the solvent is removed by rotary evaporation. The residue is dissolved in ethyl acetate (200 mL) and washed with saturated NaHCO₃ (50 mL). The organic phase is dried over magnesium sulfate, filtered and concentrated to afford the crude product. Silica gel chromatography (1:1 EtOAc:hexanes) affords the desired BOC amine as a solid, LC/MS (M+H) 324.1.

Example 63

Preparation of 8-Bromo-[1,6]naphthyridin-2-ylamine dihydrochloride

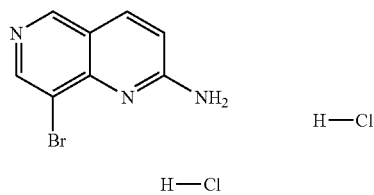

(8-Bromo-[1,6]naphthyridin-2-yl)-carbamic acid tert-butyl ester (1 equiv.) is suspended in methanol (10 mL). Acetyl chloride (ca. 1 mL) is added over 1 minute. After the reaction mixture cools to ambient temperature, the solvent is brought briefly to reflux using a heat gun. The heat gun is applied twice more, at which point TLC (1:1 EtOAc:hexanes) indicated complete reaction. Concentration, followed by trituration twice with dry methanol affords the title compound as a white solid, LC/MS (M+H) 224.1.

Example 64

Preparation of 1, 2, 3, 4-Tetrahydro-[1,6]naphthyridine-2-carboxylic acid methyl ester

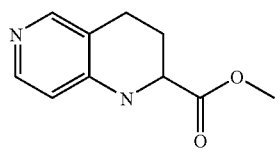

1,6]naphthyridine-2-carboxylic acid methyl ester (1 equiv.) and methanol (anhydrous, 5 mL) were combined in a reaction vessel under nitrogen atmosphere. Palladium, 5% wt. on calcium carbonate (1 equiv.) was added and hydrogen gas was bubbled through the solution via balloon for 12 h. The reaction was passed through a short plug of silica to remove the catalyst and the silica plug was washed with 20% methanol in DCM. The solvent was removed in vacuo to yield the title compound as a brown solid weighing 12 mg (59%).

The following compounds are prepared essentially according to the methods, examples, and procedures described above.

| Ex. No. | Structure | Name |
|---|---|---|
| 65 | | methyl 8-bromo-1,6-naphthyridine-2-carboxylate |
| 66 | | 8-(3-thienyl)-1,6-naphthyridine-2-carboxylic acid |
| 67 | 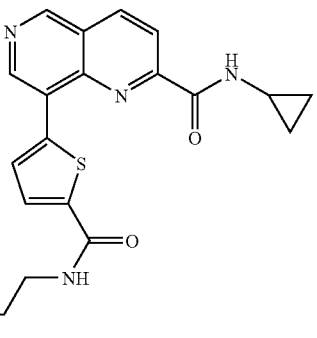 | N-cyclopropyl-8-[5-({[2-(diethylamino)ethyl]amino}carbonyl)-2-thienyl]-1,6-naphthyridine-2-carboxamide |
| 68 | | 8-phenyl-1,6-naphthyridine-2-carboxylic acid |
| 69 | | N-(2-furylmethyl)-8-{[4-(trifluoromethyl)phenyl]amino}-1,6-naphthyridine-2-carboxamide |
| 70 | | N-(2-furylmethyl)-8-[(4-methyiphenyl)amino]-1,6-naphthyridine-2-carboxamide |
| 71 | | 8-anilino-N-(2-furylmethyl)-1,6-naphthyridine-2-carboxamide |
| 72 | 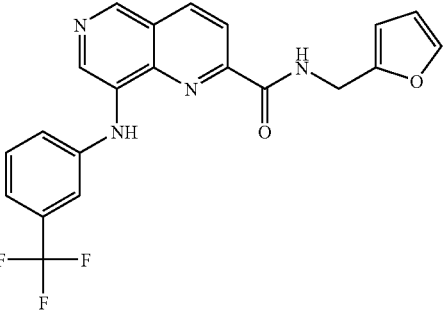 | N-(2-furylmethyl)-8-{[3-(trifluoromethyl)phenyl]amino}-1,6-naphthyridine-2-carboxamide |
| 73 | | N-(2-furylmethyl)-8-[(4-methoxyphenyl)amino]-1,6-naphthyridine-2-carboxamide |
| 74 | | N-(2-furylmethyl)-8-(3-hydroxyprop-1-yn-1-yl)-1,6-naphthyridine-2-carboxamide |
| 75 | | 8-(5-carboxy-2-thienyl)-1,6-naphthyridine-2-carboxylic acid |
| 76 | | 8-bromo-N-(2-oxocyclohexyl)-1,6-naphthyridine-2-carboxamide |

| Ex. No. | Structure | Name |
|---|---|---|
| 77 | (structure) | N-(2-furylmethyl)-8-(pyridin-3-ylamino)-1,6-naphthyridine-2-carboxamide |
| 78 | | tert-butyl[3-(2-{[(2-furylmethyl)amino]carbonyl}-1,6-naphthyridin-8-yl)prop-2-yn-1-yl]carbamate |
| 79 | | N-(2-furylmethyl)-8-(pyridin-4-ylamino)-1,6-naphthyridine-2-carboxamide |
| 80 | | 8-bromo-1,6-naphthyridine-2-carboxamide |
| 81 | | 8-(5-({[2-(diethylamino)ethyl]amino}carbonyl)-2-thienyl]-N-(2-furylmethyl)-1,6-naphthyridine-2-carboxamide |
| 82 | (structure) | 8-[5-({[2-(dimethylamino)ethyl]amino}carbonyl)-2-thienyl]-N-(2-furylmethyl)-1,6-naphthyridine-2-carboxamide |
| 83 | | N-cyclopropyl-8-[5-({[2-(dimethylamino)ethyl]amino}carbonyl)-2-thienyl]-1,6-naphthyridine-2-carboxamide |
| 84 | | diethyl N-(4-{[(8-bromo-1,6-naphthyridin-2-yl)carbonyl]amino}benzoyl)glutamate |
| 85 | | N-(2-furylmethyl)-8-(pyrazin-2-ylamino)-1,6-naphthyridine-2-carboxamide |
| 86 | | N-(2-oxocyclohexyl)-8-(3-thienyl)-1,6-naphthyridine-2-carboxamide |
| 87 | (structure) | N-(2-oxocyclohexyl)-8-phenyl-1,6-naphthyridine-2-carboxamide |

-continued

| Ex. No. | Structure | Name |
|---|---|---|
| 88 | | 8-(3-hydroxyprop-1-yn-1-yl)-1,6-naphthyridine-2-carboxamide |
| 89 | | N-cyclopropyl-8-(3-hydroxyprop-1-yn-1-yl)-1,6-naphthyridine-2-carboxamide |
| 90 | | N-(2-furylmethyl)-8-(phenylethynyl)-1,6-naphthyridine-2-carboxamide |
| 91 | | 8-ethynyl-N-(2-furylmethyl)-1,6-naphthyridine-2-carboxamide |
| 92 | structure | N-cyclopropyl-8-[(4-methoxyphenyl)amino]-1,6-naphthyridine-2-carboxamide |
| 93 | | 8-bromo-N-cyclopropyl-1,6-naphthyridine-2-carboxamide |
| 94 | | 8-bromo-N-(2-furylmethyl)-1,6-naphthyridine-2-carboxamide |
| 95 | | N-(2-furylmethyl)-8-(3-thienyl)-1,6-naphthyridine-2-carboxamide |
| 96 | | N-cyclopropyl-8-(3-thienyl)-1,6-naphthyridine-2-carboxamide |
| 97 | structure | 5-{2-[(cyclopropylamino)carbonyl]-1,6-naphthyridin-8-yl}thiophene-2-carboxylic acid |
| 98 | | 5-(2-{[(2-furylmethyl)amino]carbonyl}-1,6-naphthyridin-8-yl)thiophene-2-carboxylic acid |
| 99 | | N-methyl-8-(3-thienyl)-1,6-naphthyridine-2-carboxamide |
| 100 | | 8-(4-methoxyphenyl)-N-[(5-methylpyrazin-2-yl)methyl]-1,6-naphthyridine-2-carboxamide |
| 101 | | 8-(4-methoxyphenyl)-2-(morpholin-4-ylcarbonyl)-1,6-naphthyridine |

-continued

| Ex. No. | Structure | Name |
|---|---|---|
| 102 | 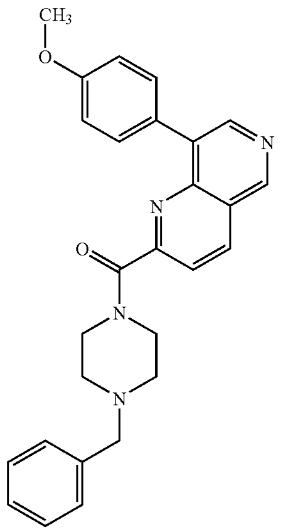 | 2-[(4-benzylpiperazin-1-yl)carbonyl]-8-(4-methoxyphenyl)-1,6-naphthyridine |
| 103 | | 8-phenyl-2-(piperidin-1-ylcarbonyl)-1,6-naphthyridine |
| 104 | | N-(3-morpholin-4-ylpropyl)-8-(3-thienyl)-1,6-naphthyridine-2-carboxamide |
| 105 | | 2-(morpholin-4-ylcarbonyl)-8-(3-thienyl)-1,6-naphthyridine |
| 106 | | N-[4-(methylsulfonyl)benzyl]-8-(3-thienyl)-1,6-naphthyridine-2-carboxamide |
| 107 | 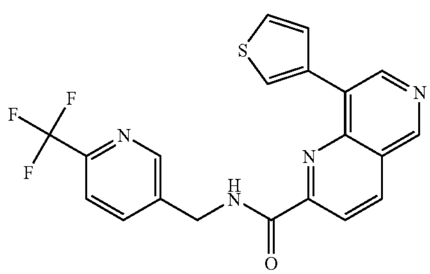 | 8-(3-thienyl)-N-{[6-(trifluoromethyl)pyridin-3-yl]methyl}-1,6-naphthyridine-2-carboxamide |
| 108 | | 1-{[8-(3-thienyl)-1,6-naphthyridin-2-yl]carbonyl}piperidin-4-ol |
| 109 | | N-(2-methoxyethyl)-8-(3-thienyl)-1,6-naphthyridine-2-carboxamide |
| 110 | | N-cyclopropyl-8-(3-thienyl)-1,6-naphthyridine-2-carboxamide |
| 111 | | 8-(4-methoxyphenyl)-N-(3-morpholin-4-ylpropyl)-1,6-naphthyridine-2-carboxamide |

-continued

| Ex. No. | Structure | Name |
|---|---|---|
| 112 | 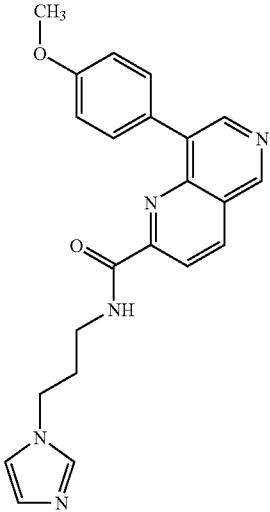 | N-[3-(1H-imidazol-1-yl)propyl]-8-(4-methoxyphenyl)-1,6-naphthyridine-2-carboxamide |
| 113 | | 8-(4-methoxyphenyl)-N-(pyridin-4-ylmethyl)-1,6-naphthyridine-2-carboxamide |
| 114 | | 8-(4-methoxyphenyl)-2-(piperidin-1-ylcarbonyl)-1,6-naphthyridine |
| 115 | | N-benzyl-8-(4-methoxyphenyl)-1,6-naphthyridine-2-carboxamide |
| 116 | | 8-(4-methoxyphenyl)-N-(2-phenylethyl)-1,6-naphthyridine-2-carboxamide |
| 117 | 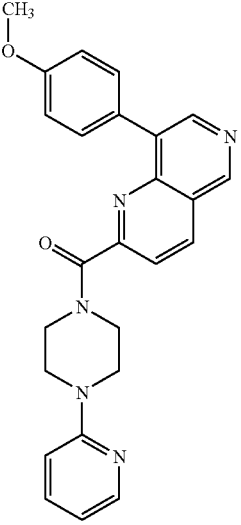 | 8-(4-methoxyphenyl)-2-[(4-pyridin-2-ylpiperazin-1-yl)carbonyl]-1,6-naphthyridine |
| 118 | | N-(1-benzylpiperidin-4-yl)-8-(4-methoxyphenyl)-1,6-naphthyridine-2-carboxamide |
| 119 | | N-(2-methoxybenzyl)-8-(4-methoxyphenyl)-1,6-naphthyridine-2-carboxamide |

-continued

| Ex. No. | Structure | Name |
|---|---|---|
| 120 | | N-[4-(dimethylamino)benzyl]-8-(4-methoxyphenyl)-1,6-naphthyridine-2-carboxamide |
| 121 | | 8-(4-methoxyphenyl)-N-[4-(methylsulfonyl)benzyl]-1,6-naphthyridine-2-carboxamide |
| 122 | 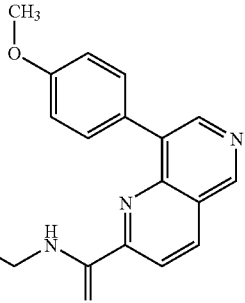 | 8-(4-methoxyphenyl)-N-{[6-(trifluoromethyl)pyridin-3-yl]methyl}-1,6-naphthyridine-2-carboxamide |
| 123 | | N-(3-morpholin-4-ylpropyl)-8-phenyl-1,6-naphthyridine-2-carboxamide |
| 124 | | N-[3-(1H-imidazol-1-yl)propyl]-8-phenyl-1,6-naphthyridine-2-carboxamide |
| 125 | | N-[(5-methylpyrazin-2-yl)methyl]-8-phenyl-1,6-naphthyridine-2-carboxamide |
| 126 | 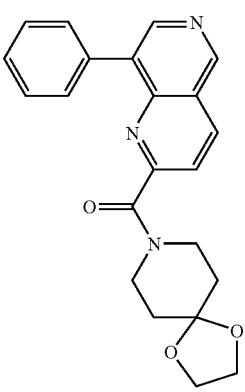 | 2-(1,4-dioxa-8-azaspiro[4,5]dec-8-ylcarbonyl)-8-phenyl-1,6-naphthyridine |
| 127 | | 8-phenyl-N-(pyridin-4-ylmethyl)-1,6-naphthyridine-2-carboxamide |
| 128 | | 2-(morpholin-4-ylcarbonyl)-8-phenyl-1,6-naphthyridine |
| 129 | | N-benzyl-8-phenyl-1,6-naphthyridine-2-carboxamide |
| 130 | | 8-phenyl-N-(2-phenylethyl)-1,6-naphthyridine-2-carboxamide |

| Ex. No. | Structure | Name |
|---|---|---|
| 131 | 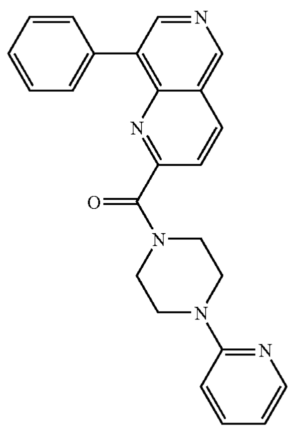 | 8-phenyl-2-[(4-pyridin-2-ylpiperazin-1-yl)carbonyl]-1,6-naphthyridine |
| 132 | | N-(4-chlorobenzyl)-8-phenyl-1,6-naphthyridine-2-carboxamide |
| 133 | | 2-[(4-benzylpiperazin-1-yl)carbonyl]-8-phenyl-1,6-naphthyridine |
| 134 | | N-(1-benzylpiperidin-4-yl)-8-phenyl-1,6-naphthyridine-2-carboxamide |
| 135 | | N-(2-methoxybenzyl)-8-phenyl-1,6-naphthyridine-2-carboxamide |
| 136 | 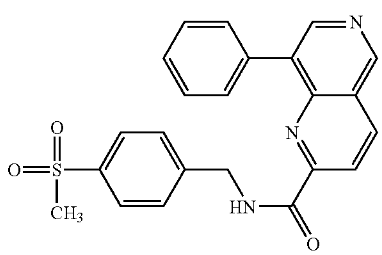 | N-[4-(methylsulfonyl)benzyl]-8-phenyl-1,6-naphthyridine-2-carboxamide |
| 137 | | 8-phenyl-N-{[6-(trifluoromethyl)pyridin-3-yl]methyl}-1,6-naphthyridine-2-carboxamide |
| 138 | | N-(2-isopropoxybenzyl)-8-phenyl-1,6-naphthyridine-2-carboxamide |
| 139 | | N-[3-(1H-imidazol-1-yl)propyl]-8-(3-thienyl)-1,6-naphthyridine-2-carboxamide |
| 140 | | 2-(1,4-dioxa-8-azaspiro[4.5]dec-8-ylcarbonyl)-8-(3-thienyl)-1,6-naphthyridine |
| 141 | 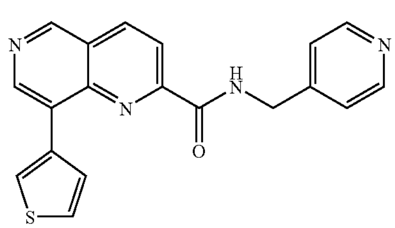 | N-(pyridin-4-ylmethyl)-8-(3-thienyl)-1,6-naphthyridine-2-carboxamide |

-continued

| Ex. No. | Structure | Name |
|---|---|---|
| 142 | | 2-(piperidin-1-ylcarbonyl)-8-(3-thienyl)-1,6-naphthyridine |
| 143 | | N-benzyl-8-(3-thienyl)-1,6-naphthyridine-2-carboxamide |
| 144 | | N-(2-furylmethyl)-8-(3-thienyl)-1,6-naphthyridine-2-carboxamide |
| 145 | | 2-[(4-pyridin-2-ylpiperazin-1-yl)carbonyl]-8-(3-thienyl)-1,6-naphthyridine |
| 146 | 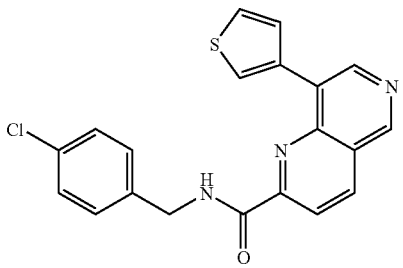 | N-(4-chlorobenzyl)-8-(3-thienyl)-1,6-naphthyridine-2-carboxamide |
| 147 | | 2-[(4-benzylpiperazin-1-yl)carbonyl]-8-(3-thienyl)-1,6-naphthyridine |
| 148 | | N-(1-benzylpiperidin-4-yl)-8-(3-thienyl)-1,6-naphthyridine-2-carboxamide |
| 149 | | N-(2-methoxybenzyl)-8-(3-thienyl)-1,6-naphthyridine-2-carboxamide |
| 150 | | 2-({4-[(4,6-dimethoxypyrimidin-2-yl)methyl]piperazin-1-yl}carbonyl)-8-(3-thienyl)-1,6-naphthyridine |
| 151 | 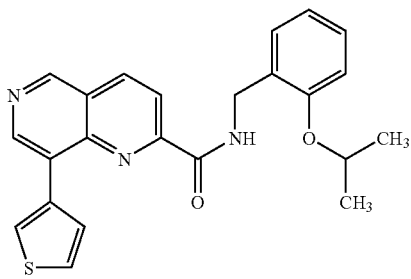 | N-(2-isopropoxybenzyl)-8-(3-thienyl)-1,6-naphthyridine-2-carboxamide |
| 152 | | 1-{[8-(1-benzofuran-2-yl)-1,6-naphthyridin-2-yl]carbonyl}piperidin-4-ol |
| 153 | | 8-(1-benzofuran-2-yl)-N-(2-methoxyethyl)-1,6-naphthyridine-2-carboxamide |
| 154 | | 8-(1-benzofuran-2-yl)-N-cyclopropyl-1,6-naphthyridine-2-carboxamide |

US 7,282,506 B2

91                                                                92

-continued

| Ex. No. | Structure | Name |
|---|---|---|
| 155 | | 1-[(8-phenyl-1,6-naphthyridin-2-yl)carbonyl]piperidin-4-ol |
| 156 | 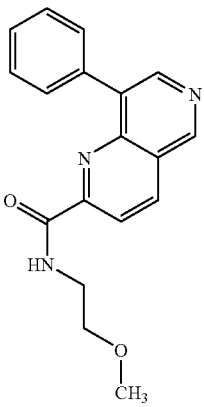 | N-(2-methoxyethyl)-8-phenyl-1,6-naphthyridine-2-carboxamide |
| 157 | | N-cyclopropyl-8-phenyl-1,6-naphthyridine-2-carboxamide |
| 158 | | 8-(1-benzofuran-2-yl)-N-(3-morpholin-4-ylpropyl)-1,6-naphthyridine-2-carboxamide |
| 159 | | 8-(1-benzofuran-2-yl)-N-[3-(1H-imidazol-1-yl)propyl]-1,6-naphthyridine-2-carboxamide |
| 160 | | 8-(1-benzofuran-2-yl)-N-[(5-methylpyrazin-2-yl)methyl]-1,6-naphthyridine-2-carboxamide |
| 161 | 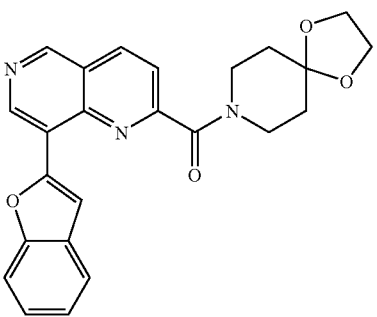 | 8-(1-benzofuran-2-yl)-2-(1,4-dioxa-8-azaspiro[4.5]dec-8-ylcarbonyl)-1,6-naphthyridine |
| 162 | | 8-(1-benzofuran-2-yl)-N-(pyridin-4-ylmethyl)-1,6-naphthyridine-2-carboxamide |
| 163 | | 8-(1-benzofuran-2-yl)-2-(morpholin-4-ylcarbonyl)-1,6-naphthyridine |
| 164 | | 8-(1-benzofuran-2-yl)-2-(piperidin-1-ylcarbonyl)-1,6-naphthyridine |
| 165 | | 8-(1-benzofuran-2-yl)-N-benzyl-1,6-naphthyridine-2-carboxamide |

-continued

| Ex. No. | Structure | Name |
|---|---|---|
| 166 | 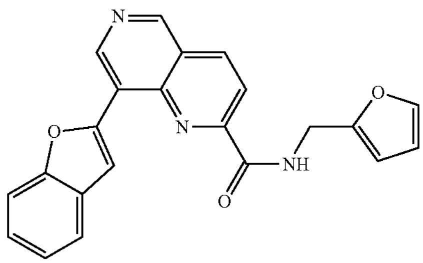 | 8-(1-benzofuran-2-yl)-N-(2-furylmethyl)-1,6-naphthyridine-2-carboxamide |
| 167 | | 8-(1-benzofuran-2-yl)-N-(2-phenylethyl)-1,6-naphthyridine-2-carboxamide |
| 168 | | 8-(1-benzofuran-2-yl)-N-(4-chlorobenzyl)-1,6-naphthyridine-2-carboxamide |
| 169 | | 8-(1-benzofuran-2-yl)-2-[(4-benzylpiperazin-1-yl)carbonyl]-1,6-naphthyridine |
| 170 | | 8-(1-benzofuran-2-yl)-N-(1-benzylpiperidin-4-yl)-1,6-naphthyridine-2-carboxamide |
| 171 | 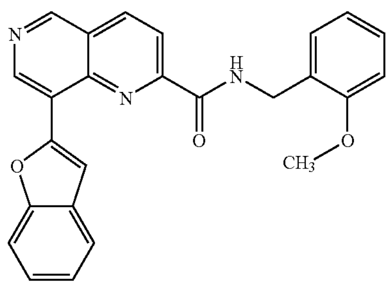 | 8-(1-benzofuran-2-yl)-N-(2-methoxybenzyl)-1,6-naphthyridine-2-carboxamide |
| 172 | | 8-(1-benzofuran-2-yl)-N-[4-(methylsulfonyl)benzyl]-1,6-naphthyridine-2-carboxamide |
| 173 | 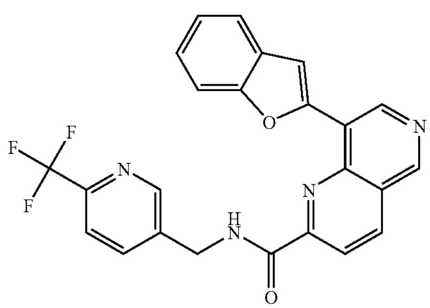 | 8-(1-benzofuran-2-yl)-N-{[6-(trifluoromethyl)pyridin-3-yl]methyl}-1,6-naphthyridine-2-carboxamide |
| 174 | | 8-(1-benzofuran-2-yl)-N-(2-isopropoxybenzyl)-1,6-naphthyridine-2-carboxamide |

Biological Evaluation

Endothelial Cell Activation:

Low passage normal human umbilical vein endothelial cells (HUVEC) (Clonetics) were seeded 20,000 cells per well into 96-well assay plates and incubated at 37° C. overnight in a 5% $CO_2$ atmosphere. The following day, 10× test compounds and controls were added to the appropriate wells and the treated cells returned to the incubator for one hour. Cells were then activated by adding TNF-α to a final concentration of 1 ng/ml and incubating for an additional 4 hours. After activation, media was removed and the cell monolayer was fixed by adding 100 μl/well of 100% methanol. Expression of E-selectin was then determined by performing an ELISA with an E-selectin-specific primary antibody. Compound activity was determined by comparing E-selectin expression levels to the DMSO and 10 μM Actinomycin D controls.

To test for specificity of compound action, the endothelial cells were also activated with 1 ng/ml IL-1β or LPS. 18 hour activation was also done for all three agonist, but cell activation for the longer activation was measured by determining expression of ICAM using an ICAM-specific primary antibody for the ELISA readout.

TNF-α Activation of NFκB Response Element:

293T cells were transfected with an NFκB-Luc reporter construct (BD Biosystems) using FuGENE 6 transfection reagent (Roche). After transfection, the cells were plated into 96-well plates and incubated at 37° C. overnight in a 5% $CO_2$ atmosphere. The following day, 10× concentrations of test compounds and controls were added to the appropriate wells, and the cells were incubated for an additional hour. TNF-α was then added to a final concentration of 5 ng/ml, followed by additional 4 hour incubation. After activation the media was removed and 30 μl/well of reporter lysis buffer was added (Promega). Luciferase activity was determined by adding luciferase reaction buffer (Promega) to the plate and measuring light output with a Tecan GeniosPro plate reader. Compound activity was determined by comparing light output to DMSO and 10 μM Actinomycin D controls.

LPS Activated TNF-α Release:

THP-1 cells were seeded into V-bottom 96-well plates at 5,000 cells per well. Plates were then incubated overnight at 37° C., 5% $CO_2$. Cells were then treated with 10× compounds, using DMSO and 10 μM Actinomycin-D as controls. Plates were incubated for 1 hr at 37° C., 5% $CO_2$. Cells were then activated with 10× LPS (final concentration: 25 ng/ml) and incubated overnight at 37° C., 5% $CO_2$. The following day, assay plates were centrifuged, and the supernatant transferred to ELISA plates for determination of TNF-α secretion by sandwich ELISA (Biosource International).

TNF-α Activated IL-8 Release:

HL60 cells were seeded into V-bottom 96-well plates at 20,000 cells per well and treated with test compounds ranging in concentration from 40 μM to 64 nM, using DMSO and 10 μM Actinomycin D as the controls. Plates were incubated for 1 hour at 37° C., 5% $CO_2$. Cells were then activated by addition of TNF-α (final concentration: 12.5 ng/ml). Plates were incubated for an additional 4 hours at 37° C., 5% $CO_2$. Plates were then centrifuged, and supernatant transferred to ELISA plates for determination of IL-8 secretion by sandwich ELISA.

Cell Proliferation Assays

A panel of cancer cell lines was obtained from the DCTP Tumor Repository, National Cancer Institute (Frederick, Md.) or ATCC (Rockville, Md.). Cell cultures were maintained in Hyclone RPMI 1640 medium (Logan, Utah) supplemented with 10% fetal bovine serum and 20 mM HEPES buffer, final pH 7.2, at 37° C. with a 5% CO2 atmosphere. Cultures were maintained at sub-confluent densities. Human umbilical vein endothelial cells (HUVEC) were purchased from Clonetics, a division of Cambrex (Walkersville, Md.). Cultures were established from cryopreserved stocks using Clonetics EGM-2 medium supplemented with 20 mM HEPES, final pH 7.2, at 37° C. with a 5% $CO_2$ atmosphere.

For proliferation assays, cells were seeded with the appropriate medium into 96 well plates at 1,000-2,500 cells per well, depending on the cell line, and were incubated overnight. The following day, test compound, DMSO solution (negative control), or Actinomycin D (positive control) was added to the appropriate wells as 10× concentrated stocks prepared in phosphate buffered saline. The cell plates were then incubated for an additional 2-5 days, depending on the cell line, to allow proliferation to occur. To measure cell density, 50 μL of WST-1 solution (Roche Applied Science, IN) diluted 1:5 in phosphate buffered saline was added to each well, and the cells incubated for an additional 1-5 hrs., again depending on the cell line. Optical density was determined for each well at 450 nM using a Tecan GeniosPro plate reader (RTP, NC). The percentage of cell growth was determined by comparing the cell growth in the presence of test compounds to the cells treated with DMSO vehicle (control, 100% growth) and cells treated with Actinomycin D (10 μM, 0% growth).

Immediately after the WST-1 determination, the medium was removed from the PC-3, NCI-H460 and HUVEC cell lines, and the plates stored at −80° C. Using these assay plates, relative amounts of DNA in each well were determined using the Cyquant DNA assay kit from R&D Systems (Eugene, Oreg.) following the manufacturer's directions. Results for each compound treatment were compared to DMSO vehicle control (100%) and 10 μM Actinomycin D treated cells (0%). Table 2 contains the cell proliferation data for several exemplary compounds useful in the methods of the invention.

Preferred compounds of the invention have activities of less than 20 μM in all of the assays described above.

The invention and the manner and process of making and using it, are now described in such full, clear, concise and exact terms as to enable any person skilled in the art to which it pertains, to make and use the same. It is to be understood that the foregoing describes preferred embodiments of the invention and that modifications may be made therein without departing from the spirit or scope of the invention as set forth in the claims. To particularly point out and distinctly claim the subject matter regarded as invention, the following claims conclude this specification.

What is claimed is:

1. A compound of the formula:

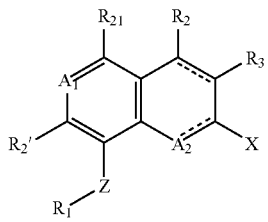

or a pharmaceutically acceptable salt thereof, wherein each ----- independently represents a single bond or a double bond;

$A_1$ is N, or an N-oxide;

$A_2$ is N, an N-oxide, NH, or $N(C_1-C_6)$ alkyl; provided that when ----- is a single bond, then $A_2$ is NH, or $N(C_1-C_6)$ alkyl;

X is $NR_xR_y$, or $-C(O)R_{20}$; wherein $R_x$ and $R_y$ are independently H, $C_1$-$C_6$ alkyl, alkoxycarbonyl, arylalkoxycarbonyl, aryl, arylalkyl, —C(O)—aryl, heteroaryl, heteroarylalkyl, or —C(O) heteroaryl;

Z is a bond, —$CH_2$—, —NH—, —O—, —N($C_1$-$C_6$ alkyl)—, —S—, —S(O)—, —$SO_2$—, —$SO_2$NH—, or —$SO_2$N($C_1$-$C_6$ alkyl)—;

$R_1$ is $C_1$-$C_6$ alkanoyl, $C_2$-$C_6$ alkynyl, aryl, heteroaryl, heterocycloalkyl, or $C_3$-$C_8$ cycloalkyl, each of which is unsubstituted or substituted with 1, 2, 3, 4, or 5 groups that are independently $C_1$-$C_6$ alkyl, halogen, $C_1$-$C_6$ alkoxy, OH, CN, $CO_2H$, $C_1$-$C_4$ haloalkyl, $C_1$-$C_4$ haloalkoxy, —OC(O)—$C_1$-$C_6$ alkyl, $C_1$-$C_6$ alkoxycarbonyl, $C_1$-$C_6$ alkanoyl, —C(O)$R_{10}$, $NR_6R_7$, —($C_1$-$C_4$ alkyl)—$NR_6R_7$, —C(O)$NR_6R_7$, phenyl, or naphthyl, wherein the phenyl and naphthyl groups are optionally substituted with 1 or more groups that are independently selected from $C_1$-$C_4$ alkyl, $C_1$-$C_4$ alkoxy, halogen, OH, $CF_3$, and $OCF_3$, wherein each $R_6$ and $R_7$ is independently H, $C_1$-$C_6$ alkyl, $C_1$-$C_4$ alkoxyalkyl, $C_1$-$C_6$ alkoxycarbonyl, wherein the alkyl portion of each is unsubstituted or substituted with 1, 2, or 3, groups that are independently halogen, OH, $C_1$-$C_4$ haloalkyl, $C_1$-$C_4$ haloalkoxy, $NH_2$, NH($C_1$-$C_6$ alkyl) or N ($C_1$-$C_6$ alkyl) ($C_1$-$C_6$ alkyl); or $R_6$ and $R_7$ and the nitrogen to which they are attached form a ring having from 5 to 8 members, wherein the ring optionally contains 1-3 additional heteroatoms selected from N, O, and S, where the ring is optionally substituted with 1, 2, or 3 groups that are independently $C_1$-$C_6$ alkyl, $C_1$-$C_6$ alkoxy, halogen, amino, NH ($C_1$-$C_6$ alkyl), or N ($C_1$-$C_6$ alkyl) ($C_1$-$C_6$ alkyl);

$R_{10}$ is $C_2$-$C_6$ alkenyl, $C_2$-$C_6$ alkynyl, aryl, heteroaryl, or cycloalkyl, wherein the cyclic portions are optionally substituted with 1, 2, or 3 groups that are independently halogen, $C_1$-$C_6$ alkyl, $C_1$-$C_6$ alkoxy, OH, $CO_2H$, CN, $NO_2$, $C_1$-$C_4$ haloalkyl, or $C_1$-$C_4$ haloalkoxy;

wherein the heterocycloalkyl and the cycloalkyl portions of $R_1$ and $R_{10}$ are further optionally substituted with =O, =N—OH, or =N—$OCH_3$;

$R_2$, $R_2'$, and $R_3$ are independently H, halogen, $C_1$-$C_6$ alkyl, $C_2$-$C_6$ alkynyl, $C_2$-$C_6$ alkenyl, —C(O)$NH_2$, —C(O)NH ($C_1$-$C_6$ alkyl) —C(O)N($C_1$-$C_6$ alkyl) ($C_1$-$C_6$ alkyl), or aryl;

$R_{20}$ is H, OH, $C_1$-$C_6$ alkoxy, or $NR_4R_5$; wherein $R_4$ and $R_5$ are independently H, $C_1$-$C_6$ alkyl, $C_1$-$C_4$ alkoxy $C_1$-$C_6$ alkyl, $C_2$-$C_6$ alkynyl, $C_2$-$C_6$ alkenyl, $C_3$-$C_8$ cycloalkyl, cycloalkylalkyl, cycloalkylalkenyl, cycloalkylalkynyl, heterocycloalkyl, heterocycloalkylalkyl, heterocycloalkylalkenyl, heterocycloalkylalkynyl, aryl, heteroaryl, heteroarylalkyl, heteroarylalkenyl, heteroarylalkynyl, arylalkyl, arylalkenyl, or arylalkynyl, wherein the cyclic portion of each of the above is unsubstituted or substituted with one or more groups that are independently $C_1$-$C_6$ alkyl, $C_1$-$C_6$ alkoxy, halogen, —$SO_2$— ($C_1$-$C_6$) alkyl, $C_1$-$C_4$ haloalkyl, $C_1$-$C_4$ haloalkoxy, $NO_2$, CN, OH, aryl $C_1$-$C_6$ alkyl, $C_1$-$C_6$ alkoxy $C_1$-$C_6$ alkyl, $C_1$-$C_6$ alkoxycarbonyl, $C_1$-$C_6$ alkanoyl, $NR_7R_8$, or —C(O)$NR_7R_8$, wherein $R_7$ and $R_8$ are independently H or $C_1$-$C_6$ alkyl, wherein the alkyl is optionally substituted with 1, 2, or 3 groups that are independently $C_1$-$C_6$ alkoxycarbonyl, halogen, $C_1$-$C_6$ alkoxy, $C_1$-$C_6$ alkanoyl, $NH_2$, NH($C_1$-$C_6$ alkyl), N($C_1$-$C_6$ alkyl) ($C_1$-$C_6$ alkyl) or $CO_2H$; or $R_7$ and $R_8$ and the nitrogen to which they are attached form a ring having from 5 to 8 members, wherein the ring optionally contains 1-3 additional heteroatoms selected from N, O, and S, where the ring is optionally substituted with 1, 2, or 3 groups that are independently $C_1$-$C_6$ alkyl, $C_1$-$C_6$ alkoxy, halogen, amino, NH($C_1$-$C_6$ alkyl), or N($C_1$-$C_6$ alkyl) ($C_1$-$C_6$ alkyl);

wherein the heterocycloalkyl and the cycloalkyl portions of $R_4$ and $R_5$ are further optionally substituted with =O, =N—OH, or =N—$OCH_3$; or $R_4$ and $R_5$ and the nitrogen to which they are attached form a heterocycloalkyl ring, which is unsubstituted or substituted with 1 or more groups that are independently $C_1$-$C_6$ alkyl, $C_1$-$C_6$ alkoxy, halogen, aryl $C_1$-$C_6$ alkyl, $C_1$-$C_6$ alkanoyl, OH, =O, heteroaryl, heteroarylalkyl, phenyl, naphthyl, —$OCH_2$-$CH_2O$—, —$OCH_2O$—, wherein the heteroaryl, phenyl and naphthyl groups are unsubstituted or substituted with 1 or more groups that are independently $C_1$-$C_4$ alkyl, $C_1$-$C_4$ alkoxy, halogen, $CF_3$ or $OCF_3$;

$R_{21}$ is H, CN, amino, monoalkylamino, dialkylamino, OH, halogen, aryl, heteroaryl, $C_1$-$C_6$ alkyl, $C_2$-$C_6$ alkynyl, $C_2$-$C_6$ alkenyl, —C(O)$NH_2$, —C(O)NH($C_1$-$C_6$ alkyl), or —C(O)N($C_1$-$C_6$ alkyl) ($C_1$-$C_6$ alkyl);

provided that when $R_{20}$ is $NR_4R_5$ and $R_4$ is $C_{1-6}$ alkyl, $C_{2-6}$ alkenyl or $C_{3-7}$ cyoloalkyl optionally substituted with OH, halogen, amino, carboxyl or saturated or unsaturated $C_{3-10}$ (carbocycle or heterocycle) optionally substituted with OH, halogen, amino, mercapto, carboxy, $C_{1-4}$ (alkyl, alkoxy, alkylthio, acyl, acyloxy or alkoxycarbonyl) optionally substituted with OH, halogen, amino or $C_{1-4}$ alkoxy; and $C_{3-7}$ cycloalkyl fused to $C_{6-10}$ aryl optionally substituted with OH, halogen, amino, mercapto, carboxy, $C_{1-4}$ (alkyl, alkoxy, alkylthio, acyl, acyloxy or alkoxycarbonyl) optionally substituted with OH, halogen, amino or $C_{1-4}$ alkoxy;

$R_5$ is H, or $C_{1-4}$ alkyl; and (1) Z is a bond; and $R_2$ or $R_3$ is H, OH, halogen, amino, cyano, $C_{1-6}$ (alkyl, alkoxy, acyl, acyloxy or alkoxycarbonyl) optionally substituted with OH, halogen, amino or $C_{1-4}$ alkoxy, and saturated or unsaturated $C_{3-10}$ (carbocycle or heterocycle) optionally substituted with OH, halogen, amino, mercapto, $C_{1-4}$ alkylthio, $C_{1-4}$ alkoxycarbonyl, halo substituted $C_{1-4}$ alkyl or halo-substituted $C_{1-4}$ alkoxy, $C_{1-4}$ alkyl, $C_{1-4}$ alkoxy or carboxy; or (2) Z is a bond;

$R_2$ or $R_3$ is H, OH, halogen, amino, cyano, $C_{1-6}$ (alkyl, alkoxy, acyl, acyloxy or alkoxycarbonyl) optionally substituted with OH, halogen, amino or $C_{1-4}$ alkoxy, and saturated or unsaturated $C_{3-10}$ (carbocycle or heterocycle) optionally substituted with OH, halogen, amino, mercapto, $C_{1-4}$ alkylthio, $C_{1-4}$ alkoxycarbonyl, halo substituted $C_{1-4}$ alkyl or halo-substituted $C_{1-4}$ alkoxy, $C_{1-4}$ alkyl, $C_{1-4}$ alkoxy or carboxy; and $R_4$ and $R_5$ together form a saturated or unsaturated 5 or 6 member heterocycle optionally fused to $C_{6-10}$ aryl or heteroaryl; then $R_1$ is not OH, amino, cyano, $C_{1-6}$ (alkoxy, acyl, acyloxy or alkoxycarbonyl) optionally substituted with OH, halogen, amino or $C_{1-4}$ alkoxy, and saturated or unsaturated $C_{3-10}$ (carbocycle or heterocycle) optionally substituted with OH, halogen, amino, mercapto, $C_{1-4}$ alkylthio, $C_{1-4}$ alkoxycarbonyl, halo substituted $C_{1-4}$ alkyl or halo-substituted $C_{1-4}$ alkoxy, $C_{1-4}$ alkyl, $C_{1-4}$ alkoxy or carboxy.

2. A compound according to claim 1, wherein $R_1$ is $C_1$-$C_6$ alkanoyl, $C_2$-$C_6$ alkynyl, phenyl, naphthyl, thienyl, furanyl, indolyl, pyridyl, pyridazinyl, pyrimidyl, pyrazinyl, triazolyl, imidazolyl, oxazolyl, isoxazolyl, benzofuranyl, 3,4 dihydropyrimidin-2 (1H)—onyl, piperidinyl, pyrrolidinyl, piperazinyl, morpholinyl, thiomorpholinyl, S,S -dioxothiomorpholinyl, or $C_3$-$C_8$ cycloalkyl, each of which is unsubstituted or substituted with 1, 2, 3, 4, or 5 groups that are independently $C_1$-$C_6$ alkyl, halogen, $C_1$-$C_6$ alkoxy, OH, ON, $CO_2H$, phenyl, naphthyl, wherein the phenyl and naphthyl groups are optionally substituted with 1 or more groups that are independently selected from $C_1$-$C_4$ alkyl, $C_1$-$C_{C4}$ alkoxy, halogen, OH, $CF_3$, and $OCF_3$, $C_1$-$C_4$ haloalkyl, $C_1$-$C_4$ haloalkoxy, —OC(O)— $C_1$-$C_6$ alkyl, $C_1$-$C_6$ alkoxycarbonyl, $C_1$-$C_6$ alkanoyl, —C(O)$R_{10}$, $NR_6R_7$, —($C_1$-$C_4$ alkyl)-$NR_6R_7$, or —C(O)$NR_6R_7$, wherein Each $R_6$ and $R_7$ is independently H, $C_1$-$C_6$ alkyl, $C_1$-$C_4$ alkoxyalkyl, $C_1$-$C_6$ alkoxycarbonyl, wherein the alkyl portion of each is unsubstituted or substituted with 1, 2, or 3, groups that are independently halogen, OH, $C_1$-$C_4$ haloalkyl, $C_1$-$C_4$ haloalkoxy, $NH_2$, NH($C_1$-$C_6$ alkyl) or N($C_1$-$C_6$ alkyl) ($C_1$-$C_6$ alkyl);

$R_{10}$ is $C_2$-$C_6$ alkenyl, $C_2$-$C_6$ alkynyl, phenyl, naphthyl, pyridyl, quinolinyl, pyrimidyl, furanyl, indolyl, benzofuranyl, thienyl, cycloalkyl, wherein the cyclic portions are optionally substituted with halogen, $C_1$-$C_6$ alkyl, $C_1$-$C_6$ alkoxy, OH, $CO_2H$, CN, $NO_2$, $C_1$-$C_4$ haloalkyl, or $C_1$-$C_4$ haloalkoxy;

wherein the heterocycloalkyl and the cycloalkyl portions of $R_1$ and $R_{10}$ are further optionally substituted with =O, =N—OH, or =N—$OCH_3$.

3. A compound according to claim 1, wherein $R_{20}$ is $NR_4R_5$; wherein $R_4$ and $R_5$ are independently H, $C_1$-$C_6$ alkyl, $C_1$-$C_4$ alkoxy $C_1$-$C_6$ alkyl, $C_2$-$C_6$ alkynyl, $C_2$-$C_6$ alkenyl, $C_3$-$C_8$ cycloalkyl, $C_3$-$C_8$ cycloalkyl $C_1$-$C_6$ alkyl, $C_3$-$C_8$ cycloalkyl $C_2$-$C_6$ alkenyl, cycloalkyl $C_2$-$C_6$ alkynyl, piperidinyl, pyrrolidinyl, imidazolidinyl, morpholinyl, thiomorpholinyl, S,S-dioxothiomorpholinyl, tetrahydrofuranyl, tetrahydrothienyl, morpholinyl $C_1$-$C_6$ alkyl, thiomorpholinyl $C_1$-$C_6$ alkyl, S,S-dioxothiomorpholinyl $C_1$-$C_6$ alkyl, piperidinyl $C_1$-$C_6$ alkyl, pyrrolidinyl $C_1$-$C_6$ alkyl, imidazolidinyl $C_1$-$C_6$ alkyl, piperidinyl $C_2$-$C_6$ alkenyl, pyrrolidinyl $C_2$-$C_6$ alkenyl, imidazolidinyl $C_2$-$C_6$ alkenyl, morpholinyl $C_2$-$C_6$ alkenyl, thiomorpholinyl $C_2$-$C_6$ alkenyl, S,S-dioxothiomorpholinyl $C_2$-$C_6$ alkenyl, tetrahydrofuranyl $C_2$-$C_6$ alkenyl, tetrahydrothienyl $C_2$-$C_6$ alkenyl, piperidinyl $C_2$-$C_6$ alkynyl, pyrrolidinyl $C_2$-$C_6$ alkynyl, imidazolidinyl $C_2$-$C_6$ alkynyl, morpholinyl $C_2$-$C_6$ alkynyl, thiomorpholinyl $C_2$-$C_6$ alkynyl, S,S-dioxothiomorpholinyl $C_2$-$C_6$ alkynyl, tetrahydrofuranyl $C_2$-$C_6$ alkynyl, tetrahydrothienyl $C_2$-$C_6$ alkynyl, phenyl, naphthyl, furanyl, pyridyl, pyrimidyl, pyrazinyl, thienyl, imidazolyl, pyrazinyl $C_1$-$C_6$ alkyl, pyridyl $C_1$-$C_6$ alkyl, pyrimidyl $C_1$-$C_6$ alkyl, pyrazinyl $C_1$-$C_6$ alkyl, imidazolyl $C_1$-$C_6$ alkyl, furanyl $C_1$-$C_6$ alkyl, thienyl $C_1$-$C_6$ alkyl, heteroarylalkenyl, heteroarylalkynyl, phenyl $C_1$-$C_6$ alkyl, naphthyl $C_1$-$C_6$ alkyl, phenyl $C_2$-$C_6$ alkenyl, naphthyl $C_2$-$C_6$ alkenyl, phenyl $C_2$-$C_6$ alkynyl, naphthyl $C_2$-$C_6$ alkynyl, wherein the cyclic portion of each of the above is unsubstituted or substituted with one or more groups that are independently $C_1$-$C_6$ alkyl, $C_1$-$C_6$ alkoxy, halogen, —$SO_2$—($C_1$-$C_6$) alkyl, $C_1$-$C_4$ haloalkyl, $C_1$-$C_4$ haloalkoxy, $NO_2$, CN, OH, phenyl $C_1$-$C_6$ alkyl wherein the phenyl is optionally substituted with 1, 2, 3, 4, or 5 groups that are independently selected from $C_1$-$C_4$ alkyl, $C_1$-$C_4$ alkoxy, CN, halogen, OH, and alkanoyl, $C_1$-$C_6$ alkoxy $C_1$-$C_6$ alkyl, $C_1$-$C_6$ alkoxycarbonyl, $C_1$-$C_6$ alkanoyl, $NR_7R_8$, or —C(O)$NR_7R_8$, wherein $R_7$ and $R_8$ are independently H or $C_1$-$C_6$ alkyl, wherein the $C_1$-$C_6$ alkyl is optionally substituted with 1, 2, or 3 groups that are independently $C_1$-$C_6$ alkoxycarbonyl, halogen, $C_1$-$C_6$ alkoxy, $C_1$-$C_6$ alkanoyl, $NH_2$, NH($C_1$-$C_6$ alkyl), N($C_1$-$C_6$ alkyl) ($C_1$-$C_6$ alkyl) or $CO_2H$;

wherein the heterocycloalkyl and the cycloalkyl portions of $R_4$ and $R_5$ are further optionally substituted with =O, =N—OH, or =N—$OCH_3$; or $R_4$ and $R_5$ and the nitrogen to which they are attached form a piperazinyl, morpholinyl, piperidinyl, pyrrolidinyl, thiomorpholinyl, imidazolidinyl, S,S,-dioxothiomorpholinyl, piperidinyl, pyrrolidinyl, ring, which is unsubstituted or substituted with 1 or more groups that are independently $C_1$-$C_6$ alkyl, $C_1$-$C_6$ alkoxy, halogen, phenyl $C_1$-$C_6$ alkyl, naphthyl $C_1$-$C_6$ alkyl, $C_1$-$C_6$ alkanoyl, OH, =O, pyridyl, pyrimidyl, pyrazinyl, pyrimidyl $C_1$-$C_6$ alkyl, pyrazinyl $C_1$-$C_6$ alkyl, phenyl, naphthyl, —$OCH_2CH_2O$—, —$OCH_2O$—, wherein the pyridyl, pyrimidyl, pyrazinyl, pyrimidyl $C_1$-$C_6$ alkyl, phenyl and naphthyl groups are unsubstituted or substituted with 1 or more groups that are independently $C_1$-$C_4$ alkyl, $C_1$-$C_4$ alkoxy, halogen, $CF_3$ or $OCF_3$.

4. A compound according to claim 1, wherein $R_1$ is $C_1$-$C_6$ alkanoyl, $C_2$-$C_6$ alkynyl, phenyl, naphthyl, thienyl, furanyl, indolyl, pyridyl, pyridazinyl, pyrimidyl, pyrazinyl, triazolyl, imidazolyl, oxazolyl, isoxazolyl, benzofuranyl, 3,4-dihydropyrimidin-2(1H)-onyl, piperidinyl, pyrrolidinyl, piperazinyl, morpholinyl, thiomorpholinyl, S,S-dioxothiomorpholinyl, or $C_3$-$C_8$ cycloalkyl, each of which is unsubstituted or substituted with 1, 2, 3, 4, or 5 groups that are independently $C_1$-$C_6$ alkyl, halogen, $C_1$-$C_6$ alkoxy, OH, CN, $CO_2H$, phenyl, naphthyl, wherein the phenyl and naphthyl groups are optionally substituted with 1 or more groups that are independently selected from $C_1$-$C_4$ alkyl, $C_1$-$C_4$ alkoxy, halogen, OH, $CF_3$, and $OCF_3$, $C_1$-$C_4$ haloalkyl, $C_1$-$C_4$ haloalkoxy, —OC(O)— $C_1$-$C_6$ alkyl, $C_1$-$C_6$ alkoxycarbonyl, $C_1$-$C_6$ alkanoyl, —C(O)$R_{10}$, $NR_6R_7$, —($C_1$-$C_4$ alkyl)-$NR_6R_7$, or —C(O)$NR_6R_7$, wherein each $R_6$ and $R_7$ is independently H, $C_1$-$C_6$ alkyl, $C_1$-$C_4$ alkoxyalkyl, $C_1$-$C_6$ alkoxycarbonyl, wherein the alkyl portion of each is unsubstituted or substituted with 1, 2, or 3 groups that are independently halogen, OH, $C_1$-$C_4$ haloalkyl, $C_1$-$C_4$ haloalkoxy, $NH_2$, NH($C_1$-$C_6$ alkyl) or N($C_1$-$C_6$ alkyl) ($C_1$-$C_6$ alkyl);

$R_{10}$ is $C_2$-$C_6$ alkenyl, $C_2$-$C_6$ alkynyl, phenyl, naphthyl, pyridyl, quinolinyl, pyrimidyl, furanyl, indolyl, $C_3$-$C_8$ cycloalkyl, wherein the cyclic portions are optionally substituted with halogen, $C_1$-$C_6$ alkyl, $C_1$-$C_6$ alkoxy, OH, $CO_2H$, CN, $NO_2$, $C_1$-$C_4$ haloalkyl, or $C_1$-$C_4$ haloalkoxy;

wherein the heterocycloalkyl and the cycloalkyl portions of $R_1$ and $R_{10}$ are further optionally substituted with =O, =N—OH, or =N—OCH$_3$; and $R_4$ and $R_5$ are independently H, $C_1$-$C_6$ alkyl, $C_1$-$C_4$ alkoxy $C_1$-$C_6$ alkyl, $C_2$-$C_6$ alkynyl, $C_2$-$C_6$ alkenyl, $C_3$-$C_8$ cycloalkyl, $C_3$-$C_8$ cycloalkyl $C_1$-$C_6$ alkyl, $C_3$-$C_8$ cycloalkyl $C_2$-$C_6$ alkenyl, cycloalkyl $C_2$-$C_6$ alkynyl, piperidinyl, pyrrolidinyl, imidazolidinyl, morpholinyl, thiomorpholinyl, S,S-dioxothiomorpholinyl, tetrahydrofuranyl, tetrahydrothienyl, morpholinyl $C_1$-$C_6$ alkyl, thiomorpholinyl $C_1$-$C_6$ alkyl, S,S-dioxothiomorpholinyl $C_1$-$C_6$ alkyl, piperidinyl $C_1$-$C_6$ alkyl, pyrrolidinyl $C_1$-$C_6$ alkyl, imidazolidinyl $C_1$-$C_6$ alkyl, piperidinyl $C_2$-$C_6$ alkenyl, pyrrolidinyl $C_2$-$C_6$ alkenyl, imidazolidinyl $C_2$-$C_6$ alkenyl, morpholinyl $C_2$-$C_6$ alkenyl, thiomorpholinyl $C_2$-$C_6$ alkenyl, S,S-dioxothiomorpholinyl $C_2$-$C_6$ alkenyl, tetrahydrofuranyl $C_2$-$C_6$ alkenyl, tetrahydrothienyl $C_2$-$C_6$ alkenyl, piperidinyl $C_2$-$C_6$ alkynyl, pyrrolidinyl $C_2$-$C_6$ alkynyl, imidazolidinyl $C_2$-$C_6$ alkynyl, morpholinyl $C_2$-$C_6$ alkynyl, thiomorpholinyl $C_2$-$C_6$ alkynyl, S,S-dioxothiomorpholinyl $C_2$-$C_6$ alkynyl, tetrahydrofuranyl $C_2$-$C_6$ alkynyl, tetrahydrothienyl $C_2$-$C_6$ alkynyl, phenyl, naphthyl, furanyl, pyridyl, pyrimidyl, pyrazinyl, thienyl, imidazolyl, pyrazinyl $C_1$-$C_6$ alkyl, pyridyl $C_1$-$C_6$ alkyl, pyrimidyl $C_1$-$C_6$ alkyl, pyrazinyl $C_1$-$C_6$ alkyl, imidazolyl $C_1$-$C_6$ alkyl, furanyl $C_1$-$C_6$ alkyl, thienyl $C_1$-$C_6$ alkyl, heteroarylalkenyl, heteroarylalkynyl, phenyl $C_1$-$C_6$ alkyl, naphthyl $C_1$-$C_6$ alkyl, phenyl $C_2$-$C_6$ alkenyl, naphthyl $C_2$-$C_6$ alkenyl, phenyl $C_2$-$C_6$ alkynyl, naphthyl $C_2$-$C_6$ alkynyl, wherein the cyclic portion of each of the above is unsubstituted or substituted with one or more groups that are independently $C_1$-$C_6$ alkyl, $C_1$-$C_6$ alkoxy, halogen, —SO$_2$-($C_1$-$C_6$) alkyl, $C_1$-$C_4$ haloalkyl, $C_1$-$C_4$ haloalkoxy, NO$_2$, CN, OH, phenyl $C_1$-$C_6$ alkyl wherein the phenyl is optionally substituted with 1, 2, 3, 4, or 5 groups that are independently selected from $C_1$-$C_4$ alkyl, $C_1$-$C_4$ alkoxy, CN, halogen, OH, and alkanoyl, $C_1$-$C_6$ alkoxy $C_1$-$C_6$ alkyl, $C_1$-$C_6$ alkoxycarbonyl, $C_1$-$C_6$ alkanoyl, NR$_7$R$_8$, or —C(O)NR$_7$R$_8$, wherein $R_7$ and $R_8$ are independently H or $C_1$-$C_6$ alkyl, wherein the $C_1$-$C_6$ alkyl is optionally substituted with 1, 2, or 3 groups that are independently $C_1$-$C_6$ alkoxycarbonyl, halogen, $C_1$-$C_6$ alkoxy, $C_1$-$C_6$ alkanoyl, NH$_2$, NH($C_1$-$C_6$ alkyl), N($C_1$-$C_6$ alkyl)($C_1$-$C_6$ alkyl) or CO$_2$H;

wherein the heterocycloalkyl and the cycloalkyl portions of the above are further optionally substituted with =O, =N—OH, or =N—OCH$_3$; or $R_4$ and $R_5$ and the nitrogen to which they are attached form a piperazinyl, morpholinyl, piperidinyl, thiomorpholinyl, imidazolidinyl, S,S,-dioxothiomorpholinyl, piperidinyl, pyrrolidinyl, ring, which is unsubstituted or substituted with 1 or more groups that are independently $C_1$-$C_6$ alkyl, $C_1$-$C_6$ alkoxy, halogen, phenyl $C_1$-$C_6$ alkyl, naphthyl $C_1$-$C_6$ alkyl, $C_1$-$C_6$ alkanoyl, OH, =O, pyridyl, pyrimidyl, pyrazinyl, pyrimidyl $C_1$-$C_6$ alkyl, pyrazinyl $C_1$-$C_6$ alkyl, phenyl, naphthyl, —OCH$_2$CH$_2$O—, —OCH$_2$O—, wherein the pyridyl, pyrimidyl, pyrazinyl, pyrimidyl $C_1$-$C_6$ alkyl, phenyl and naphthyl groups are unsubstituted or substituted with 1 or more groups that are independently $C_1$-$C_4$ alkyl, $C_1$-$C_4$ alkoxy, halogen, CF$_3$ or OCF$_3$.

5. A compound according to claim 4, wherein
$R_2$ and $R_3$ are independently H, halogen, or $C_1$-$C_6$ alkyl.

6. A compound according to claim 5, wherein
Z is a bond, —CH$_2$—, or —NH—.

7. A compound according to claim 6, wherein
$R_1$ is $C_2$-$C_6$ alkynyl, phenyl, thienyl, pyridyl, triazolyl, imidazolyl, pyrazinyl, benzofuranyl, 3,4-dihydropyrimidin-2(1H)-onyl, each of which is unsubstituted or substituted with 1, 2, 3, 4, or 5 groups that are independently $C_1$-$C_6$ alkyl, halogen, $C_1$-$C_6$ alkoxy, OH, CN, CO$_2$H, phenyl, wherein the phenyl is optionally substituted with 1 or more groups that are independently selected from $C_1$-$C_4$ alkyl, $C_1$-$C_4$ alkoxy, halogen, OH, CF$_3$, and OCF$_3$, $C_1$-$C_4$ haloalkyl, $C_1$-$C_4$ haloalkoxy, —OC(O)—$C_1$-$C_6$ alkyl, $C_1$-$C_6$ alkoxycarbonyl, $C_1$-$C_6$ alkanoyl, —C(O)R$_{10}$, or, NR$_6$R$_7$, —(C$_1$-$C_4$ alkyl)-NR$_6$R$_7$, —C(O)NR$_6$R$_7$, wherein each $R_6$ and $R_7$ is independently H, $C_1$-$C_6$ alkyl, $C_1$-$C_4$ alkoxyalkyl, $C_1$-$C_6$ alkoxycarbonyl, wherein the alkyl portion of each is unsubstituted or substituted with 1, 2, or 3, groups that are independently halogen, OH, $C_1$-$C_4$ haloalkyl, $C_1$-$C_4$ haloalkoxy, NH$_2$, NH($C_1$-$C_6$ alkyl) or N($C_1$-$C_6$ alkyl)($C_1$-$C_6$ alkyl); and $R_{10}$ is phenyl, pyridyl, or $C_3$-$C_8$ cycloalkyl, wherein the cyclic portions are optionally substituted with halogen, $C_1$-$C_6$ alkyl, $C_1$-$C_6$ alkoxy, OH, CO$_2$H, CN, NO$_2$, $C_1$-$C_4$ haloalkyl, or $C_1$-$C_4$ haloalkoxy.

8. A compound according to claim 7, wherein
$R_4$ and $R_5$ are independently H, $C_1$-$C_6$ alkyl, $C_1$-$C_4$ alkoxy $C_1$-$C_6$ alkyl, $C_3$-$C_8$ cycloalkyl, piperidinyl, pyrrolidinyl, morpholinyl, morpholinyl $C_1$-$C_6$ alkyl, piperidinyl $C_1$-$C_6$ alkyl, pyrrolidinyl $C_1$-$C_6$ alkyl, piperidinyl $C_2$-$C_6$ alkenyl, pyrrolidinyl $C_2$-$C_6$ alkenyl, morpholinyl $C_2$-$C_6$ alkenyl, piperidinyl $C_2$-$C_6$ alkynyl, pyrrolidinyl $C_2$-$C_6$ alkynyl, morpholinyl $C_2$-$C_6$ alkynyl, phenyl, furanyl, pyridyl, pyrazinyl $C_1$-$C_6$ alkyl, pyridyl $C_1$-$C_6$ alkyl, imidazolyl $C_1$-$C_6$ alkyl, furanyl $C_1$-$C_6$ alkyl, thienyl $C_1$-$C_6$ alkyl, phenyl $C_1$-$C_6$ alkyl, phenyl $C_2$-$C_6$ alkenyl, phenyl $C_2$-$C_6$ alkynyl, wherein the cyclic portion of each of the above is unsubstituted or substituted with one or more groups that are independently $C_1$-$C_6$ alkyl, $C_1$-$C_6$ alkoxy, halogen, —SO$_2$—($C_1$-$C_6$) alkyl, $C_1$-$C_4$ haloalkyl, $C_1$-$C_4$ haloalkoxy, NO$_2$, CN, OH, phenyl $C_1$-$C_6$ alkyl wherein the phenyl is optionally substituted with 1, 2, 3, 4, or 5 groups that are independently selected from $C_1$-$C_4$ alkyl, $C_1$-$C_4$ alkoxy, CN, halogen, OH, and alkanoyl, $C_1$-$C_6$ alkoxy $C_1$-$C_6$ alkyl, $C_1$-$C_6$ alkoxycarbonyl, $C_1$-$C_6$ alkanoyl, NR$_7$R$_8$, or —C(O)NR$_7$R$_8$, wherein $R_7$ and $R_8$ are independently H or $C_1$-$C_6$ alkyl, wherein the $C_1$-$C_6$ alkyl is optionally substituted with 1, 2, or 3 groups that are independently $C_1$-$C_6$ alkoxycarbonyl, halogen, $C_1$-$C_6$ alkoxy, $C_1$-$C_6$ alkanoyl, NH$_2$, NH($C_1$-$C_6$ alkyl), N($C_1$-$C_6$ alkyl)($C_1$-$C_6$ alkyl) or CO$_2$H;

wherein the heterocycloalkyl and the cycloalkyl portions of $R_4$ and $R_5$ are further optionally substituted with =O, =N—OH, or =N—OCH$_3$.

9. A compound according to claim 8, wherein
Z is —NH— or —CH$_2$—;
$R_1$ is $C_2$-$C_6$ alkynyl, phenyl, thienyl, pyridyl, triazolyl, imidazolyl, pyrazinyl, benzofuranyl, 3,4-dihydropyrimidin-2(1H)-onyl, each of which is unsubstituted or substituted with 1, 2, 3, 4, or 5 groups that are independently $C_1$-$C_6$ alkyl, halogen, $C_1$-$C_6$ alkoxy, OH, CN, CO$_2$H, phenyl, wherein the phenyl is optionally substituted with 1 or more groups that are independently selected from $C_1$-$C_4$ alkyl, $C_1$-$C_4$ alkoxy, halogen, OH, $CF_3$, and $OCF_3$, $CF_3$, $OCF_3$, —OC(O)—$C_1$-$C_6$ alkyl, $C_1$-$C_6$ alkoxycarbonyl, $C_1$-$C_6$ alkanoyl, $NR_6R_7$, —($C_1$-$C_4$ alkyl)-$NR_6R_7$, or —C(O)$NR_6R_7$, wherein each $R_6$ and $R_7$ is independently H, $C_1$-$C_6$ alkyl, $C_1$-$C_4$ alkoxyalkyl, $C_1$-$C_6$ alkoxycarbonyl, wherein the alkyl portion of each is unsubstituted or substituted with 1, 2, or 3, groups that are independently halogen, OH, $C_1$-$C_4$ haloalkyl, $C_1$-$C_4$ haloalkoxy, $NH_2$, NH($C_1$-$C_6$ alkyl) or N($C_1$-$C_6$ alkyl) ($C_1$-$C_6$ alkyl); and and $R_4$ and $R_5$ are independently H, $C_1$-$C_6$ alkyl, $C_1$-$C_4$ alkoxy $C_1$-$C_6$ alkyl, $C_3$-$C_8$ cycloalkyl, piperidinyl, pyrrolidinyl, morpholinyl, morpholinyl $C_1$-$C_6$ alkyl, piperidinyl $C_1$-$C_6$ alkyl, pyrrolidinyl $C_1$-$C_6$ alkyl, phenyl, furanyl, pyridyl, pyrazinyl $C_1$-$C_6$ alkyl, pyridyl $C_1$-$C_6$ alkyl, imidazolyl $C_1$-$C_6$ alkyl, furanyl $C_1$-$C_4$ alkyl, thienyl $C_1$-$C_6$ alkyl, phenyl $C_1$-$C_6$ alkyl, wherein the cyclic portion of each of the above is unsubstituted or substituted with one or more groups that are independently $C_1$-$C_6$ alkyl, $C_1$-$C_6$ alkoxy, halogen, —$SO_2$—($C_1$-$C_6$) alkyl, $CF_3$, $OCF_3$, $NO_2$, CN, OH, phenyl $C_1$-$C_6$ alkyl wherein the phenyl is optionally substituted with 1, 2, 3, 4, or 5 groups that are independently selected from $C_1$-$C_4$ alkyl, $C_1$-$C_4$ alkoxy, CN, halogen, OH, and alkanoyl, $C_1$-$C_6$ alkoxy $C_1$-$C_6$ alkyl, $C_1$-$C_6$ alkoxycarbonyl, $C_1$-$C_6$ alkanoyl, $NR_7R_8$, or —C(O)$NR_7R_8$, wherein $R_7$ and $R_8$ are independently H or $C_1$-$C_6$ alkyl, wherein the $C_1$-$C_6$ alkyl is optionally substituted with 1, or 2 groups that are independently $C_1$-$C_6$ alkoxycarbonyl, halogen, $C_1$-$C_6$ alkoxy, $C_1$-$C_6$ alkanoyl, $NH_2$, NH($C_1$-$C_6$ alkyl), N($C_1$-$C_6$ alkyl) ($C_1$-$C_6$ alkyl) or $CO_2H$;

wherein the heterocycloalkyl and the cycloalkyl portions of $R_4$ and $R_5$ are further optionally substituted with =O, =N—OH, or =N—$OCH_3$.

10. A compound according to claim 9, wherein $R_1$ is phenyl, thienyl, pyridyl, imidazolyl, pyrazinyl, benzofuranyl, each of which is unsubstituted or substituted with 1, 2, or 3 groups that are independently $C_1$-$C_6$ alkyl, halogen, $C_1$-$C_6$ alkoxy, OH, CN, $CO_2H$, phenyl, wherein the phenyl is optionally substituted with 1 or more groups that are independently selected from $C_1$-$C_4$ alkyl, $C_1$-$C_4$ alkoxy, halogen, OH, $CF_3$, and $OCF_3$, $CF_3$, $OCF_3$, —OC(O)—$C_1$-$C_6$ alkyl, $C_1$-$C_6$ alkoxycarbonyl, $C_1$-$C_6$ alkanoyl, $NR_6R_7$, —($C_1$-$C_4$ alkyl)-$NR_6R_7$, or —C(O)$NR_6R_7$, wherein each $R_6$ and $R_7$ is independently H, $C_1$-$C_6$ alkyl, or $C_1$-$C_6$ alkoxycarbonyl, wherein the alkyl portion of each is unsubstituted or substituted with 1, 2, or 3, groups that are independently halogen, OH, $CF_3$, $OCF_3$, $NH_2$, NH($C_1$-$C_6$ alkyl) or N($C_1$-$C_6$ alkyl) ($C_1$-$C_6$ alkyl); and and $R_4$ and $R_5$ are independently H, $C_1$-$C_4$ alkyl, $C_3$-$C_6$ cycloalkyl, piperidinyl, pyrrolidinyl, morpholinyl $C_1$-$C_4$ alkyl, piperidinyl $C_1$-$C_4$ alkyl, phenyl, furanyl, pyridyl, pyrazinyl $C_1$-$C_4$ alkyl, pyridyl $C_1$-$C_4$ alkyl, imidazolyl $C_1$-$C_4$ alkyl, furanyl $C_1$-$C_4$ alkyl, thienyl $C_1$-$C_4$ alkyl, phenyl $C_1$-$C_4$ alkyl, wherein the cyclic portion of each of the above is unsubstituted or substituted with one or more groups that are independently $C_1$-$C_6$ alkyl, $C_1$-$C_6$ alkoxy, halogen, —$SO_2$—($C_1$-$C_4$) alkyl, $CF_3$, $OCF_3$, $NO_2$, CN, OH, $NR_7R_8$, or —C(O)$NR_7R_8$, wherein $R_7$ and $R_8$ are independently H or $C_1$-$C_6$ alkyl, wherein the $C_1$-$C_6$ alkyl is optionally substituted with 1, or 2 groups that are independently $C_1$-$C_6$ alkoxycarbonyl, halogen, $C_1$-$C_6$ alkoxy, $C_1$-$C_6$ alkanoyl, $NH_2$, NH($C_1$-$C_6$ alkyl), N($C_1$-$C_6$ alkyl) ($C_1$-$C_6$ alkyl) or $CO_2H$;

wherein the heterocycloalkyl and the cycloalkyl portions of $R_4$ and $R_5$ are further optionally substituted with =O, =N—OH, or =N—$OCH_3$.

11. A compound according to claim 10, wherein $R_4$ is H or methyl; and $R_5$ is —$CH_2$-furanyl.

12. A compound according to claim 11, wherein $R_1$ is phenyl, thienyl, pyridyl, or pyrazinyl, each of which is unsubstituted or substituted with 1, 2, or 3 groups that are independently $C_1$-$C_6$ alkyl, halogen, $C_1$-$C_6$ alkoxy, OH, $CF_3$, $OCF_3$, $NR_6R_7$, —($C_1$-$C_2$ alkyl)-$NR_6R_7$, or —C(O)$NR_6R_7$, wherein each $R_6$ and $R_7$ at each occurrence are independently H, $C_1$-$C_6$ alkyl, or $C_1$-$C_4$ alkoxycarbonyl.

13. A compound according to claim 6, wherein $R_4$ and $R_5$ and the nitrogen to which they are attached form a piperazinyl, morpholinyl, piperidinyl, imidazolidinyl, or pyrrolidinyl ring, each of which is unsubstituted or substituted with 1 or more groups that are independently $C_1$-$C_4$ alkyl, $C_1$-$C_4$ alkoxy, halogen, phenyl $C_1$-$C_4$ alkyl, $C_1$-$C_6$ alkanoyl, OH, pyridyl, pyrimidyl, pyrazinyl, pyrimidyl $C_1$-$C_4$ alkyl, pyrazinyl $C_1$-$C_4$ alkyl, phenyl, —$OCH_2CH_2O$—, —$OCH_2O$—, wherein the pyridyl, pyrimidyl, pyrazinyl, pyrimidyl $C_1$-$C_6$ alkyl, and phenyl groups are unsubstituted or substituted with 1 or more groups that are independently $C_1$-$C_4$ alkyl, $C_1$-$C_4$ alkoxy, halogen, $CF_3$ or $OCF_3$.

14. A compound according to claim 13, wherein $R_1$ is phenyl, thienyl, furanyl, pyridyl, pyrazinyl, triazolyl, imidazolyl, oxazolyl, benzofuranyl, each of which is unsubstituted or substituted with 1, 2, 3, 4, or 5 groups that are independently $C_1$-$C_6$ alkyl, halogen, $C_1$-$C_6$ alkoxy, OH, CN, $CO_2H$, phenyl, wherein the phenyl group is optionally substituted with 1 or more groups that are independently selected from $C_1$-$C_4$ alkyl, $C_1$-$C_4$ alkoxy, halogen, OH, $CF_3$, and $OCF_3$, $CF_3$, $OCF_3$, —OC(O)—$C_1$-$C_4$ alkyl, $C_1$-$C_4$ alkoxycarbonyl, or $C_1$-$C_4$ alkanoyl.

15. A compound according to claim 13, wherein $R_1$ is phenyl, thienyl, pyridyl, pyrazinyl, triazolyl, imidazolyl, benzofuranyl, each of which is unsubstituted or substituted with 1, 2, or 3 groups that are independently $C_1$-$C_6$ alkyl, halogen, $C_1$-$C_6$ alkoxy, OH, —C(O)$R_{10}$, $NR_6R_7$, —($C_1$-$C_4$ alkyl)-$NR_6R_7$, or —C(O)$NR_6R_7$, wherein each $R_6$ and $R_7$ is independently H, $C_1$-$C_6$ alkyl, $C_1$-$C_4$ alkoxyalkyl, $C_1$-$C_6$ alkoxycarbonyl, wherein the alkyl portion of each is unsubstituted or substituted with 1, or 2 groups that are independently halogen, OH, $CF_3$, $OCF_3$, $NH_2$, NH($C_1$-$C_6$ alkyl) or N($C_1$-$C_6$ alkyl) ($C_1$-$C_6$ alkyl);

$R_{10}$ is phenyl, naphthyl, pyridyl, quinolinyl, pyrimidyl, furanyl, indolyl, or $C_3$-$C_8$ cycloalkyl, each of which is optionally substituted with halogen, $C_1$-$C_6$ alkyl, $C_1$-$C_6$ alkoxy, OH, $CO_2H$, CN, $NO_2$, $C_1$-$C_4$ haloalkyl, or $C_1$-$C_4$ haloalkoxy;

wherein the heterocycloalkyl and the cycloalkyl portions of $R_1$ and $R_{10}$ are further optionally substituted with =O, =N—OH, or =N—$OCH_3$.

16. A compound according to claim 15, wherein
$R_4$ and $R_5$ and the nitrogen to which they are attached form a piperazinyl, morpholinyl, piperidinyl, imidazolidinyl, or pyrrolidinyl ring, which is unsubstituted or substituted with 1 or more groups that are independently $C_1$-$C_4$ alkyl, $C_1$-$C_4$ alkoxy, halogen, phenyl $C_1$-$C_2$ alkyl, $C_1$-$C_6$ alkanoyl, OH, pyridyl, pyrimidyl $C_1$-$C_2$ alkyl, phenyl, —OCH$_2$CH$_2$O—, or —OCH$_2$O—; and
$R_2$ and $R_3$ are both H.

17. A compound according to claim 1 which is
8-[5-(2-Dimethylamino-ethylcarbamoyl)-thiophen-2-yl]-[1,6]naphthyridine-2-carboxylic acid (furan-2-ylmethyl)-amide;
8-[5-(2-Diethylamino-ethylcarbamoyl)-thiophen-2-yl]-[1,6]naphthyridine-2-carboxylic acid (furan-2-ylmethyl)-amide;
8-[5-(2-Dimethylamino-ethylcarbamoyl)-thiophen-2-yl]-[1,6]naphthyridine-2-carboxylic acid cyclopropylamide;
8-[5-(2-Diethylamino-ethylcarbamoyl)-thiophen-2-yl]-[1,6]naphthyridine-2-carboxylic acid cyclopropylamide;
5-(2-Methylcarbamoyl-[1,6]naphthyridin-8-yl)-thiophene-2-carboxylic acid amide;
5-(2-Methylcarbamoyl-[1,6]naphthyridin-8-yl)-thiophene-2-carboxylic acid methylamide;
8-[5-(3-Morpholin-4-yl-propylcarbamoyl)-thiophen-2-yl]-[1,6]naphthyridine-2-carboxylic acid methylamide;
8-Thiophen-3-yl[1,6]-naphthyridine-2-carboxylic acid;
8-Thiophen-3-yl[1,6]-naphthyridine-2-carboxylic acid (2-oxo-cyclohexyl)amide;
8-Thiophen-3-yl-[1,6]naphthyridine-2-carboxylic acid amide;
8-Phenyl[1,6]-naphthyridine-2-carboxylic acid;
8-Phenyl[1,6]-naphthyridine-2-carboxylic acid amide;
8-Phenyl[1,6]-naphthyridine-2-carboxylic acid (2-oxo-cyclohexyl)amide;
8-(3-Hydroxy-prop-1-ynyl-[1,6]naphthyridine-2-carboxylic acid cyclopropylamide;
8-(3-Hydroxy-prop-1-ynyl-[1,6]naphthyridine-2-carboxylic acid amide;
8-(3-Hydroxy-prop-1-ynyl-[1,6]naphthyridine-2-carboxylic acid (furan-2-ylmethyl)amide;
(3-{2-[(Furan-2-ylmethyl)-carbamoyl]-[1,6]naphthyridin-8-yl}-prop-2-ynyl)-carbamic acid tert-butyl ester;
8-Phenylethynyl-[1,6]naphthyridine-2-carboxylic acid (furan-2-ylmethyl)-amide;
8-Ethynyl-[1,6]naphthyridine-2-carboxylic acid (furan-2-ylmethyl)-amide;
8-(4-Methoxy-phenylamino)-[1,6]naphthyridine-2-carboxylic acid (furan-2-ylmethyl)-amide;
8-para-Tolylamino-[1,6]naphthyridine-2-carboxylic acid (furan-2-ylmethyl)-amide;
8-Phenylamino-[1,6]naphthyridine-2-carboxylic acid (furan-2-ylmethyl)-amide;
8-(3-Trifluoromethyl-phenylamino0-[1,6]naphthyridine-2-carboxylic acid (furan-2-ylmethyl)-amide;
8-(4-Trifluoromethyl-phenylamino)-[1,6]naphthyridine-2-carboxylic acid (furan-2-ylmethyl)-amide;
8-(Pyridin-3-ylamino)-[1,6]naphthyridine-2-carboxylic acid (furan-2-ylmethyl)-amide;
8-(Pyridin-4-ylamino)-[1,6]naphthyridine-2-carboxylic acid (furan-2-ylmethyl)-amide;
8-(Pyrazin-2-ylamino)-[1,6]naphthyridine-2-carboxylic acid (furan-2-ylmethyl)-amide;
8-(3,5-Dichloro-phenylamino)-[1,6]naphthyridine-2-carboxylic acid (furan-2-ylmethyl)-amide;
8-(4-Methoxy-phenylamino)-[1,6]naphthyridine-2-carboxylic acid cyclopropylamide;
8-(3,5-Dichloro-phenylamino)-[1,6]naphthyridine-2-carboxylic acid cyclopropylamide;
8-(4-Methoxy-phenylamino)-[1,6]naphthyridine-2-carboxylic acid amide;
8-[(Furan-2-ylmethyl)-amino]-[1,6]naphthyridine-2-carboxylic acid (furan-2-ylmethyl)-amide;
8-[(Pyridin-4-ylmethyl)-amino]-[1,6]naphthyridine-2-carboxylic acid (furan-2-ylmethyl)-amide;
8-[(Pyridin-2-ylmethyl)-amino]-[1,6]naphthyridine-2-carboxylic acid (furan-2-ylmethyl)-amide;
8-[(Pyridin-3-ylmethyl)-amino]-[1,6]naphthyridine-2-carboxylic acid (furan-2-ylmethyl)-amide;
8-(3-Methoxy-benzylamino)-[1,6]naphthyridine-2-carboxylic acid (furan-2-ylmethyl)-amide;
8-Cyclopropylamino-[1,6]naphthyridine-2-carboxylic acid (furan-2-ylmethyl)-amide;
8-Prop-2-ynylamino-[1,6]naphthyridine-2-carboxylic acid (furan-2-ylmethyl)-amide;
8-(2-Oxo-pyrrolidin-1-yl)-[1,6]naphthyridine-2-carboxylic acid (furan-2-ylmethyl)-amide;
8-(3-thienyl)-1,6-naphthyridine-2-carboxylic acid;
N-cyclopropyl-8-[5-({[2-(diethylamino)ethyl]amino}carbonyl)-2-thienyl]-1,6-naphthyridine-2-carboxamide;
8-phenyl-1,6-naphthyridine-2-carboxylic acid;
N-(2-furylmethyl)-8-{[4-(trifluoromethyl)phenyl]amino}-1,6-naphthyridine-2-carboxamide;
N-(2-furylmethyl)-8-[(4-methylphenyl)amino]-1,6-naphthyridine-2-carboxamide;
8-anilino-N-(2-furylmethyl)-1,6-naphthyridine-2-carboxamide;
N-(2-furylmethyl)-8-{[3-(trifluoromethyl)phenyl]amino}-1,6-naphthyridine-2-carboxamide;
N-(2-furylmethyl)-8-[(4-methoxyphenyl)amino]-1,6-naphthyridine-2-carboxamide;
N-(2-furylmethyl)-8-(3-hydroxyprop-1-yn-1-yl)-1,6-naphthyridine-2-carboxamide;
8-(5-carboxy-2-thienyl)-1,6-naphthyridine-2-carboxylic acid;
N-(2-furylmethyl)-8-(pyridin-3-ylamino)-1,6-naphthyridine-2-carboxamide;
tert-butyl [3-(2-{[(2-furylmethyl)amino]carbonyl}-1,6-naphthyridin-8-yl)prop-2-yn-1-yl]carbamate;
N-(2-furylmethyl)-8-(pyridin-4-ylamino)-1,6-naphthyridine-2-carboxamide;
8-[5-({[2-(diethylamino)ethyl]amino}carbonyl)-2-thienyl]-N-(2-furylmethyl)-1,6-naphthyridine-2-carboxamide;
8-[5-({[2-(dimethylamino)ethyl]amino}carbonyl)-2-thienyl]-N-(2-furylmethyl)-1,6-naphthyridine-2-carboxamide;
N-cyclopropyl-8-[5-({[2-(dimethylamino)ethyl]amino}carbonyl)-2-thienyl]-1,6-naphthyridine-2-carboxamide;
N-(2-furylmethyl)-8-(pyrazin-2-ylamino)-1,6-naphthyridine-2-carboxamide;
N-(2-oxocyclohexyl)-8-(3-thienyl)-1,6-naphthyridine-2-carboxamide;
N-(2-oxocyclohexyl)-8-phenyl-1,6-naphthyridine-2-carboxamide;
8-(3-hydroxyprop-1-yn-1-yl)-1,6-naphthyridine-2-carboxamide;

N-cyclopropyl-8-(3-hydroxyprop-1-yn-1-yl)-1,6-naphthyridine-2-carboxamide;
N-(2-furylmethyl)-8-(phenylethynyl)-1,6-naphthyridine-2-carboxamide;
8-ethynyl-N-(2-furylmethyl)-1,6-naphthyridine-2-carboxamide;
N-cyclopropyl-8-[(4-methoxyphenyl)amino]-1,6-naphthyridine-2-carboxamide;
2-[(4-benzylpiperazin-1-yl)carbonyl]-8-(4-methoxyphenyl)-1,6-naphthyridine;
N-[4-(methylsulfonyl)benzyl]-8-(3-thienyl)-1,6-naphthyridine-2-carboxamide;
1-{[8-(3-thienyl)-1,6-naphthyridin-2-yl]carbonyl}piperidin-4-ol;
N-(2-methoxyethyl)-8-(3-thienyl)-1,6-naphthyridine-2-carboxamide;
8-(4-methoxyphenyl)-2-[(4-pyridin-2-ylpiperazin-1-yl)carbonyl]-1,6-naphthyridine;
N-(1-benzylpiperidin-4-yl)-8-(4-methoxyphenyl)-1,6-naphthyridine-2-carboxamide;
8-(4-methoxyphenyl)-N-[4-(methylsulfonyl)benzyl]-1,6-naphthyridine-2-carboxamide;
2-(1,4-dioxa-8-azaspiro[4.5]dec-8-ylcarbonyl)-8-phenyl-1,6-naphthyridine;
8-phenyl-2-[(4-pyridin-2-ylpiperazin-1-yl)carbonyl]-1,6-naphthyridine;
2-[(4-benzylpiperazin-1-yl)carbonyl]-8-phenyl-1,6-naphthyridine;
N-(1-benzylpiperidin-4-yl)-8-phenyl-1,6-naphthyridine-2-carboxamide;
N-[4-(methylsulfonyl)benzyl]-8-phenyl-1,6-naphthyridine-2-carboxamide;
2-(1,4-dioxa-8-azaspiro[4.5]dec-8-ylcarbonyl)-8-(3-thienyl)-1,6-naphthyridine;
2-[(4-pyridin-2-ylpiperazin-1-yl)carbonyl]-8-(3-thienyl)-1,6-naphthyridine;
2-[(4-benzylpiperazin-1-yl)carbonyl]-8-(3-thienyl)-1,6-naphthyridine;
N-(1-benzylpiperidin-4-yl)-8-(3-thienyl)-1,6-naphthyridine-2-carboxamide;
2-({4-[(4,6-dimethoxypyrimidin-2-yl)methyl]piperazin-1-yl}carbonyl)-8-(3-thienyl)-1,6-naphthyridine;
1-{[8-(1-benzofuran-2-yl)-1,6-naphthyridin-2-yl]carbonyl}piperidin-4-ol;
8-(1-benzofuran-2-yl)-N-(2-methoxyethyl)-1,6-naphthyridine-2-carboxamide;
1-[(8-phenyl-1,6-naphthyridin-2-yl)carbonyl]piperidin-4-ol;
N-(2-methoxyethyl)-8-phenyl-1,6-naphthyridine-2-carboxamide;
8-(1-benzofuran-2-yl)-2-(1,4-dioxa-8-azaspiro[4.5]dec-8-ylcarbonyl)-1,6-naphthyridine;
8-(1-benzofuran-2-yl)-2-[(4-benzylpiperazin-1-yl)carbonyl]-1,6-naphthyridine;
8-(1-benzofuran-2-yl)-N-(1-benzylpiperidin-4-yl)-1,6-naphthyridine-2-carboxamide;
8-(1-benzofuran-2-yl)-N-[4-(methylsulfonyl)benzyl]-1,6-naphthyridine-2-carboxamide;

or a pharmaceutically acceptable salt thereof.

18. A pharmaceutical composition comprising a compound according to claim 1 and at least one pharmaceutically acceptable solvent, carrier, excipient, adjuvant or a combination thereof.

19. A method of treating a disease or condition selected from inflammation and arthritis comprising administering a therapeutically effective amount of a compound of claim 1 to a patient in need of such treatment.

* * * * *